United States Patent
Belardinelli et al.

(10) Patent No.: US 10,744,087 B2
(45) Date of Patent: Aug. 18, 2020

(54) METHOD TO SLOW VENTRICULAR RATE

(71) Applicant: InCarda Therapeutics, Inc., Newark, CA (US)

(72) Inventors: Luiz Belardinelli, Palo Alto, CA (US); Rangachari Narasimhan, Saratoga, CA (US); Carlos Schuler, Kensington, CA (US)

(73) Assignee: InCarda Therapeutics, Inc., Newark, CA (US)

( * ) Notice: Subject to any disclaimer, the term of this patent is extended or adjusted under 35 U.S.C. 154(b) by 0 days.

(21) Appl. No.: 16/361,649

(22) Filed: Mar. 22, 2019

(65) Prior Publication Data
US 2019/0290581 A1 Sep. 26, 2019

Related U.S. Application Data

(60) Provisional application No. 62/646,528, filed on Mar. 22, 2018.

(51) Int. Cl.
| | | |
|---|---|---|
| *A61P 9/06* | (2006.01) | |
| *A61K 9/00* | (2006.01) | |
| *A61K 31/138* | (2006.01) | |
| *A61K 31/4458* | (2006.01) | |
| *A61K 31/353* | (2006.01) | |

(52) U.S. Cl.
CPC .......... *A61K 9/0073* (2013.01); *A61K 9/0043* (2013.01); *A61K 31/138* (2013.01); *A61K 31/353* (2013.01); *A61K 31/4458* (2013.01); *A61P 9/06* (2018.01)

(58) Field of Classification Search
CPC .. A61K 9/0073; A61K 9/0043; A61K 31/353; A61K 31/138; A61K 31/4458; A61P 9/06
USPC .......................................................... 514/331
See application file for complete search history.

(56) References Cited

U.S. PATENT DOCUMENTS

| | | |
|---|---|---|
| 3,991,761 A | 11/1976 | Cocozza et al. |
| 4,069,819 A | 1/1978 | Valentini et al. |
| 4,114,615 A | 9/1978 | Wetterlin et al. |
| 4,247,066 A | 1/1981 | Frost et al. |
| 4,338,931 A | 7/1982 | Cavazza et al. |

(Continued)

FOREIGN PATENT DOCUMENTS

| | | |
|---|---|---|
| AU | 2013248242 A1 | 11/2013 |
| CN | 101467968 A | 7/2009 |

(Continued)

OTHER PUBLICATIONS

Wikipedia, Beta-1 adrenergic receptor, Oct. 2016, p. 1-7 (Year: 2016).*

(Continued)

*Primary Examiner* — Taylor V Oh
(74) *Attorney, Agent, or Firm* — Wilson Sonsini Goodrich & Rosati

(57) ABSTRACT

Disclosed herein are methods, formulations, and kits for treating or preventing a heart condition, e.g., cardiac arrhythmia, e.g., atrial arrhythmia, using selective β1 adrenergic receptor blockers. Also disclosed herein are methods, formulations, and kits for treating a heart condition via inhalation or intranasal spray administration of selective β1 adrenergic receptor blocker and class I antiarrhythmic agent.

30 Claims, 9 Drawing Sheets

(56) References Cited

U.S. PATENT DOCUMENTS

| | | |
|---|---|---|
| 4,846,876 A | 7/1989 | Draber et al. |
| 4,962,095 A | 10/1990 | Grover et al. |
| 4,995,385 A | 2/1991 | Valentini et al. |
| 5,364,880 A | 11/1994 | Druzgala |
| 5,458,135 A | 10/1995 | Patton et al. |
| 5,619,985 A | 4/1997 | Ohki et al. |
| 5,785,049 A | 7/1998 | Smith et al. |
| 5,855,913 A | 1/1999 | Hanes et al. |
| 5,874,064 A | 2/1999 | Edwards et al. |
| 5,922,675 A | 7/1999 | Baker et al. |
| 5,976,574 A | 11/1999 | Gordon |
| 5,985,248 A | 11/1999 | Gordon et al. |
| 5,985,309 A | 11/1999 | Edwards et al. |
| 6,001,336 A | 12/1999 | Gordon |
| 6,051,256 A | 4/2000 | Platz et al. |
| 6,077,543 A | 6/2000 | Gordon et al. |
| 6,252,113 B1 | 6/2001 | Palmer et al. |
| 6,257,233 B1 | 7/2001 | Burr et al. |
| 6,357,490 B1 | 3/2002 | Johnston et al. |
| 6,358,530 B1 | 3/2002 | Eljamal et al. |
| 6,372,258 B1 | 4/2002 | Platz et al. |
| 6,503,480 B1 | 1/2003 | Edwards et al. |
| 6,546,929 B2 | 4/2003 | Burr et al. |
| 6,632,217 B2 | 10/2003 | Harper et al. |
| 6,740,307 B2 | 5/2004 | Rabinowitz et al. |
| 6,827,947 B2 | 12/2004 | Lofroth et al. |
| 6,946,146 B2 | 9/2005 | Mulye |
| 7,018,620 B2 | 3/2006 | Rabinowitz et al. |
| 7,048,909 B2 | 5/2006 | Rabinowitz et al. |
| 7,090,830 B2 | 8/2006 | Hale et al. |
| 7,302,295 B2 | 11/2007 | Stahmann et al. |
| 7,465,435 B2 | 12/2008 | Rabinowitz et al. |
| 7,473,433 B2 | 1/2009 | Weikert et al. |
| 7,611,728 B2 | 11/2009 | Kidane et al. |
| 7,959,947 B2 | 6/2011 | Holzer et al. |
| 8,003,810 B2 | 8/2011 | Ullucci et al. |
| 8,394,813 B2 | 3/2013 | Mickle et al. |
| 8,460,706 B2 | 6/2013 | Vergnault et al. |
| 8,465,777 B2 | 6/2013 | Wang et al. |
| 8,604,222 B2 | 12/2013 | Sheth et al. |
| 8,641,631 B2 | 2/2014 | Sierra et al. |
| 8,703,193 B2 | 4/2014 | Wang et al. |
| 8,927,025 B2 | 1/2015 | Hamed |
| 8,974,828 B2 | 3/2015 | Schuler et al. |
| 9,192,570 B2 | 11/2015 | Wyse et al. |
| 9,456,997 B2 | 10/2016 | Stauffer et al. |
| 9,474,869 B2 | 10/2016 | Edwards et al. |
| 9,504,655 B2 | 11/2016 | Vats et al. |
| 9,539,221 B2 | 1/2017 | Bond |
| 9,549,912 B2 | 1/2017 | Milner et al. |
| 9,757,528 B2 | 9/2017 | Rubin |
| 9,931,333 B2 | 4/2018 | Arora et al. |
| 9,962,336 B2 | 5/2018 | Singh et al. |
| 1,001,029 A1 | 7/2018 | Narasimhan et al. |
| 1,004,593 A1 | 8/2018 | Schuler et al. |
| 2002/0017295 A1 | 2/2002 | Weers et al. |
| 2002/0115655 A1 | 8/2002 | Mehanna et al. |
| 2003/0005924 A1 | 1/2003 | Rabinowitz et al. |
| 2003/0077229 A1 | 4/2003 | Dugger, III |
| 2003/0079742 A1 | 5/2003 | Giroux |
| 2003/0144701 A1 | 7/2003 | Mehra et al. |
| 2003/0229025 A1 | 12/2003 | Xiao et al. |
| 2004/0011358 A1 | 1/2004 | Smaldone et al. |
| 2004/0035413 A1 | 2/2004 | Smaldone et al. |
| 2004/0045546 A1 | 3/2004 | Hirsh et al. |
| 2004/0099269 A1 | 5/2004 | Hale et al. |
| 2004/0105820 A1 | 6/2004 | Weers et al. |
| 2004/0156792 A1 | 8/2004 | Tarara et al. |
| 2004/0167228 A1 | 8/2004 | Rabinowitz et al. |
| 2005/0009776 A1 | 1/2005 | Gadgil et al. |
| 2005/0070552 A1 | 3/2005 | Fedida et al. |
| 2005/0211245 A1 | 9/2005 | Smaldone et al. |
| 2005/0211253 A1 | 9/2005 | Smaldone et al. |
| 2005/0235987 A1 | 10/2005 | Smaldone et al. |
| 2005/0272810 A1 | 12/2005 | Davis et al. |
| 2006/0034847 A1 | 2/2006 | Yun et al. |
| 2006/0034906 A1 | 2/2006 | Boni et al. |
| 2006/0052333 A1 | 3/2006 | Belardinelli et al. |
| 2006/0120962 A1 | 6/2006 | Rabinowitz et al. |
| 2007/0014733 A1 | 1/2007 | O'Donnell et al. |
| 2007/0014734 A1 | 1/2007 | O'Donnell et al. |
| 2007/0122352 A1 | 5/2007 | Kunka et al. |
| 2007/0122353 A1 | 5/2007 | Hale et al. |
| 2007/0282177 A1 | 12/2007 | Pilz |
| 2008/0038363 A1 | 2/2008 | Zaffaroni et al. |
| 2008/0066741 A1 | 3/2008 | Lemahieu et al. |
| 2008/0161296 A1 | 7/2008 | Davis et al. |
| 2008/0226736 A1 | 9/2008 | Caponetti et al. |
| 2008/0269625 A1 | 10/2008 | Halperin et al. |
| 2008/0275036 A1 | 11/2008 | Cross et al. |
| 2009/0030071 A1 | 1/2009 | Shaw et al. |
| 2010/0086606 A1 | 4/2010 | Ogawa et al. |
| 2010/0305213 A1 | 12/2010 | Beddies et al. |
| 2011/0281853 A1 | 11/2011 | Arora et al. |
| 2012/0003318 A1 | 1/2012 | Schuler et al. |
| 2012/0039884 A1 | 2/2012 | Watson et al. |
| 2014/0290647 A1 | 10/2014 | Salvinelli et al. |
| 2015/0164871 A1 | 6/2015 | Grunnet et al. |
| 2015/0231261 A1 | 8/2015 | Akbarieh et al. |
| 2015/0313842 A1 | 11/2015 | Schuler et al. |
| 2017/0061072 A1 | 3/2017 | Kermani et al. |
| 2017/0151191 A1 | 6/2017 | Charney et al. |
| 2017/0157341 A1 | 6/2017 | Pandya et al. |
| 2018/0296480 A1 | 10/2018 | Schuler et al. |
| 2018/0318213 A1 | 11/2018 | Schuler et al. |
| 2018/0325818 A1 | 11/2018 | Schuler |
| 2019/0060230 A1 | 2/2019 | Schuler et al. |

FOREIGN PATENT DOCUMENTS

| | | |
|---|---|---|
| DE | 102004045796 A1 | 3/2006 |
| DE | 102013009114 A1 | 12/2014 |
| EP | 1370245 B1 | 5/2005 |
| EP | 0976395 B1 | 10/2005 |
| EP | 1322293 B1 | 9/2006 |
| EP | 1276474 B1 | 6/2007 |
| EP | 1886674 A2 | 2/2008 |
| EP | 1889847 A1 | 2/2008 |
| EP | 1911481 A2 | 4/2008 |
| EP | 1982711 A1 | 10/2008 |
| EP | 1455888 B1 | 4/2009 |
| EP | 1406608 B1 | 7/2009 |
| EP | 2102196 A1 | 9/2009 |
| EP | 1886674 B1 | 3/2010 |
| EP | 1242013 B1 | 5/2010 |
| EP | 1741712 B1 | 6/2011 |
| EP | 1842534 B1 | 12/2011 |
| EP | 2081547 B1 | 5/2012 |
| EP | 2533766 B1 | 5/2013 |
| EP | 2649996 A1 | 10/2013 |
| EP | 2276465 B1 | 10/2014 |
| EP | 2808015 A1 | 12/2014 |
| EP | 2520587 B1 | 8/2016 |
| EP | 1848424 B1 | 4/2017 |
| EP | 1866323 B1 | 5/2017 |
| EP | 3024458 B1 | 1/2018 |
| EP | 3308785 A2 | 4/2018 |
| EP | 3485881 A1 | 5/2019 |
| GB | 2522727 A | 8/2015 |
| GB | 2564444 A | 1/2019 |
| JP | 2002529393 A | 9/2002 |
| RU | 38570 U1 | 7/2004 |
| WO | WO-9003144 A1 | 4/1990 |
| WO | WO-9524183 A1 | 9/1995 |
| WO | WO-9531479 A1 | 11/1995 |
| WO | WO-9632096 A1 | 10/1996 |
| WO | WO-9632149 A1 | 10/1996 |
| WO | WO-9916419 A1 | 4/1999 |
| WO | WO-9916420 A1 | 4/1999 |
| WO | WO-9916421 A1 | 4/1999 |
| WO | WO-9916422 A1 | 4/1999 |
| WO | WO-0007572 A2 | 2/2000 |
| WO | WO-0027359 A1 | 5/2000 |
| WO | WO-0072904 A1 | 12/2000 |

(56) References Cited

FOREIGN PATENT DOCUMENTS

| | | |
|---|---|---|
| WO | WO-0185136 A2 | 11/2001 |
| WO | WO-0185137 A2 | 11/2001 |
| WO | WO-0228377 A1 | 4/2002 |
| WO | WO-02083220 A2 | 10/2002 |
| WO | WO-02087508 A2 | 11/2002 |
| WO | WO-02094236 A1 | 11/2002 |
| WO | WO-2004071368 A2 | 8/2004 |
| WO | WO-2005018635 A2 | 3/2005 |
| WO | WO-2005079897 A1 | 9/2005 |
| WO | WO-2005117858 A2 | 12/2005 |
| WO | WO-2006083779 A2 | 8/2006 |
| WO | WO-2006083780 A2 | 8/2006 |
| WO | WO-2006084684 A1 | 8/2006 |
| WO | WO-2007042467 A1 | 4/2007 |
| WO | WO-2007050347 A1 | 5/2007 |
| WO | WO-2008036247 A1 | 3/2008 |
| WO | WO-2008051621 A2 | 5/2008 |
| WO | WO-2008066745 A1 | 6/2008 |
| WO | WO-2008072190 A2 | 6/2008 |
| WO | WO-2008116165 A2 | 9/2008 |
| WO | WO-2008134630 A1 | 11/2008 |
| WO | WO-2010019914 A2 | 2/2010 |
| WO | WO-2010022259 A1 | 2/2010 |
| WO | WO-2010042658 A1 | 4/2010 |
| WO | WO-2010107964 A1 | 9/2010 |
| WO | WO-2011060943 A1 | 5/2011 |
| WO | WO-2012024106 A2 | 2/2012 |
| WO | WO-2014191837 A2 | 12/2014 |
| WO | WO-2015021954 A1 | 2/2015 |
| WO | WO-2015079197 A1 | 6/2015 |
| WO | WO-2016090009 A1 | 6/2016 |
| WO | WO-2017134200 A1 | 8/2017 |
| WO | WO-2017136421 A1 | 8/2017 |

OTHER PUBLICATIONS

Capucci et al , Flecainide—metoprolol combination reduces atrial fibrillation clinical recurrences and improves tolerability at 1-year follow-up in persistent symptomatic atrial fibrillation, Clinical Research , Europace ,2016, 18, p. 1698-1704 (Year: 2016).*
Abarbanell, et al. Prehospital management of rapid atrial fibrillation: recommendations for treatment protocols. Am J Emerg Med. Jan. 2001;19(1):6-9.
Barbato, et al. Role of beta2 adrenergic receptors in human atherosclerotic coronary arteries. Circulation. 2005, 111:288-294.
Borlak, et al. Metabolism of verapamil in cultures of rat alveolar epithelial cells and pharmacokinetics after administration by intravenous and inhalation routes. Drug Metab Dispos. Aug. 2005;33(8):1108-14. Epub May 10, 2005.
Co-pending U.S. Appl. No. 15/928,851, filed Mar. 22, 2018.
Dell'Orfano, et al. Drugs for Conversion of Atrial Fibrillation. Am. Fam. Physician. 58(2); 471-480, Aug. 1, 1998. 6 pages.
Deneer, et al. Absorption kinetics and pharmacodynamics of two oral dosage forms of flecainide in patients with an episode of paroxysmal atrial fibrillation. Eur J Clin Pharmacol. Dec. 2004;60(10):693-701.
European Office Action dated Nov. 16, 2017 for European Patent Application No. EP10754091.6.
European search report and search opinion dated Jan. 21, 2014 for EP Application No. 10754091.6.
Feldman, et al. Analysis of Coronary Response to Various Doses of Intracoronary Nitroglycerin. Circulation. 1982, 66:321-327.
Gaglione, et al. Is There Coronary Vasoconstriction after Intracoronary Beta-adrenergic Blockade in Patients with Coronary Artery Disease. J Am Coll Cardiol. 1987, 10:299-310.
Harrison, et al. Effect of Single Doses of Inhaled Lignocaine on FEV1 and Bronchial Reactivity in Asthma. Respir Med. Dec. 1992, 12:1359-635.
Ikeda, "Effects of Flecainide on the Electrophysiologic Properties of Isolated Canine and Rabbit Myocardial Fibers", JACC, vol. 5, No. 2, pp. 303-310, Feb. 1985.

International Search Report and Written Opinion dated Apr. 18, 2017 for International PCT Patent Application No. PCT/US2017/016018.
International search report and written opinion dated Jul. 12, 2010 for PCT Application No. PCT/US2010/027740.
Juan Tamargo et al., "Narrow therapeutic index drugs: a clinical pharmacological consideration to flecainide", EurJ Clin Pharmacol, vol. 71, 549-567, 2015.
Kroemer, "Flecainide enantiomers: Disposition i human subjects and electrophysiologic actions in vitro", Clinical Pharmacology & Therapeutics, vol. 46, Issue 5, pp. 584-590, Nov. 1989.
Lopez-Vidriero, M.T. Issues relating to safety and efficacy in nebulizer use. Eur. Respir. Rev., 2000, 10:72, 210-212.
Noguchi, et al. Effects of Intracoronary Propranolol on Coronary Blood Flow and Regional Myocardial Function in Dogs. EurJ Pharmacol. 1987, 144(2):201-10.
Notice of allowance dated Jan. 21, 2015 for U.S. Appl. No. 13/257,249.
Office action dated Jan. 3, 2013 for U.S. Appl. No. 13/257,249.
Office Action dated Apr. 17, 2017 for U.S. Appl. No. 14/632,252.
Office Action dated Apr. 27, 2016 for U.S. Appl. No. 14/632,252.
Office action dated Jun. 20, 2014 for U.S. Appl. No. 13/257,249.
Office Action dated Jul. 24, 2017 for U.S. Appl. No. 15/422,053.
Office action dated Sep. 09, 2015 for U.S. Appl. No. 14/632,252.
Office action dated Sep. 26, 2013 for U.S. Appl. No. 13/257,249.
Office Action dated Dec. 1, 2016 for U.S. Appl. No. 14/632,252.
Office Action dated Dec. 28, 2018 for U.S. Appl. No. 16/172,456.
Alessandro Capucci et al., "Flecainide—metoprolol combination reduces atrial fibrillation clinical recurrences and improves tolerability at 1-year follow-up in persistent symptomatic atrial fibrillation", Europace, vol. 18, pp. 1698-1704, 2016.
Alexandre A. Maruma et al., Optimizing flecainide plasma concentration profile for atrial fibrillation conversion while minimizing adverse ventricular effects by rapid, low-dose intratracheal or intravenous administration , International Journal of Cardiology, vol. 274 2019, pp. 170-174.
Bart A. Mulder et al., "Effect of nebivolol on outcome in elderly patients with heart failure and atrial fibrillation: insights from SENIORS", European Journal of Heart Failure, vol. 14, pp. 1171-1178, 2012.
PCT/US2018/032092 International Search Report and Written Opinion dated Aug. 1, 2018.
Djupesland PG, "Nasal drug delivery devices: characteristics and performance in a clinical perspective-a review", Drug Deliv Trans! Res., 3(1), pp. 42-62, Feb. 2013, Published online Oct. 18, 2012. doi: 10.1007/s13346-012-0108-9 PMCID: PMC3539067, PMID: 23316447.
Dudink Elton,MD et al., "Acute cardioversion vs a wait-and-see approach for recent-onset symptomatic atrial fibrillation in the emergency department: Rationale and design of the randomized ACWAS trial", American Heart Journal, pp. 49-53, Jan. 2017.
Etienne Aliot et al., "Twenty-five years in the making: flecainide is safe and effective for the management of atrial fibrillation", Europace, vol. 13, pp. 161-173, 2011.
Fernando G. Stocco, BS et al., "Comparative Pharmacokinetic and Electrocardiographic Effects of Intratracheal and Intravenous Administration of Flecainide in Anesthetized Pigs", J Cardiovasc Pharmacol, vol. 72, No. 3, Sep. 2018, pp. 129-135.
Gerard C. Markey, MCH, FRCEM et al., "Intravenous Flecainide for Emergency Department Management of Acute Atrial Fibrillation", The Journal of Emergency Medicine, pp. 1-8, 2017.
H. Stern, "Antiarrhythmic therapy with flecainide in combination and comparison with propranolol", Drugs, vol. 29 Supplement 4, pp. 77-85, 1985.
Highlights of Prescribing Information, Reference ID: 3940505, pp. 1-23, Revised Jun. 2016.
L. Belardinelli et al., A Novel Approach to Deliver Flecainide to the Heart: A Study in Healthy Volunteers to Compare the Cardiovascular Effects of Inhaled vs Intravenous Flecainide, InCarda Therapeutics, 2017, poster 1 page and abstract.
L. Belardinelli et al., Hand-held Breath-Actuated Nebulizer for Delivery of Flecainide to the Heart: Dose-Concentration Dependent

(56) References Cited

OTHER PUBLICATIONS

Pharmacokinetics and QRS Interval Prolongation of Inhaled Flecainide in Healthy Volunteers, InCarda Therapeutics, 2017, poster 1 page and abstract.
L Belardinelli et al., Rapid Cardioversion of Recent-onset Atrial Fibrillation with Pulmonary Delivery of Flecainide in Anesthetized Dogs, Abstract for Heart Rhythm Society meeting 2017, Chicago, May 4, 2017, 1 page.
Nikolaos Fragakis et al., "Acute beta-adrenoceptor blockade improves efficacy of ibutilide in conversion of atrial fibrillation with a rapid ventricular rate", Europace (2009) 11, pp. 70-74.
Paul Dorian, MD et al., b-Blockers and Atrial Fibrillation: Hypertension and Other Medical Conditions Influencing Their Use, Canadian Journal of Cardiology, vol. 30, S38-S41, 2014.
Platia EV et al., "Esmolol versus verapamil in the acute treatment of atrial fibrillation or atrial flutter", Am J Cardiol. Apr. 15, 1989;63(13):925-9.
Rehnqvist N., "Clinical experience with intravenous metoprolol in supraventricular tachyarrhythmias. A multicentre study", Ann Clin Res. 1981;13 Suppl 30:68-72.
Richard L. Page, MD, "Beta-Blockers for Atrial Fibrillation: Must We Consider Asymptomatic Arrhythmias?", Journal of the American College of Cardiology, vol. 36, No. 1, pp. 147-150, 2000.
Richard L. Verrier, PhD, FHRS et al., "Accelerated conversion of atrial fibrillation to normal sinus rhythm by pulmonary delivery of flecainide acetate in a porcine model", Heart Rhythm, vol. 15, No. 12, Dec. 2018, pp. 1882-1888.
Shubik luV et al., "Heart rate control with nebivolol in patients with tachysystolic atrial Fibrillation", Kardiologiia. 2003;43(9):525, https://www.ncbi.nlm.nih.gov/pubmed/?term=Heart+rate+control+with+nebivolol+in+patients+with+tachysystolic+atrial+fibrillation.
Isabelle C Van Gelder et al., "Rate control in atrial fibrillation", Atrial fibrillation 2, http://www.thelancet.com, vol. 388, Aug. 20, 2016, pp. 818-828.
Victor Z. de Antonio BS et al., "Pulmonary delivery of flecainide causes a rate☐dependent predominant effect on atrial compared with ventricular depolarization duration revealed by intracardiac recordings in an intact porcine model", J Cardiovasc Electrophysiol., vol. 29 2018, pp. 1563-1569.
Rabinowitz, et al. Ultra-fast absorption of amorphous pure drug aerosols via deep lung inhalation. J Pharm Sci. Nov. 2006;95(11):2438-51.
Razavi, M. Safe and effective pharmacologic management of arrhythmias. Tex Heart Inst J. 2005;32(2):209-11.
U.S. Appl. No. 15/422,053 Notice of Allowance dated Mar. 5, 2018.
Suttorp, et al. The value of class IC antiarrhythmic drugs for acute conversion of paroxysmal atrial fibrillation or flutter to sinus rhythm. J Am Coll Cardiol. Dec. 1990;16(7):1722-7.
Twiss, et al. Efficacy of Calcium Channel Blockers as Maintenance Therapy for Asthma. British J of Clinical Pharmacology. Nov. 2001.
U.S. Appl. No. 14/632,252 Notice of Allowance dated Mar. 29, 2018.
U.S. Appl. No. 16/013,165 Final Office Action dated May 9, 2019.
U.S. Appl. No. 16/013,178 Final Office Action dated May 10, 2019.
U.S. Appl. No. 15/928,851 Office Action dated Oct. 9, 2018.
U.S. Appl. No. 16/013,165 Office Acton dated Aug. 28, 2018.
U.S. Appl. No. 16/013,178 Office Action dated Sep. 18, 2018.
Zalewski, et al. Myocardial Protection during Transient Coronary Artery Occlusion in Man: Beneficial Effects of Regional Beta-adrenergic Blockade. Circulation. 1986, 73:734-73.
Carruthers, S. G. et al., "Relationships between heart rate and PR interval during physiological and pharmacological interventions", British Journal of Clinical Pharmacology, Mar. 1987, vol. 23, pp. 259-265.
Maffei, Angelo et al., "Characterization of Nitric Oxide Release by Nebivolol and Its Metabolites", American Journal of Hypertension, Jun. 1, 2006, vol. 19, pp. 579-586.
PCT/US2019/023569 International Search Report and Written Opinion dated Oct. 10, 2019.
Wong et al., "Blood pressure lowering efficacy of dual alpha and beta blockers for primary hypertension", Cochrane Systematic Review, Aug. 26, 2015.
Workman, Antony J. "Cardiac adrenergic control and atrial fibrillation", Nauyn-Schmiedeberg's Archives of Pharmacology, 2010, 381:235-249.
European Search Report dated Sep. 2, 2019 for EP Application No. 19176305.1.
European Search Report dated Sep. 4, 2019 for EP Application No. 19176272.3.
Search Report dated Nov. 22, 2019 for Application No. 11201805788W, (2 pages).
Supplementary European Search Report dated Aug. 6, 2019 for EP Application No. 17748062.1.
U.S. Appl. No. 15/976,516 Office Action dated Mar. 19, 2019.
U.S. Appl. No. 16/172,456 Final Office Action dated Sep. 27, 2019.
U.S. Appl. No. 16/192,337 Non-Final Office Action dated Dec. 12, 2019.
Written Opinion dated Nov. 29, 2019 for Application No. 11201805788W, (6 pages).
"Flecainide" entry in Chem Spider website online retrieved on May 11, 2020 from URL:www.chemspider.com/Chemical-Structure.3239.html>.
U.S. Appl. No. 16/172,456 Non-Final Office Action dated May 11, 2020.
U.S. Appl. No. 16/789,151 Non-Final Office Action dated May 19, 2020.
U.S. Appl. No. 16/789,156 Non-Final Office Action dated May 22, 2020.

\* cited by examiner

METHOD TO SLOW VENTRICULAR RATE

CROSS-REFERENCE

This application claims the benefit of U.S. provisional application No. 62/646,528, filed Mar. 22, 2018, which is incorporated herein by reference in its entirety.

BACKGROUND

The ideal therapy for rate-control in patients in cardiac arrhythmia, e.g., AF, will be one that is safe, well tolerated, that can be quickly and easily delivered, has fast onset to effect, and exhibits a duration of effect for several hours after a single or repeated administration for in- and out-of-hospital use. This is a difficult goal to achieve, e.g., not met by any of the current therapies available to manage patients with atrial fibrillation.

Effective methods, formulations, and kits are needed to address a potential life-threatening condition associated with acute cardioversion of atrial fibrillation (AF) in particular with class 1c agents such as flecainide. During conversion of AF to normal sinus rhythm a transient rhythm called atrial flutter may occur. If atrioventricular (AV) nodal conduction (transmission) is not slowed, atrial flutter with 1:1 AV conduction may emerge, resulting in a very fast ventricular rate, akin to ventricular tachycardia. Atrial flutter with 1:1 conduction is associated with severe haemodynamic instability and potentially progression to ventricular fibrillation. This can become a life-threatening condition.

Beta blockers, also written as β-blockers, are a class of drugs that can be cardio-selective and can be used to modulate, e.g., to slow the ventricular heart rate in patients with AF—what is called the "rate control strategy" for the management of patients with AF. Beta blockers may selectively block β-adrenergic receptors, such as β1 adrenergic receptors (β1AR).

Currently, β1AR blockers are delivered intravenously and/or as oral tablets. Although IV or oral administration of β1AR blockers is used for rate control (e.g., slowing ventricular rate) in patients with atrial fibrillation, they have not been proven superior to placebo for acute conversion of nonpostoperative atrial fibrillation (McNamara et al. Ann. Intern. Med. 2003, 139:1018-1033). Currently β1AR blockers, either PO or IV, are not recommended in use for acute conversion of atrial fibrillation to normal sinus rhythm. For instance, soltalol, a noncardioselective β1AR (it can also block potassium channels) has been reported in several studies to have efficacy (when given in oral pills) for acute conversion of atrial fibrillation to normal sinus rhythm in the range of 8-49% (reviewed in Ferreira et al. Pharmacotherapy 1997; 17:1233-1237). Another commonly used β1AR blocker, metoprolol, when given intravenously (5 to 15 mg bolus doses) was reported to have a conversion rate of atrial arrhythmia of 13% only, although was effective in reducing the rate for at least 25% or reducing it to less than 100 bpm in 68% of the patients (Rehnqvist N., Ann. Clin. Res. 1981; 13 Suppl 30:68-72). In another study (Platia E V, et al. Am. J. Cardiol. 1989; 63:925-929), about 50% of esmolol-treated patients with new onset atrial fibrillation or flutter converted to sinus rhythm.

Drugs administered via the IV route are significantly diluted in the venous blood volume and lungs before reaching the cardiac circulation. For example, they may have a short half-life and may require continuous infusion for a long period of time, which can preclude unassisted safe use of this drug by patients at-home. Some β1AR blockers, when delivered orally, may be absorbed slowly and only reach mean peak plasma concentrations from 0.5 hours post dosing in some patients up to 2 hours post-dosing. This may be due to variability in first-pass metabolism; some patients are extensive metabolizers while others are poor metabolizers. This variability may complicate determining the appropriate dose for a given patient, thus requiring careful titration for each patient, as a dose that is too low may not be effective, and a dose that is too high may result in undesirable side effects.

SUMMARY

In one aspect, the present disclosure provides a method of treating a subject suffering from atrial arrhythmia, comprising: administering to the subject via inhalation a therapeutically effective amount of a β1-selective adrenergic receptor blocker, thereby inducing cardioversion of the atrial arrhythmia in the subject and slowing atrioventricular (AV) node conduction during the cardioversion.

In another aspect, the present disclosure provides a method of treating a subject suffering from atrial arrhythmia, comprising: administering to the subject via inhalation a therapeutically effective amount of aβ1-selective adrenergic receptor blocker and a therapeutically effective amount of class I antiarrhythmic agent.

In some cases, the administering induces cardioversion of the atrial arrhythmia in the subject In some cases, the administering slows atrioventricular (AV) node conduction during the cardioversion. In some cases, a concentration of the β1-selective adrenergic receptor blocker in the coronary arterial circulation of the heart is between about 0.001 mg/L and about 0.1 mg/L at 2.5 minutes after the administering. In some cases, a concentration of the β1-selective adrenergic receptor blocker in the coronary arterial circulation of the heart is between about 0.01 mg/L and about 0.1 mg/L at 2.5 minutes after the administering. In some cases, a concentration of the β1-selective adrenergic receptor blocker in the coronary arterial circulation of the heart peaks at between about 0.01 mg/L and about 0.1 mg/L. In some cases, the cardioversion restores sinus rhythm in the subject to normal within 10 min after the administering. In some cases, the administering prolongs PR interval in the subject during the cardioversion as measured by electrocardiograph. In some cases, the PR interval in the subject is prolonged for at least about 5%. In some cases, the PR interval in the subject is prolonged for at least about 10%. In some cases, the administering reduces average ventricular rate in the subject during the cardioversion by at least about 10%. In some cases, the average ventricular rate during the cardioversion is reduced by at least about 20%. In some cases, the average ventricular rate during the cardioversion is reduced to below 110 beats per min (bpm). In some cases, the average ventricular rate during the cardioversion is reduced to below 90 bpm. In some cases, a change in ventricular contractility in the subject induced by the cardioversion is not substantially affected by the administering. In some cases, a mean arterial pressure of the subject is not substantially reduced by the administering. In some cases, the administering both of the therapeutically effective amount of the β1-selective adrenergic receptor blocker and the therapeutically effective amount of the class I antiarrhythmic agent induces cardioversion of the atrial arrhythmia in the subject faster than administering the therapeutically effective amount of the β1-selective adrenergic receptor blocker without a class I antiarrhythmic agent or the therapeutically effective amount of the class I antiarrhythmic agent in the subject without aβ1-selective adrenergic receptor blocker. In some cases, the administering of both of the therapeutically effective amount of the β1-selective adrenergic receptor blocker and the therapeutically effective amount of the class I antiarrhythmic agent induces a greater reduction in average ventricular rate during the cardioversion in the subject than administering the therapeutically effective amount of the β1-selective adrenergic receptor blocker without a class I antiarrhythmic agent or the therapeutically effective amount of the class I antiarrhythmic agent in the subject without aβ1-selective adrenergic receptor blocker.

In some cases, the method comprises administering about 1 mg to about 60 mg of the β1-selective adrenergic receptor blocker. In some cases, the method comprises administering about 1 mg to about 4 mg of the β1-selective adrenergic receptor blocker. In some cases, the β1-selective adrenergic receptor blocker is administered at a concentration of about 1 mg/mL to about 60 mg/mL. In some cases, the β1-selective adrenergic receptor blocker is administered at a concentration of about 2 mg/mL to about 30 mg/mL.

In some cases, the β1-selective adrenergic receptor blocker comprises metoprolol or a pharmaceutically acceptable salt or solvate thereof. In some cases, the β1-selective adrenergic receptor blocker comprises metoprolol tartrate. In some cases, the method comprises administering about 1 mg to about 4 mg metoprolol or a pharmaceutically acceptable salt or solvate thereof. In some cases, the method comprises administering at most about 2 mg metoprolol or a pharmaceutically acceptable salt or solvate thereof. In some cases, the metoprolol or a pharmaceutically acceptable salt or solvate thereof is administered at a concentration of about 1 mg/mL to about 60 mg/mL. In some cases, metoprolol or a pharmaceutically acceptable salt or solvate thereof is administered at a concentration of about 2 mg/mL to about 30 mg/mL. In some cases, the method comprises administering about 1 mg to about 4 mg metoprolol or a pharmaceutically acceptable salt or solvate thereof at a concentration of about 2 mg/mL to about 30 mg/mL.

In some cases, the β1-selective adrenergic receptor blocker comprises nebivolol or a pharmaceutically acceptable salt or solvate thereof. In some cases, the method comprises administering about 1 mg to about 20 mg nebivolol or a pharmaceutically acceptable salt or solvate thereof. In some cases, the method comprises administering at most about 2.5 mg nebivolol or a pharmaceutically acceptable salt or solvate thereof. In some cases, the nebivolol or a pharmaceutically acceptable salt or solvate thereof is administered at a concentration of about 2 mg/mL to about 30 mg/mL. In some cases, the method comprises administering about 1 mg to about 10 mg nebivolol or a pharmaceutically acceptable salt or solvate thereof at a concentration of about 2 mg/mL to about 30 mg/mL. In some cases, the method comprises the nebivolol is a racemic mixture. In some cases, the method comprises the nebivolol comprises about 100% D-nebivolol.

In some cases, the β1-selective adrenergic receptor blocker is administered prior to the class I antiarrhythmic agent. In some cases, the β1-selective adrenergic receptor blocker is administered up to about 90 minutes earlier than the dosage of the class I antiarrhythmic agent. In some cases, the β1-selective adrenergic receptor blocker is administered concurrently with the class I antiarrhythmic agent. In some cases, the β1-selective adrenergic receptor blocker is administered in a same liquid solution with the class I antiarrhythmic agent. In some cases, the class I antiarrhythmic agent comprises flecainide or a pharmaceutically acceptable salt or solvate thereof. In some cases, the method comprises administering about 20 mg to about 250 mg flecainide or a pharmaceutically acceptable salt or solvate thereof. In some cases, the method comprises administering about 20 mg to about 90 mg flecainide or a pharmaceutically acceptable salt or solvate thereof. In some cases, the flecainide or a pharmaceutically acceptable salt or solvate thereof is administered at a concentration of about 10 to about 90 mg/mL. In some cases, the class I antiarrhythmic agent comprises flecainide acetate. In some cases, the class I antiarrhythmic agent is selected from the group consisting of: quinidine, procainamide, disopyramide, lidocaine, tocainide, phenytoin, moricizine, mexiletine, flecainide, propafenone, and moricizine.

In some cases, the method comprises administering about 1 mg to about 4 mg metoprolol or a pharmaceutically acceptable salt or solvate thereof at a concentration of about 2 mg/mL to about 30 mg/mL up to 90 minutes prior to administering about 20 mg to about 90 mg flecainide or a pharmaceutically acceptable salt or solvate thereof via aerosolization. In some cases, the method comprises administering concurrently via aerosolization about 1 mg to about 4 mg metoprolol or a pharmaceutically acceptable salt or solvate thereof at a concentration of about 2 mg/mL to about 30 mg/mL and about 20 mg to about 90 mg flecainide or a pharmaceutically acceptable salt or solvate thereof. In some cases, the method comprises administering about 1 mg to about 10 mg nebivolol or a pharmaceutically acceptable salt or solvate thereof at a concentration of about 2 mg/mL to about 30 mg/mL up to 90 minutes prior to administering about 20 mg to about 90 mg flecainide or a pharmaceutically acceptable salt or solvate thereof via aerosolization. In some cases, the method comprises administering concurrently via aerosolization about 1 mg to about 10 mg nebivolol or a pharmaceutically acceptable salt or solvate thereof at a concentration of about 2 mg/mL to about 30 mg/mL and about 20 mg to about 90 mg flecainide or a pharmaceutically acceptable salt or solvate thereof.

In some cases, the administering comprises aerosolization of the therapeutically effective amount of the β1-selective adrenergic receptor blocker. In some cases, the administering comprises aerosolization of the therapeutically effective amount of the β1-selective adrenergic receptor blocker and the therapeutically effective amount of the class I antiarrhythmic agent. In some cases, the aerosolization comprises nebulization. In some cases, the aerosolization is performed by a jet nebulizer. In some cases, the aerosolization occurs at room temperature. In some cases, the aerosolization forms aerosols having particles having a mass median diameter of less than 10 μm. In some cases, the atrial arrhythmia comprises tachycardia. In some cases, the tachycardia is selected from the group consisting of: supraventricular tachycardia, paroxysmal supraventricular tachycardia, persistent atrial fibrillation, paroxysmal atrial fibrillation, acute episodes in persistent and permanent atrial fibrillation, atrial flutter, paroxysmal atrial flutter, and lone atrial fibrillation. In some cases, the atrial arrhythmia comprises atrial fibrillation. In some cases, the administering comprises 1 to 6 inhalations. In some cases, the subject is a human subject. In some cases, the method prevents atrial flutter from occurring concurrently with 1:1 AV node conduction ratio during the cardioversion.

In one aspect, disclosed herein is a kit comprising: a first unit dose comprising a β1-selective adrenergic receptor blocker; and a second unit dose comprising a class I antiarrhythmic agent. In some cases, the first unit dose and the second unit dose are effective for treatment of atrial arrhythmia in a subject in need thereof when both are administered to the subject via inhalation by inducing cardioversion of the atrial arrhythmia in the subject, and slowing atrioventricular (AV) node conduction during the cardioversion.

In some cases, the kit comprises a first container containing the first unit dose comprising the β1-selective adrenergic receptor blocker, and a second container containing the second unit dose comprising the class I antiarrhythmic agent. In some cases, the β1-selective adrenergic receptor blocker and the class I antiarrhythmic agent are in a single liquid solution. In some cases, the kit comprises an aerosol of the first unit dose comprising the β1-selective adrenergic receptor blocker and the second unit dose comprising the class I antiarrhythmic agent. In some cases, the kit further comprises an aerosolization device. In some cases, the aerosolization device is configured to deliver the β1-selective adrenergic receptor blocker and the class I antiarrhythmic agent concurrently via the aerosolization device. In some cases, the first unit dose comprises about 1 mg to about 60 mg of the β1-selective adrenergic receptor blocker. In some cases, the unit dose comprises about 1 mg to about 250 mg class I antiarrhythmic agent. In some cases, the β1-selective adrenergic receptor blocker is in a liquid solution at a concentration of about 1 mg/mL to about 60 mg/mL. In some cases, the β1-selective adrenergic receptor blocker comprises metoprolol or a pharmaceutically acceptable salt or solvate thereof. In some cases, the β1-selective adrenergic receptor blocker comprises metoprolol tartrate. In some cases, the kit comprises about 1 mg to about 60 mg metoprolol or a pharmaceutically acceptable salt or solvate thereof. In some cases, the metoprolol or a pharmaceutically acceptable salt or solvate thereof is in a liquid solution at a concentration of about 1 mg/mL to about 60 mg/mL. In some cases, the β1-selective adrenergic receptor blocker comprises nebivolol or a pharmaceutically acceptable salt or solvate thereof. In some cases, the kit comprises about 1 mg to about 30 mg nebivolol or a pharmaceutically acceptable salt or solvate thereof. In some cases, the nebivolol or a pharmaceutically acceptable salt or solvate thereof is in a liquid solution at a concentration of about 2 mg/mL to about 30 mg/mL. In some cases, the kit comprises about 1 mg to about 10 mg nebivolol or a pharmaceutically acceptable salt or solvate thereof at a concentration of about 2 mg/mL to about 30 mg/mL. In some cases, the nebivolol comprises about 100% D-nebivolol. In some cases, the class I antiarrhythmic agent comprises flecainide or a pharmaceutically acceptable salt or solvate thereof. In some cases, the kit comprises about 20 mg to about 250 mg flecainide or a pharmaceutically acceptable salt or solvate thereof. In some cases, the kit comprises about 20 mg to about 90 mg flecainide or a pharmaceutically acceptable salt or solvate thereof. In some cases, the flecainide or a pharmaceutically acceptable salt or solvate thereof has a concentration of about 10 to about 90 mg/mL. In some cases, the class I antiarrhythmic agent comprises flecainide acetate. In some cases, the first and second unit doses further comprise a pharmaceutically acceptable excipient or carrier. In some cases, the first and second unit doses further comprise a pH buffer. In some cases, the pH buffer is selected from the group consisting of: acetate, tris, citrate, phosphate, phthalate, and lactate. In some cases, the aerosolization device is selected from the group consisting of: a nebulizer, a metered dose inhaler, a liquid dose instillation device, and a dry powder inhaler. In some cases, the aerosolization device is a jet nebulizer. In some cases, the aerosolization device is configured for aerosolization at room temperature. In some cases, the aerosolization device is configured to form an aerosol having particles having a mass median diameter of less than 10 μm.

One aspect of the present disclosure provides a method of treating or preventing a heart condition, comprising: administering, by oral or nasal administration, an effective amount of a selective β-1 adrenergic receptor (β1AR) blocker to a patient in need thereof, such that the selective β1AR first enters the heart through the pulmonary veins to the left atrium.

In some cases, the oral or nasal administration comprises oral inhalation, nasal inhalation, or intranasal spray administration.

In some cases, the heart condition comprises tachycardia, atrial ectopy, or both. In some cases, the tachycardia comprises sinus tachycardia, atrial fibrillation, atrial flutter, AV nodal reentrant tachycardia, accessory pathway mediated tachycardia, atrial tachycardia, multifocal atrial tachycardia, junctional tachycardia, ventricular tachycardia, supraventricular tachycardia, or any combination thereof. In some cases, the heart condition arises during cardioversion of atrial fibrillation.

In some cases, the selective β1AR blocker comprises atenolol, acebutolol, bisoprolol, betaxolol, celiprolol, esmolol, metoprolol, nebivolol, or any combination thereof. In some cases, the selective β1AR blocker comprises nebivolol. In some cases, more than 50%, 60%, 70%, 80%, 90%, 95%, 96%, 97%, 97.5%, 98%, 98.5%, 99%, 99.5%, 99.6%, 99.7%, 99.8%, or 99.9%, or about 100% of the nebivolol is d-nebivolol. In some cases, the nebivolol is d-nebivolol.

In some cases, the effective amount of the β1AR is in a range of 1 μg to 10 μg, 1 μg to 100 μg, 1 μg to 1 mg, 1 μg to 10 mg, 1 μg to 50 mg, 10 μg to 100 μg, 10 μg to 1 mg, 10 μg to 10 mg, 10 μg to 50 mg, 100 μg to 1 mg, 100 μg to 10 mg, or 100 μg to 50 mg.

In some cases, a method of present disclosure further comprises: inducing cardioversion in the patient. In some cases, the administering the effective amount of the selective β1AR blocker prevents or suppresses tachycardia, atrial ectopy, or both, associated with the cardioversion.

In some cases, the administering takes place prior to the inducing. In some cases, the administering takes place 1 to 30, 5 to 30, 1 to 15, 5 to 15, 1 to 10, or 5 to 10 minutes prior to the induction of cardioversion. In some cases, the administering and the induction of cardioversion take place concomitantly.

In some cases, the induction of cardioversion comprises applying an electric current to the patient. In some cases, the induction of cardioversion comprises administering an effective amount of an antiarrhythmic agent to the patient. In some cases, the antiarrhythmic agent comprises a Class Ic antiarrhythmic agent. In some cases, the antiarrhythmic agent comprises flecainide. In some cases, the administering the antiarrhythmic agent comprises administering the antiarrhythmic agent via intravenous, intramuscular, transdermal, oral, nasal delivery, or intranasal spray delivery. In some cases, the administering the antiarrhythmic agent comprises delivering the antiarrhythmic agent via intravenous (IV) infusion. In some cases, the administering the antiarrhythmic agent comprises delivering a Class Ia, Ib, Ic, II, III, IV, or V antiarrhythmic agent, or any combination thereof via IV injection and/or infusion. In some cases, the administering the antiarrhythmic agent comprises delivering vernakalant, flecainide, ibutilide, or defetilide via IV injection. In some cases, the effective amount of the antiarrhythmic agent is in a range of 1-50, 5-50, 10-50, or 5-25 mg.

Another aspect of the present disclosure provides a method, comprising: inducing cardioversion of atrial fibrillation in a patient in need thereof; and administering, by oral or nasal administration, an effective amount of a selective β1AR blocker to the patient, such that the selective β1AR first enters the heart through the pulmonary vein to the left atrium, thereby preventing or suppressing tachycardia, atrial ectopy, or both, associated with the cardioversion.

Another aspect of the present disclosure provides pharmaceutical formulation comprising selective β1AR blocker formulated for inhalation. In some cases, the pharmaceutical formulation further comprises an antiarrhythmic agent.

Another aspect of the present disclosure provides a kit, comprising: the pharmaceutical formulation provided herein, and instructions of use. In some cases, a kit comprises the pharmaceutical formulation as provided herein, a second pharmaceutical formulation comprising an antiarrhythmic agent, and instructions of use. In some cases, the kit further comprises an inhaler for administration of the pharmaceutical formulation.

Another aspect of the present disclosure relates to use of a selective β1AR antagonist, given via oral aerosol inhalation, or delivered via nasal inhalation or intranasal spray administration using an unit-dose or multi-dose spray to slow ventricular rate during episodes of atrial flutter or any type of atrial or junctional tachyarrhythmia that may arise in association with cardioversion of atrial fibrillation (AF) by any method of cardioversion such as pharmacological or electrical.

Another aspect of the present disclosure relates to use of a selective β1AR antagonist, given via oral inhalation, or delivered via nasal inhalation or intranasal spray administration using an unit-dose or multi-dose spray, in combination and concomitantly with a Class 1c antiarrhythmic agent, such as flecainide, given via oral inhalation, to prevent 1:1 AV nodal conduction in case of atrial flutter or any type of atrial or junctional tachyarrhythmia that may arise during cardioversion of AF. In some cases, the estimated lung dose (eTLD) of flecainide is between 5 and 250 mg. In some cases, the estimated $C_{max}$ flecainide in the heart is between 100-2000 ng/mL.

Another aspect of the present disclosure relates to use of a selective β1 adrenergic receptor (β1AR) antagonist, given via oral inhalation, or delivered via nasal inhalation or intranasal spray administration using an unit-dose aerosol 5 to 30 minutes prior to the administration of an antiarrhythmic agent given via IV infusion or via oral inhalation, to prevent 1:1 AV nodal conduction in case of atrial flutter or any type of atrial or junctional tachyarrhythmia that may arise during the cardioversion of AF. In some cases, the antiarrhythmic agent delivered via IV is Class I through V.

Another aspect of the present disclosure relates to use of a selective β1 adrenergic receptor (β1AR) antagonist, given via oral inhalation, or delivered via nasal inhalation or intranasal spray administration using an unit-dose aerosol given in combination, either concomitantly or sequentially, first at 5 to 30 minutes prior to the administration of an antiarrhythmic agent, given via IV infusion or via oral inhalation, to increase the efficacy of the antiarrhythmic agent to convert AF into normal sinus rhythm (NSR) and prevent the occurrence of 1:1 AV nodal conduction in case of atrial flutter or any other type of atrial or junctional tachyarrhythmia that may arise in the course of conversion of AF to NSR.

Another aspect of the present disclosure relates to use of a selective β1 adrenergic receptor (β1AR) antagonist, given via oral inhalation, or delivered via nasal inhalation or intranasal spray administration using a unit-dose aerosol 5 to 30 minutes prior to administration of an antiarrhythmic agent given via IV infusion or via oral inhalation, to prevent the recurrence of AF following its conversion to NSR.

Another aspect of the present disclosure relates to use of a single pharmaceutical solution consisting of an antiarrhythmic agent and a β1AR antagonist in certain concentration and proportion, to be administered to a patient with AF with the intent to convert the AF to NSR and to simultaneous slow conduction through the AV node, reduce ventricular rate, prevent recurrences of AF. In some case, the concentration of the antiarrhythmic agent is 10-50 mg/mL. In some cases, the dose of the β1AR is in the range of 1 to 10,000 μg.

Another aspect of the present disclosure relates to use of a dual-chamber oral inhalation or nasal spray device delivering a first pharmaceutical solution comprising an antiarrhythmic agent and a second pharmaceutical solution comprising a β1AR antagonist sequentially or simultaneously.

Another aspect of the present disclosure relates to use of β1AR antagonist (e.g., Nebivolol or its d-enantiomer), given via oral inhalation, or delivered via nasal inhalation or intranasal unit-dose or multi-dose spray administration, concomitantly or sequentially with flecainide to achieve the goals stated above without causing significant systemic hypotension and/or depression of ventricular contractility, that is, reduction of left ventricular function.

Another aspect of the present disclosure relates to a method to deliver β1AR antagonist (e.g., Nebivolol or its d-enantiomer) via oral inhalation route or intranasal routes using a liquid inhalation kit, using an unit-dose spray to be used alone or in combination, concomitantly or sequential applicable to all above claims to achieve restoration of NSR and slow ventricular rate (e.g., achieve rate control).

Another aspect of the present disclosure relates to a method to deliver Nebivolol or its d-enantiomer via oral inhalation using a dry powder inhalation kit, using an unit-dose spray to be used alone or in combination, concomitantly or sequential applicable to all above claims to achieve restoration of NSR and slow ventricular rate (e.g., achieve rate control).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
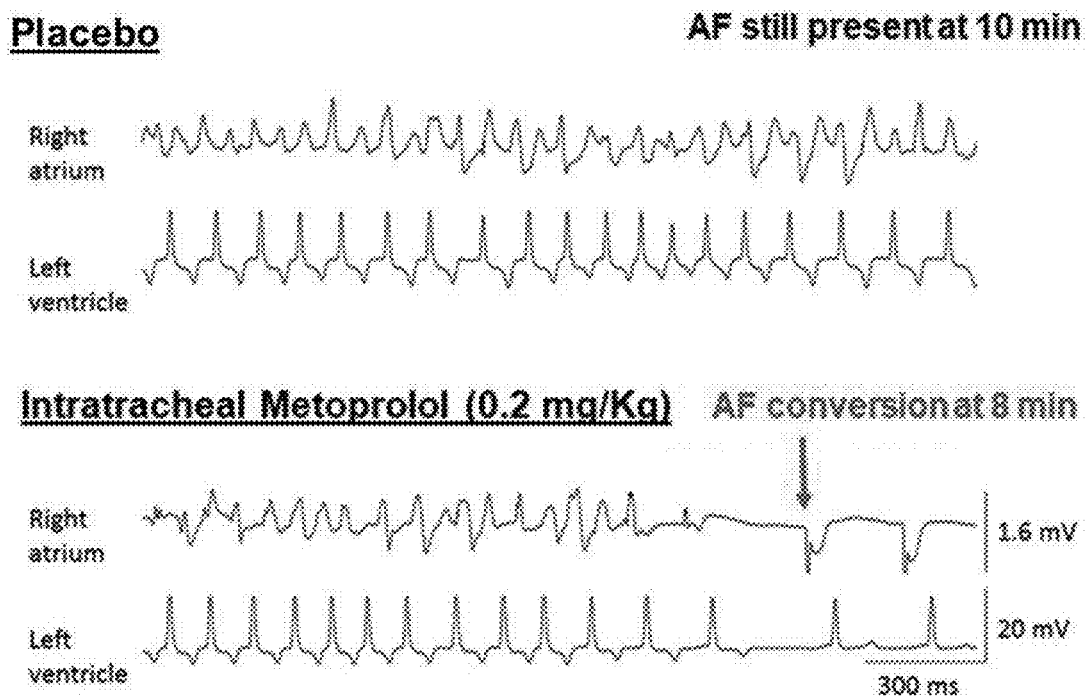
FIG. 1 shows representative electrocardiography (ECG) traces illustrating acceleration of conversion of AF by intratracheal administration of metoprolol.

As an overview, the present disclosure relates to administration of a β1AR blocker via inhalation to treat a heart condition (e.g., cardiac arrhythmia) in a subject in need thereof. The methods can include administering a therapeutically effective amount of β1AR blocker via inhalation to the subject. In some cases, the methods include administering via inhalation both a therapeutically effective amount of β1AR blocker and a therapeutically effective amount of class I antiarrhythmic agent.

Currently, β1AR blockers are delivered as IV and/or as oral tablets. These delivery routes can be not ideal for acute out-of-hospital treatment. In contrast, administration of β1AR blocker via inhalation, e.g., oral inhalation, nasal inhalation, or intranasal spray administration, can offer methods for quick and selective inhibition of β1ARs. For instance, administration via oral inhalation can provide a rapid delivery of the drug and protection that cannot be achieved with conventional dosage forms (e.g., tablets or pills) in an out-of-hospital setting. The nasal route or the intranasal spray route of administration can also offer a rapid delivery of the drug (e.g., β1AR blocker) into the systemic circulation to reach the heart faster than the oral administration (e.g., tablets or pills). Inhalation is one of the shortest routes for a drug to reach the heart. Inhalation of β1AR blockers can be used to overcome the shortcoming of other routes of administration and to prevent or treat heart conditions, such as atrial flutter with 1:1 AV conduction, atrial tachyarrythmias, and atrial ectopy.

One aspect of the present disclosure provides methods, compositions, unit doses, and kits for treating a heart condition, e.g., cardiac arrhythmias. The methods can include administering a therapeutically effective amount of a β1-selective adrenergic receptor blocker (β1AR blocker) via inhalation (e.g., oral inhalation, nasal inhalation, or intranasal spray administration) to a subject in need thereof (e.g., experiencing atrial arrhythmia).

β1AR blockers administered via inhalation, according to the present disclosure, can have significant therapeutic effects for treatment of cardiac arrhythmias, e.g., atrial arrhythmia. As described herein, cardioversion can refer to a process by which cardiac arrhythmia (e.g., atrial or ventricular arrhythmia, e.g., tachycardia, e.g., atrial fibrillation) is converted to a normal rhythm. In some cases, inhalatory administration of β1AR blockers also has ventricular rate control effects during the cardioversion for instance, slowing atrioventricular (AV) node conduction. In other words, inhalation administration of β1AR blocker provided herein can induce slowdown of AV node conduction and cardioversion at the same time.

One aspect of the present disclosure relates to a combination inhalatory therapy for treating a heart condition, e.g., cardiac arrhythmia, e.g., atrial arrhythmia. The methods can include administering to a subject in need thereof a therapeutically effective amount of β1AR blocker and a therapeutically effective amount of class I antiarrhythmic agent via inhalation. In some cases, the methods provided herein include administering to a subject experience cardiac arrhythmia, e.g., atrial arrhythmia, via inhalation a β1AR blocker and a class I antiarrhythmic agent. The methods can include administration of both the β1AR blocker and the class I antiarrhythmic agent via inhalation to the same subject. In some cases, the β1AR blocker and the class I antiarrhythmic agent are administered via inhalation concurrently. In some cases, the β1AR blocker is administered via inhalation prior to class I antiarrhythmic agent.

One beneficial effect of delivery of both β1AR blocker and class I antiarrhythmic agent to the same subject, according to some examples of the present disclosure, can be induction of both cardioversion and ventricular rate control. Without wishing to be bound by a particular theory, administration of a therapeutically effective amount of class I antiarrhythmic agent can induce cardioversion, which can reduce ventricular rate by restoring the normal sinus rhythm. On the other hand, administration of a therapeutically effective amount of β1AR blocker can slow AV node conduction, and optionally also contribute to cardioversion, which can further reduce the ventricular rate.

One readout of AV node conduction can be PR interval as read from electrocardiograph (ECG). The PR interval can refer to a measure of the period, e.g., in millisecond (msec), elapsed between atrial depolarization/activation (P Wave of ECG) to the beginning of ventricular depolarization/activation (QRS complex of ECG). The length of the PR interval can be determined by the electrical impulse across the atrial tissue, AV node, His-Purkinje system and beginning of ventricular myocardium activation. The PR interval can be equal to the sum of the A-H (actual to His-bundle) and H-V (His-bundle to ventricle) interval, ie., $PR=(A-H)+(H-V)$. A long PR interval can suggest slow conduction in any of the tissues, from atria to AV node His-Purkinje, traveled by the electrical impulse. In some cases of the present disclosure, the PR interval can be increased by the therapy provided herein. For instance, administration of a therapeutically effective amount of β1AR blocker via inhalation or intranasal spray administration can prolong PR interval as measured by ECG, e.g., for at least about 2%, 3%, 4%, 5%, 6%, 8%, or 10%, or for about 2%, 3%, 4%, 5%, 6%, 8%, or 10%. In other cases, administration of a therapeutically effective amount of β1AR blocker and a therapeutically effective amount of class I antiarrhythmic agent can prolong PR interval as measured by ECG, e.g., for at least about 2%, 3%, 4%, 5%, 6%, 8%, or 10%, or for about 2%, 3%, 4%, 5%, 6%, 8%, or 10%.

Rate control can have important value for treatment of cardiac arrhythmias, e.g., atrial arrhythmia. Atrial fibrillation, for example, can have important haemodynamic and symptomatic consequences. During atrial fibrillation, the atria can fail to eject blood properly and not contribute to the stroke volume, reducing cardiac output by 20-30% or more. The irregular and usually fast ventricular rate can further reduce ventricular filling and stroke volume. Both the rhythm irregularity and the reduced stroke volume can cause symptoms and contribute to the development or worsening of heart failure. The reduction in stroke volume can become even more substantial at faster heart rates. Reduced cardiac output can be exacerbated in patients with heart failure who have preserved or reduced left ventricular ejection fractions and can cause substantial clinical deterioration. Persistent rapid rates can also worsen or even cause a tachycardia-induced cardiomyopathy. In some cases, during cardioversion, there can be severe conditions occurring due to loss of rate control, e.g., rapid atrial or ventricular rate.

As discussed above, delivery of class I antiarrhythmic agent can be associated with risk of inducing atrial flutter during cardioversion, e.g., cardioversion from atrial fibrillation to normal sinus rhythm. Life threatening condition, such as haemodynamic instability and ventricular fibrillation, can be induced if atrial flutter emerges in conjunction with 1:1 AV node conduction rate, as very fast ventricular rate (e.g., ventricular tachycardia) can arise. The methods, compositions, and kits provided herein that relate to providing a cardio-protection prior to cardioversion using a class I antiarrhythmic agent, e.g., class Ia, Ib, or Ic antiarrhythmic drug. Administration of both β1AR blocker to and class I antiarrhythmic agent via inhalation can prevent prophylactically the occurrence of atrial flutter with 1:1 AV node conduction, by slowing the AV node conduction during the cardioversion. As a result, the methods, compositions, and kits of the present disclosure can offer a safe therapeutic strategy.

The lung is the shortest route for drug to heart with minimal dilution next to intra-cardiac injection. Drugs delivered via the lung can have a fast onset action compared to those delivered via the oral route. Pipeline Insights: Antiarrhythmics, Datamonitor (June 2006). Pulmonary drug delivery to the heart is at least equivalent to a portable intravenous injection. The present disclosure involves a rapid acting inhaled product with a fast onset of action as compared to oral medicine. The product is expected to be at least as fast as intravenous medicine or act faster than intravenous medicine. In some cases, an amount of the β1AR blocker, class I antiarrhythmic agent, or both peaks in the coronary circulation of the heart at a time ranging from 10 seconds to 30 minutes, such as 30 seconds to 20 minutes, 1 minute to 10 minutes, 2 minutes to 8 minutes, or 2.5 minutes to 5 minutes, after the administration. An electrophysiologic effect of the administered drug can be observed, e.g., via electrocardiography, at a time ranging from 10 seconds to 30 minutes, such as 30 seconds to 20 minutes, 1 minute to 10 minutes, 2 minutes to 8 minutes, or 2.5 minutes to 5 minutes, after the administration. In some cases, a cardiac score from a device with an arrhythmia detection algorithm shows a transition from an arrhythmic state to normal sinus rhythm in the patient at a time ranging from 10 seconds to 30 minutes, such as 30 seconds to 20 minutes, 1 minute to 10 minutes, 2 minutes to 8 minutes, or 2.5 minutes to 5 minutes, after the administration. In some cases, a short form-36 quality of life score of the patient improves at a time ranging from 10 seconds to 30 minutes, such as 30 seconds to 20 minutes, 1 minute to 10 minutes, 2 minutes to 8 minutes, or 2.5 minutes to 5 minutes, after the administration. In some examples, the patient has normal sinus rhythm within 30 minutes, such as within 10 minutes, after the administration.

A peak concentration of the pharmaceutical agents can be seen early in time after its delivery according to the present disclosure. In some cases, a concentration of the β1AR blocker in the coronary arterial circulation of the heart is between about 0.001 mg/L and about 0.1 mg/L, about 0.001 mg/L and about 0.09 mg/L, about 0.001 mg/L and about 0.08 mg/L, about 0.001 mg/L and about 0.07 mg/L, about 0.001 mg/L and about 0.06 mg/L, about 0.001 mg/L and about 0.05 mg/L, about 0.001 mg/L and about 0.04 mg/L, about 0.001 mg/L and about 0.03 mg/L, about 0.001 mg/L and about 0.02 mg/L, about 0.001 mg/L and about 0.01 mg/L, about 0.001 mg/L and about 0.009 mg/L, about 0.001 mg/L and about 0.008 mg/L, about 0.001 mg/L and about 0.007 mg/L, about 0.001 mg/L and about 0.006 mg/L, about 0.001 mg/L and about 0.005 mg/L, about 0.001 mg/L and about 0.004 mg/L, about 0.001 mg/L and about 0.003 mg/L, about 0.001 mg/L and about 0.002 mg/L, about 0.002 mg/L and about 0.1 mg/L, about 0.005 mg/L and about 0.1 mg/L, about 0.01 mg/L and about 0.1 mg/L, about 0.02 mg/L and about 0.1 mg/L, about 0.03 mg/L and about 0.1 mg/L, about 0.04 mg/L and about 0.1 mg/L, about 0.05 mg/L and about 0.1 mg/L, about 0.06 mg/L and about 0.1 mg/L, about 0.07 mg/L and about 0.1 mg/L, about 0.08 mg/L and about 0.1 mg/L, about 0.09 mg/L and about 0.1 mg/L, about 0.01 mg/L and about 0.1 mg/L, about 0.01 mg/L and about 0.09 mg/L, about 0.01 mg/L and about 0.08 mg/L, about 0.01 mg/L and about 0.07 mg/L, about 0.01 mg/L and about 0.06 mg/L, about 0.01 mg/L and about 0.05 mg/L, about 0.01 mg/L and about 0.04 mg/L, about 0.01 mg/L and about 0.03 mg/L, about 0.01 mg/L and about 0.02 mg/L, about 0.03 mg/L and about 0.09 mg/L, about 0.05 mg/L and about 0.09 mg/L, or about 0.05 mg/L and about 0.08 mg/L at 2.5 minutes after the administering. In some cases, a concentration of the β1AR in the coronary arterial circulation of the heart is between about 0.01 mg/L and about 0.1 mg/L at 2.5 minutes after the administration.

In some cases, the peak concentration of the β1AR blocker in the coronary arterial circulation of the heart peaks at between about 0.001 mg/L and about 0.1 mg/L, such as, between about 0.001 mg/L and about 0.1 mg/L, about 0.001 mg/L and about 0.09 mg/L, about 0.001 mg/L and about 0.08 mg/L, about 0.001 mg/L and about 0.07 mg/L, about 0.001 mg/L and about 0.06 mg/L, about 0.001 mg/L and about 0.05 mg/L, about 0.001 mg/L and about 0.04 mg/L, about 0.001 mg/L and about 0.03 mg/L, about 0.001 mg/L and about 0.02 mg/L, about 0.001 mg/L and about 0.01 mg/L, about 0.001 mg/L and about 0.009 mg/L, about 0.001 mg/L and about 0.008 mg/L, about 0.001 mg/L and about 0.007 mg/L, about 0.001 mg/L and about 0.006 mg/L, about 0.001 mg/L and about 0.005 mg/L, about 0.001 mg/L and about 0.004 mg/L, about 0.001 mg/L and about 0.003 mg/L, about 0.001 mg/L and about 0.002 mg/L, about 0.002 mg/L and about 0.1 mg/L, about 0.005 mg/L and about 0.1 mg/L, about 0.01 mg/L and about 0.1 mg/L, about 0.02 mg/L and about 0.1 mg/L, about 0.03 mg/L and about 0.1 mg/L, about 0.04 mg/L and about 0.1 mg/L, about 0.05 mg/L and about 0.1 mg/L, about 0.06 mg/L and about 0.1 mg/L, about 0.07 mg/L and about 0.1 mg/L, about 0.08 mg/L and about 0.1 mg/L, about 0.09 mg/L and about 0.1 mg/L, about 0.01 mg/L and about 0.1 mg/L, about 0.01 mg/L and about 0.09 mg/L, about 0.01 mg/L and about 0.08 mg/L, about 0.01 mg/L and about 0.07 mg/L, about 0.01 mg/L and about 0.06 mg/L, about 0.01 mg/L and about 0.05 mg/L, about 0.01 mg/L and about 0.04 mg/L, about 0.01 mg/L and about 0.03 mg/L, about 0.01 mg/L and about 0.02 mg/L, about 0.03 mg/L and about 0.09 mg/L, about 0.05 mg/L and about 0.09 mg/L, or about 0.05 mg/L and about 0.08 mg/L. In some cases, the peak concentration of the β1AR blocker in the coronary arterial circulation of the heart peaks at between about 0.01 mg/L and about 0.1 mg/L In some instances, the present disclosure involves low doses that are safe and effective. Without wishing to be bound by a particular theory, administration of drugs via the lung, e.g., via inhalation, e.g., oral inhalation, nasal inhalation, or intranasal spray administration, can benefit from the large 100 m² surface area of the alveoli, which can avidly absorb fluid. The advantageous features of pulmonary delivery can be a rapid, transient peak in drug concentration in the pulmonary venous circulation, with abrupt transfer to the left atrial chamber and thereafter to the coronary arteries through the rich capillary network. The net effect can be efficient transfer of the antiarrhythmic agents, e.g., β1AR blocker or class I antiarrhythmic agent, to the atrial myocardium and critical arrhythmogenic structures including pulmonary vein sleeves. With inhaled cardiotherapy the drug is directed to the heart from the lungs as a bolus. The heart can experience a transient, high concentration of the active drug, e.g., β1AR blocker, class I antiarrhythmic agent, or both. The drug can be rapidly diluted as it passes through the heart, but the exposure time can be sufficient for the desired pharmacological action. Once the drug passes through the heart, the concentration of the drug in the systemic circulation (e.g., peripheral venous blood) can be below the therapeutic concentration and is considered ineffective. The therapeutic window can be in the range of dosage of a drug or of its concentration in a bodily system that provides safe effective therapy. Anything below the minimum amount is sub-therapeutic and hence ineffective in that concentration. In view of the dilution, unwanted side effects can be minimized.

In some cases, inhalation avoids metabolism, such as hepatic metabolism. Inhalation can also avoid red blood cell metabolism. For instance, the reduced dilution and short route associated with inhalation reduces red blood cell metabolism of esmolol. Inhalation can also avoid reduced blood pressure and fainting. For instance, IV administration of beta blockers, such as esmolol, can reduce mean arterial blood pressure (MAP). Inhalation can allow rapid delivery of esmolol without reducing MAP. As a result, inhalation of beta blockers can result in an MAP of 10 mm Hg to 20 mm Hg greater than the MAP resulting from IV administration of the same beta blocker. Inhalation can also allow mitigation of inotropic effect of the β1AR blocker by using it at a dose that is below the threshold of eliciting the inotropic actions. As a result, the methods provided herein can cause little to no reduction in ventricular contractility in the subject. In some cases, the reduction in the ventricular contractility, e.g., left ventricular contractility, is at most about 10%, at most about 5%, at most about 3%, at most about 2%, at most about 1%. In some cases, the reduction in the ventricular contractility, e.g., left ventricular contractility, is no more than 1%.

The methods, compositions, and kits provided herein, for instance, involving inhalation of β1AR blocker, or both β1AR blocker and class I antiarrhythmic agent, can induce cardioversion within a short time window, e.g., within 40 minutes, 30 minutes, 25 minutes, 20 minutes, 15 minutes, 10 minutes, or 5 minutes. In some cases, the methods, compositions, and kits provided herein reduces ventricular rate, e.g., average ventricular rate, during the cardioversion by at least about 10%, 12%, 15%, 17.%, or 20%. Ventricular rate can be resting ventricular rate as measured by electrocardiography (ECG) when the subject remain at resting state (resting ventricular rate) or when the subject is performing moderate exercise. In some cases, lenient rate control is achieved by the methods provided herein, e.g., the ventricular rate, e.g., average ventricular rate, is reduced to below 110 beats per minute (bpm) at resting state. In some cases, strict rate control is achieved by the methods provided herein, e.g., the ventricular rate, e.g., average ventricular rate, is reduced to below 80 bpm at resting state, below 110 bpm during moderate exercise, or both. Ventricular rate reduction that can be achieved according to some cases of the present disclosure can occur within from 10 seconds to 60 minutes, from 10 seconds to 45 minutes, from 10 seconds to 40 minutes, from 10 seconds to 30 minutes, such as 30 seconds to 20 minutes, 1 minute to 10 minutes, 2 minutes to 8 minutes, or 2.5 minutes to 5 minutes, after the administration. In some cases, the ventricular rate can be reduced to below 110 bpm (e.g., resting ventricular rate or moderate exercise ventricular rate) or below 80 bpm within from 10 seconds to 60 minutes, from 10 seconds to 45 minutes, from 10 seconds to 40 minutes, from 10 seconds to 30 minutes, such as 30 seconds to 20 minutes, 1 minute to 10 minutes, 2 minutes to 8 minutes, or 2.5 minutes to 5 minutes, after the administration.

One aspect of the present disclosure relates to the beneficial synergistic effects of the co-administration of β1AR blocker and class I antiarrhythmic agent via inhalation to a subject in need thereof for the treatment of a heart condition, e.g., cardiac arrhythmia, e.g., atrial arrhythmia. In some cases, inhalation of a first therapeutically effective amount of a β1AR blocker and a second therapeutically effective amount of a class I antiarrhythmic has significantly greater therapeutic effects as compared to administration of the first amount of the β1AR blocker or the second amount of the class I antiarrhythmic agent alone. Such greater therapeutic effects can include faster cardioversion, e.g., acute conversion of the arrhythmia the subject is suffering from to normal sinus rhythm in a shorter time period. In other cases, the greater therapeutic effects include a better ventricular rate control, for instance, the ventricular rate can be reduced to a relatively lower level, can be reduced to a low level in a shorter time window, or can be better maintained at a relatively low and normal level (e.g., with less fluctuation, with fewer incidences of heart overbeating). The greater therapeutic effects can also include therapeutic effects not observed when only one drug is administered to the subject.

In some cases, the combination therapy as described herein can have greater therapeutic effects as compared to a simple arithmetic sum of administration of the β1AR blocker and class I antiarrhythmic agent alone without the other. For instance, in the combination therapy according to the present disclosure, the β1AR blocker and the class I antiarrhythmic agent can be both administered at their respective minimum effective dose, while the therapeutic effect of the combinatory administration is greater than the therapeutic effects of administering either the β1AR blocker or the class I antiarrhythmic agent alone at a dose twice of their respective minimum effective dose. In other examples, in the combination therapy according to the present disclosure, the β1AR blocker and the class I antiarrhythmic agent can be both administered at a dose one half of their respective minimum effective dose, while the therapeutic effect of the combinatory administration is greater than the minimum therapeutic effect if either drug is administered alone to the subject.

In some cases, the beneficial effects conveyed by the combination therapy of co-administration render the minimum effective dose of the β1AR blocker, the class I antiarrhythmic agent, or both significantly lower than the minimum effective dose of either the β1AR blocker or the class I antiarrhythmic agent alone without the other agent. For instance, in some cases, the β1AR blocker, the class I antiarrhythmic agent, or both, can be used in a subthreshold dose, which can mean a dose at which the drug is not therapeutically effective if it is administered alone without the other agent. As an example, a minimum therapeutically effective dose of flecainide acetate for treating atrial arrhythmia can be 30 mg in an adult human subject, while the dose needed for flecainide acetate in the combination therapy as described herein, when being used together with a β1AR blocker, can be lower than 30 mg in the same adult human subject, such as, 25 mg, 20 mg, or 15 mg. The same can apply to the dose of the β1AR blocker as used in the combination therapy. As a result of the beneficial synergistic effects of the combination therapy according to some embodiments, the present disclosure can offer an even lower and safer dose of drug use as compared to conventional therapy. Accordingly, lower or little side effects of the drug use can be seen when practicing the combination inhalatory therapy provided herein. On the other hand, at least equivalent or even better therapeutic effects in terms of cardiac rhythm control and ventricular rate control can be achieved.

One aspect of the present disclosure relates to delivery of β1AR blocker by inhalation to patient in need thereof, e.g., patient with a heart condition, e.g., patient with AF, or patient with tachycardia, e.g. patient with atrial flutter. In some cases, the present disclosure relates to delivery of a third generation β1AR blockers, e.g., nebivolol, or salts thereof, nebivolol salts by oral or nasal administration to patients in need thereof, e.g., patients with tachycardia, e.g., patients with AF or atrial flutter. In some cases, the present disclosure relates to treating tachycardia, e.g., atrial flutter by delivery of β1AR blocker via inhalation. In some cases, the present disclosure relates to preventing tachycardia, e.g., atrial flutter by delivery of β1AR blocker via inhalation. In some cases, delivery of β1AR blocker according to the present disclosure can facilitate both prevention and treatment of tachycardia, e.g., atrial flutter. In some cases, the present disclosure relates to the use of the d-enantiomer of nebivolol for this purpose.

In some cases, oral or nasal administration of β1AR blocker, e.g., third generation β1AR blocker, e.g., nebivolol, can meet most, if not all, requirements of an ideal rate-control therapy. It can be easily and safely administered to patients as a rate-control therapy in the hospital or self-administered by patients at home. In some cases, it is safe and well tolerated. It can have fast onset to effect through these routes of administration. The drug delivered according to the present disclosure can also exhibit a long duration of effect, e.g., for several hours, after a single or repeated administration.

Another aspect of the present disclosure relates to delivery of β1AR blocker via oral or nasal administration, in combination with therapies for cardioversion in patient in need thereof, e.g., patient with AF. In some cases, an antiarrhythmic agent can be used to convert AF, and inhaled β1AR blockers can reduce the occurrence of a potentially dangerous atrial flutter, for instance, atrial flutter with 1:1 AV nodal conduction. In some cases, orally inhaled, nasally administered, or intranasally spray administered β1AR blockers can also reduce atrial ectopy (premature atrial contractions PACs) caused by triggering afterpotentials and therefore can reduce the recurrence rate of AF post cardioversion associated with the use of antiarrhythmic therapies because these events (afterpotentials) are in great part mediated by high sympathetic tone.

Another aspect of the present disclosure relates to administering β1AR blocker, e.g., third generation β1AR blocker, e.g., nebivolol or its d-enantiomer, via inhalation for the management of patient with a recent episode of PAF. Administration of β1AR blocker in patients with recent episode of PAF according to the present disclosure can have the benefit of (a) slowing ventricular rate and hence mitigating symptoms, (b) reducing the likelihood of fast ventricular rate during atrial flutter, (c) reducing recurrence of AF post cardioversion, or (d) any combination thereof. The drug can be quickly and easily delivered in a manner that is safe, well tolerated, has fast onset of action, and/or exhibits a long duration of effect, e.g., for several hours, after a single or repeat administration, for in- and out-of-hospital.

As used herein, "heart condition" can refer to a condition where heart has an abnormal function and/or structure, for example, heart is beating in an irregular rhythm, experiencing arrhythmia, atrial fibrillation, and/or tachycardia, there is myocardial infarction, and/or coronary heart disease. As used herein, "atrial arrhythmia" can refer to an arrhythmia that affects at least one atrium and does not include bradycardia. For instance, atrial arrhythmia may originate in and affect at least one atrium. As used herein, "tachycardia" can refer to an arrhythmia in which the heart beat is too fast. For instance, tachycardia may involve a resting heart rate of over 100 beats per minute, such as greater than 110, greater than 120, or greater than 130 beats minute. In some cases, tachycardia can comprise sinus tachycardia, atrial fibrillation, atrial flutter, AV nodal reentrant tachycardia, accessory pathway mediated tachycardia, atrial tachycardia, multifocal atrial tachycardia, junctional tachycardia, ventricular tachycardia, supraventricular tachycardia, or any combination thereof.

As used herein, the phrase "heart rhythm arrhythmia" can refer to an arrhythmia in which the heart beat is irregular. As used herein, the term "atrial fibrillation" can refer to an abnormal heart rhythm characterized by rapid and irregular beating of the atria. As used herein, the term "cardioversion" can refer to a process by which an abnormally fast heart rate (tachycardia) or other cardiac arrhythmia is converted to a normal sinus rhythm. Cardioversion can be induced by electricity, drugs, or both.

As used herein, the singular forms "a," "an," and "the" can include plural referents unless the context clearly dictates otherwise. Thus, for example, reference to "an antiarrhythmic agent" can include not only a single active agent but also a combination or mixture of two or more different active agents.

Reference herein to "one embodiment," "one version," or "one aspect" can include one or more such embodiments, versions or aspects, unless otherwise clear from the context.

As used herein, the term "pharmaceutically acceptable solvate" can refer to a solvate that retains one or more of the biological activities and/or properties of the antiarrhythmic pharmaceutical agent and that is not biologically or otherwise undesirable. Examples of pharmaceutically acceptable solvates include, but are not limited to, antiarrhythmic pharmaceutical agents in combination with water, isopropanol, ethanol, methanol, DMSO, ethyl acetate, acetic acid, ethanolamine, or combinations thereof.

As used herein, the term "pharmaceutically acceptable salt" can refer to those salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, di nitrobenzoates, hydroxybenzoates, methoxybenzoates, phthalates, sulfonates, xylenesulfonates, phenylacetates, phenyipropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

As used herein, "atrial arrhythmia" can refer to an arrhythmia that affects at least one atrium and does not include bradycardia. For instance, atrial arrhythmia can originate in and affect at least one atrium.

As used herein, "tachycardia" can mean an arrhythmia in which the heart beat is too fast, e.g., faster than normal. For instance, tachycardia may involve a resting heart rate of over 100 beats per minute, such as greater than 110, greater than 120, or greater than 130 beats minute.

As used herein, the phrase "heart rhythm arrhythmia" can refer to an arrhythmia in which the heart beat is irregular.

As used herein, the amount of an agent as described herein in the coronary circulation of the heart" can be measured by extracting a sample from any vascular region of the coronary circulation of the heart (e.g., arteries, veins, including coronary sinus) by using a cannula. The amount of the agent in the sample can then be determined by known means, such as bioanalytical techniques that employ analytical equipment such as LC-MS/MS. Thus, the amount of the agent in the blood in the heart can be measured for any particular time.

As used herein, the terms "treating" and "treatment" can refer to reduction in severity and/or frequency of symptoms, elimination of symptoms and/or underlying cause, reduction in likelihood of the occurrence of symptoms and/or underlying cause, and/or remediation of damage. Thus, "treating" a patient with an active agent as provided herein can include prevention of a particular condition, disease, or disorder in a susceptible individual as well as treatment of a clinically symptomatic individual.

As used herein, "nominal amount" can refer to the amount contained within the unit dose receptacle(s) that are administered.

As used herein, "effective amount" can refer to an amount covering both therapeutically effective amounts and prophylactically effective amounts.

As used herein, a "therapeutically effective amount" of an active agent can refer to an amount that is effective to achieve a desired therapeutic result. A therapeutically effective amount of a given active agent can vary with respect to factors such as the type and severity of the disorder or disease being treated and the age, gender, and weight of the patient. In some cases, "inhalation" (e.g., "oral inhalation" or "nasal inhalation") refers to inhalation delivery of a therapeutically effective amount of a pharmaceutical agent contained in one unit dose receptacle, which, in some instance, can require one or more breaths, like 1, 2, 3, 4, 5, 6, 7, 8, 9, or more breaths. For example, if the effective amount is 90 mg, and each unit dose receptacle contains 30 mg, the delivery of the effective amount can require 3 inhalations.

Unless otherwise specified, the term "therapeutically effective amount" can include a "prophylactically effective amount," e.g., an amount of active agent that is effective to prevent the onset or recurrence of a particular condition, disease, or disorder in a susceptible individual.

As used herein, the phrase "minimum effective amount" can mean the minimum amount of a pharmaceutical agent necessary to achieve an effective amount.

As used herein, "mass median diameter" or "MMD" can refer to the median diameter of a plurality of particles, typically in a polydisperse particle population, e.g., consisting of a range of particle sizes. MMD values as reported herein are determined by laser diffraction (Sympatec Helos, Clausthal-Zellerfeld, Germany), unless the context indicates otherwise. For instance, for powders the samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, "geometric diameter" can refer to the diameter of a single particle, as determined by microscopy, unless the context indicates otherwise.

As used herein, "mass median aerodynamic diameter" or "MMAD" can refer to the median aerodynamic size of a plurality of particles or particles, typically in a polydisperse population. The "aerodynamic diameter" can be the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. As used herein, MMAD refers to the median of the aerodynamic particle or particle size distribution of aerosolized particles determined by cascade impaction, unless the context indicates otherwise.

By a "pharmaceutically acceptable" component is meant a component that is not biologically or otherwise undesirable, e.g., the component may be incorporated into a pharmaceutical formulation of the invention and administered to a patient as described herein without causing any significant undesirable biological effects or interacting in a deleterious manner with any of the other components of the formulation in which it is contained. When the term "pharmaceutically acceptable" is used to refer to an excipient, it can imply that the component has met the required standards of toxicological and manufacturing testing or that it is included on the Inactive Ingredient Guide prepared by the U.S. Food and Drug Administration.

As used herein, "P wave" can represent the wave generated by the electrical depolarization of the atria (right and left), and is usually 0.08 to 0.1 seconds (80-100 ms) in duration.

Beta Blockers and Antiarrhythmic Agents

β1AR blockers that can be used in the methods, compositions and kits provided herein can include any molecule that has β1 adrenergic receptor-selective inhibitory effect. There are different types of adrenergic receptors, including α1, α2, β1, β2, and β3 receptors. Exemplary effects of activation of β1 adrenergic receptors can include increasing cardiac output by increasing heart rate (positive chronotropic effect), increasing conduction velocity (positive dromotropic effect), increasing stroke volume by enhancing contractility (positive inotropic effect), and increasing rate of relaxation of the myocardium by increasing calcium ion sequestration rate (positive lusitropic effect). β1 adrenergic receptor-selective blockers, or β1AR blockers, can include compounds or other molecules that selectively inhibit the activation of β1 adrenergic receptor, with substantially no impact on other subtypes of adrenergic receptors. β1AR blockers can also include compounds or other molecules that have higher inhibitory effect on β1 adrenergic receptor as compared to other subtypes of adrenergic receptors, such as α1, α2, β1, β2, and β3 receptors. In some cases, β1AR blockers provided herein have at least about 10%, about 20%, about 30%, about 40%, about 50%, about 60%, about 70%, about 80%, about 90%, about 100%, about 120%, about 150%, about 200%, about 250%, about 300%, about 400%, about 500%, about 750%, about 800%, about 900%, about 10 times, about 20 times, about 50 times, about 100 times, about 200 times, about 500 times, about 1000 times, about 2000 times, about 5000 times, about 10000 times, about $10^5$ times, about $10^6$ times, about $10^7$ times, or about $10^8$ times inhibitory effect on β1AR higher than on other subtypes of adrenergic receptors. The comparisons can be made based on the IC50, e.g., the concentration of an inhibitor where the response (or binding) is reduced by half.

β1AR blockers that can be used in the methods, compositions and kits provided herein include acebutolol, atenolol, betaxolol, bisoprolol, celiprolol, metoprolol, nebivolol, or esmolol, or a pharmaceutically acceptable salt or solvate thereof. In some cases, compounds that can have inhibitory effect on both β1 and β2 adrenergic receptors can be used in the methods, kits, and compositions, such as propranolol, bucindolol, carteolol, carvedilol, labetalol, nadolol, oxprenolol, penbutolol, pindolol, soltalol, or timolol, or a pharmaceutically acceptable salt or solvate thereof.

Metoprolol is a medication of the selective β1 receptor blocker type and can be used for the purpose of the present disclosure. Metoprolol is chemically, (±) 1-(isopropylamino)-3-[p-(2-methoxyethyl) phenoxy]-2-propanol.

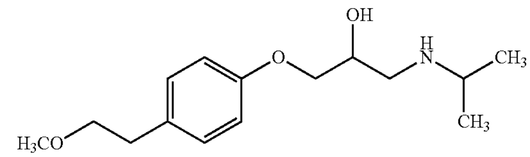 [SMILES: COCCc1ccc(OCC(O)CNC(C)C)cc1]

In some cases, metoprolol is used in the form of a pharmaceutically acceptable salt or solvate, for instance, metoprolol tartrate or metoprolol succinate. Metoprolol can be a racemic combination of its two enantiomers R and S.

Nebivolol is one of third generation selective β1 adrenergic receptor (β1AR) blocker. It is chemically, 2,2'-Azanediylbis(1-(6-fluorochroman-2-yl)ethanol). Nebivolol can have many advantageous features. Nebivolol may not exhibit a blockade effects; and can have nitric oxide-potentiating vasodilatory effect. In some instances, nebivolol has also been shown as β1AR-selective in experiments conducted on biopsied heart tissue. In some instances, nebivolol has been exhibit approximately 3.5 times more β1AR-selectivity than bisoprolol, another third generation selective β1AR blocker.

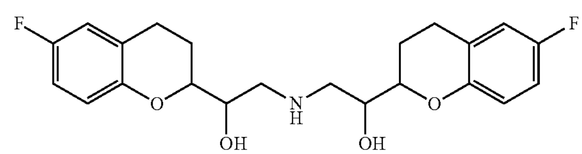 [SMILES: OC(CNCC(O)C1CCc2cc(F)ccc2O1)C1CCc2cc(F)ccc2O1]

Nebivolol can be a racemic combination of two enantiomers: d-nebivolol (+SRRR nebivolol) and 1-nebivolol (−RSSS nebivolol). The two enantiomers differ pharmacologically and therapeutically, with a noticeably different profile from that of conventional beta-blockers. In some instances, the selective blocking of β1 adrenoceptors is caused almost exclusively by d-nebivolol. The 1-nebivolol enantiomer can stimulate endothelial nitric oxide (NO) synthesis, thereby increasing the availability of NO in the endothelium, smooth muscle, and platelets and, consequently, causes a sustained vasodilation, with decreases in peripheral resistance and blood pressure.

In some cases, nebivolol as described herein can refer to nebivolol, any salts thereof, any derivatives thereof, or any combination thereof. Nebivolol can be a racemic combination consisting of two enantiomers, d-nebivolol (+SRRR nebivolol) and 1-nebivolol (−RSSS nebivolol). In some cases, the use of the d-enantiomer of nebivolol is highly preferred over the racemic dl-nebivolol mixture in this disclosure.

Because of the unique characteristics of this compound described herein, delivering nebivolol and, more preferably, d-nebivolol, directly to the heart via oral or nasal administration can have a fast onset to effect, leading to fast, effective and persistent rate control, due to slowing of AV nodal transmission. The oral or nasal administration of the third generation β1AR blocker, such as nebivolol, can meet most, if not all, the requirements of an ideal rate-control therapy for patients with AF.

Nebivolol's β1 selectivity can make this drug safe for oral or nasal administration as provided herein, e.g., oral inhalation, nasal inhalation, or intranasal spray administration, as it does not cause bronchospasm or peripheral vasoconstriction, when used through the inhalation route. In certain instances, other β1AR blockers which are not cardio-selective may cause these undesirable reactions.

Nebivolol can have a long half-life, ranging from 10.3 hours to 31.9 hours, depending on the patient's metabolism. Nebivolol can have a long-lasting effect.

When administered via oral or nasal administration as provided herein, e.g., oral inhalation, nasal inhalation, or intranasal spray administration, the drug can be rapidly absorbed through the lungs or nasal mucosa to quickly reach the heart, e.g., the atrial myocardium and AV node, for a fast onset of effect. This may result in a rapid reduction in AV nodal transmission, reduction in ventricular rate and/or, suppression of atrial ectopy.

In some cases, the use of the d-enantiomer of nebivolol is highly preferred over the racemic dl-nebivolol mixture. The selective blocking of β1 adrenoceptors can be determined by d-nebivolol. In some cases, d-enantiomer of nebivolol can be less likely than the racemic mixture of dl-nebivolol to cause undesirable hypotension.

Examples of antiarrhythmic pharmaceutical agents include, but are not limited to, class Ia (sodium channel blockers, intermediate association/dissociation), class Ib (sodium channel blockers, fast association/dissociation), class Ic (sodium channel blocker, slow association/dissociation), class II (beta blockers), class III (potassium channel blockers), class IV (calcium channel blockers), and class V (unknown mechanisms) antiarrhythmic agent.

Class Ia antiarrhythmic agent include, but are not limited to, quinidine, procainamide, and disopyramide. Class Ib antiarrhythmic agent include, but are not limited to, lidocaine, tocainide, phenyloin, moricizine, and mexiletine. Class Ic antiarrhythmic agent include, but are not limited to, flecainide, propafenone, and moricizine. Class II antiarrhythmic agent include, but are not limited to, propranolol, acebutolol, soltalol, esmolol, timolol, metoprolol, nebivolol, and atenolol. Class III antiarrhythmic agent include, but are not limited to, amiodarone, sotalol, bretylium, ibutilide, E-4031 (methanesulfonamide), vernakalant, and dofetilide. Class IV antiarrhythmic agent include, but are not limited to, bepridil, nitrendipine, amlodipine, isradipine, nifedipine, nicardipine, verapamil, and diltiazem. Class V antiarrhythmic agent include, but are not limited to, digoxin and adenosine.

β1AR blocker provided herein can be concomitantly or sequentially administered by oral inhalation with a Class Ic antiarrhythmic agent, e.g., flecainide. The flecainide can be administered in a range of 10-250 mg.

The present disclosure also includes derivatives of the above β1AR blocker and/or antiarrhythmic pharmaceutical agents such as solvates, salts, solvated salts, esters, amides, hydrazides, N-alkyls, and/or N-amino acyls. Examples of ester derivatives include, but are not limited to, methyl esters, choline esters, and dimethylaminopropyl esters. Examples of amide derivatives include, but are not limited to, primary, secondary, and tertiary amides. Examples of hydrazide derivatives include, but are not limited to, N-methylpiperazine hydrazides. Examples of N-alkyl derivatives include, but are not limited to, N',N',N'-trimethyl and N',N'-dimethylaminopropyl succininimidyl derivatives of antiarrhythmic pharmaceutical agent methyl esters. Examples of N-aminoacyl derivatives include, but are not limited to, N-ornithyl-, N-diaminopropionyl-, N-lysil-, N-hexamethyllysil-, and N-piperidine-propionyl- or N',N'-methyl-1-piperazine-propionyl-antiarrhythmic pharmaceutical agent methyl esters.

The β1AR blocker and/or antiarrhythmic pharmaceutical agents may exist as single stereoisomers, racemates, and/or mixtures of enantiomers, and/or diastereomers. All such single stereoisomers, racemates, and mixtures thereof are intended to be within the scope of the present disclosure. These various forms of the compounds may be isolated/prepared by methods known in the art.

The β1AR blocker and/or antiarrhythmic pharmaceutical agents of the present disclosure may be prepared in a racemic mixture (i.e., mixture of isomers) that contains more than 50%, preferably at least 75%, and more preferably at least 90% of the desired isomer (i.e., 80% enantiomeric or diastereomeric excess). According to particularly preferred embodiments, the compounds of the present disclosure are prepared in a form that contains at least 95% (90% e.e. or d.e.), even more preferably at least 97.5% (95% e.e. or d.e.), and most preferably at least 99% (98% e.e. or d.e.) of the desired isomer. Compounds identified herein as single stereoisomers are meant to describe compounds used in a form that contains more than 50% of a single isomer. By using known techniques, these compounds may be isolated in any of such forms by slightly varying the method of purification and/or isolation from the solvents used in the synthetic preparation of such compounds.

The β1AR blocker or antiarrhythmic agents of the present disclosure can be prepared in a racemic mixture (e.g., mixture of isomers) that contains more than 50%, preferably at least 75%, and more preferably at least 90% of the desired isomer (e.g., 80% enantiomeric or diastereomeric excess). According to particularly preferred embodiments, the compounds of the present invention are prepared in a form that contains at least 95% (90% e.e. or d.e.), even more preferably at least 97.5% (95% e.e. or d.e.), and most preferably at least 99% (98% e.e. or d.e.) of the desired isomer. Compounds identified herein as single stereoisomers are meant to describe compounds used in a form that contains more than 50% of a single isomer. By using known techniques, these compounds may be isolated in any of such forms by slightly varying the method of purification and/or isolation from the solvents used in the synthetic preparation of such compounds.

Methods of Treatment

The methods, compositions, and kits provided herein can include administration of the pharmaceutical agents via inhalation, e.g., oral or nasal inhalation, or intranasal spray administration.

Administration Methods and Devices

The therapy provided herein can comprise or be suitable for oral or nasal administration, e.g., oral or nasal inhalation, or intranasal spray administration. As provided herein, the term "oral or nasal administration" can refer to oral inhalation, nasal inhalation, or intranasal spray administration. In some cases, during administration via oral inhalation, the pharmaceutical agent is inhaled by the patient through the mouth and absorbed by the lungs. In some cases, during administration via nasal inhalation, the pharmaceutical agent is inhaled by the patient through the nose and absorbed by the nasal mucous and/or the lungs. In some cases, during intranasal spray administration, pharmaceutical agent is sprayed into the nose of the patient and subsequently absorbed by the nasal mucous and/or the lungs. In some cases, during intranasal spray administration, the pharmaceutical agent is passively administered to the patient, e.g., the patient does not actively inhale the sprayed agent. In some cases, during intranasal spray administration, the pharmaceutical agent is both passively and actively administered to the patient, e.g., the agent is at least partially actively inhaled by the patient through the nose after being sprayed intranasally.

The inhalation or intranasal spray administration routes can avoid first-pass hepatic metabolism, hence dosing variability can be eliminated. Unlike the case for oral tablets or pills, the patient's metabolic rates may not matter as the administration is independent of the metabolic paths experienced when a drug is administered via oral route through gastrointestinal tract, e.g., as tablets, pills, solution, or suspension.

A fast onset of action, a potential improvement in efficacy, and/or a reduction in dose can be achieved with the fast absorption of drugs from the nasal mucosa and/or lungs.

The fast absorption rate of drugs through the lungs can be achieved because of the large surface area available in the lungs for aerosols small enough to penetrate central and peripheral lung regions. For nasal delivery or intranasal spray delivery, the nasal mucosa can have a relatively high permeable epithelium layer, and a sub-epithelial layer that is highly vascularized, which can provide direct access of drugs for absorption into the systemic circulation. Consequently, the rate and extent of absorption of drugs delivered via the oral or nasal administration routes can yield plasma concentrations vs. time profiles that are comparable with the IV route of administration.

The time for onset of action can be short. For instance, the patient may have normal sinus rhythm within 20 minutes of initiating the administering, such as within 15 minutes, within 10 minutes, or within 5 minutes of initiating the administering. In some cases, the rapid onset of action is advantageous because the longer a patient has had arrhythmia, the longer it can take to convert the patient to normal sinus rhythm.

In some embodiments, the method of the present disclosure allows the patient to avoid other therapies, such as ablation and/or electrical cardioversion. In other embodiments, the method of the present invention is used in combination with other therapies, such as before or after electrical cardioversion and/or ablation therapy.

Oral or Nasal Inhalation

In some aspects of the present disclosure, the compositions or formulations of the pharmaceutical agents, e.g., β1AR blocker, class I antiarrhythmic agent, or both, are administered via inhalation. The pharmaceutical formulations can be aerosolized prior to administration or can be presented to a user in the form of an aerosol.

The pharmaceutical compositions can be administered using an aerosolization device. The aerosolization device can be a nebulizer, a metered dose inhaler, a liquid dose instillation device, or a dry powder inhaler. The aerosolization device can comprise the extrusion of the pharmaceutical preparation through micron or submicron-sized holes with subsequent Rayleigh break-up into fine droplets. The pharmaceutical composition can be delivered by a nebulizer as described in WO 99/16420, by a metered dose inhaler as described in WO 99/16422, by a liquid dose instillation apparatus as described in WO 99/16421, and by a dry powder inhaler as described in U.S. Published Application Nos. 20020017295 and 20040105820, WO 99/16419, WO 02/83220, and U.S. Pat. No. 6,546,929, which are incorporated herein by reference in their entireties. As such, an inhaler can comprise a canister containing the particles or particles and propellant, and wherein the inhaler comprises a metering valve in communication with an interior of the canister. The propellant can be a hydrofluoroalkane.

For instance, the pharmaceutical formulation can be in liquid solution, and can be administered with nebulizers, such as that disclosed in PCT WO 99/16420, the disclosure of which is hereby incorporated in its entirety by reference, in order to provide an aerosolized medicament that can be administered to the pulmonary air passages of a patient in need thereof. Nebulizers known in the art can easily be employed for administration of the claimed formulations. Breath-activated or breath-actuated nebulizers, as well as those comprising other types of improvements which have been, or will be, developed are also compatible with the formulations of the present disclosure and are contemplated as being within the scope thereof.

In some cases, the nebulizer is a breath activated or breath-actuated nebulizer. In some cases, the nebulizer is a hand-held inhaler device (e.g., AeroEclipse® II Breath Actuated Nebulizer (BAN)). In some cases, the nebulizer has a compressed air source. In some cases, the nebulizer converts liquid medication into an aerosol. In some cases, the nebulizer converts liquid medication into an aerosol by extruding the pharmaceutical preparation through micron or submicron-sized holes. In some cases, the nebulizer converts liquid medication into an aerosol so it can be inhaled into the lungs. In some cases, the nebulizer is a small volume nebulizer. In some cases, the nebulizer is a small volume jet nebulizer. In some cases, aerosolized medication is only produced when inhaled through the device. In some cases, the medication is contained in the cup between breaths or during breaks in treatment. In some cases, the medication is contained in the cup until ready to be inhaled.

Nebulizers can impart energy into a liquid pharmaceutical formulation to aerosolize the liquid, and to allow delivery to the pulmonary system, e.g., the lungs, of a patient. A nebulizer comprises a liquid delivery system, such as a container having a reservoir that contains a liquid pharmaceutical formulation. The liquid pharmaceutical formulation generally comprises an active agent that is either in solution or suspended within a liquid medium.

In one type of nebulizer that can be used in the subject methods and kits, generally referred to as a jet nebulizer, compressed gas is forced through an orifice in the container. The compressed gas forces liquid to be withdrawn through a nozzle, and the withdrawn liquid can mix with the flowing gas to form aerosol droplets. A cloud of droplets can then be administered to the patients respiratory tract.

In another type of nebulizer that can be used in the subject methods and kits, generally referred to as a vibrating mesh nebulizer, energy, such as mechanical energy, vibrates a mesh. This vibration of the mesh aerosolizes the liquid pharmaceutical formulation to create an aerosol cloud that is administered to the patient's lungs. In another type of nebulizer that can be used in the subject methods and kits, the nebulizing comprises extrusion through micron or submicron-sized holes followed by Rayleigh break-up into fine droplets.

Alternatively or additionally, the pharmaceutical formulation may be in a liquid form and may be aerosolized using a nebulizer as described in WO 2004/071368, which is herein incorporated by reference in its entirety, as well as U.S. Published application Nos. 2004/0011358 and 2004/0035413, which are both herein incorporated by reference in their entireties. Other examples of nebulizers include, but are not limited to, the Aeroneb® Go or Aeroneb® Pro nebulizers, available from Aerogen Ltd. of Galway, Ireland; the PARI eFlow and other PART nebulizers available from PARI Respiratory Equipment, Inc. of Midlothian, Va.; the Lumiscope® Nebulizer 6600 or 6610 available from Lumiscope Company, Inc. of East Brunswick, N.J.; and the Omron NE-U22 available from Omron Healthcare, Inc. of Kyoto, Japan. Other examples of nebulizers include devices produced by Medspray (Enschede, The Netherlands).

It has been found that a nebulizer of the vibrating mesh type, such as one that that forms droplets without the use of compressed gas, such as the Aeroneb® Pro provides unexpected improvement in dosing efficiency and consistency. By generating fine droplets by using a vibrating perforated or unperforated membrane, rather than by introducing compressed air, the aerosolized pharmaceutical formulation can be introduced without substantially affecting the flow characteristics. In addition, the generated droplets when using a nebulizer of this type are introduced at a low velocity, thereby decreasing the likelihood of the droplets being driven to an undesired region. It has been found that when using a nebulizer of the extrusion/Rayleigh jet breakup type, the generated droplets are also introduced at a low velocity, thereby decreasing the likelihood of the droplets being driven to an undesired region.

In some cases, the nebulizer that can be used in the subject methods and kits is of the vibrating mesh type. In some cases, the nebulizer that can be used in the subject methods and kits is of the pressurized jet type. In some cases, the nebulizer that can be used in the subject methods and kits is of the extrusion/Rayleigh breakup type. In some cases, the nebulizer is lightweight (at most 60 g, at most 100 g, at most 200 g, at most 250 g) and nearly silent. In some cases, the nebulizer has a sound level less than 35 A-weighted decibels (dBA) at 1 meter. In some cases, the nebulizer has a medication cup capacity of 6 mL. In some cases, the nebulizer has a residual volume of less than 0.3 mL. In some cases, the nebulizer generates an average flow rate of 0.4 mL/min. In some cases, the nebulizer generates an average flow rate of 0.5 mL/min. In some cases, the nebulizer generates an average flow rate of 0.6 mL/min. In some cases, the nebulizer generates an average flow rate of 0.7 mL/min. In some cases, the nebulizer generates an average flow rate of 0.8 mL/min. In some cases, the nebulizer generates an average flow rate of 0.9 mL/min. In some cases, the nebulizer generates an average flow rate of 1.0 mL/min. In some cases, the nebulizer generates an average flow rate of 1.1 mL/min. In some cases, the nebulizer generates an average flow rate of 1.2 mL/min. In some cases, the nebulizer generates an average particle size of 3.0 μm MMAD. In some cases, the nebulizer generates an average particle size between 3.0 μm MMAD and 4.0 μm MMAD. In some cases, the nebulizer generates an average particle size of 3.0 μm MMAD. In some cases, the nebulizer generates an average particle size between 3.0 μm MMAD and 5.0 μm MMAD. In some cases, the nebulizer generates an average particle size of 3.0 μm MMAD. In some cases, the nebulizer generates an average particle size between 3.0 μm MMAD and 6.0 μm MMAD.

In still another type of nebulizer that can be used in the subject methods and kits, ultrasonic waves are generated to directly vibrate and aerosolize the pharmaceutical formulation.

Alternatively or additionally, the present disclosure can involve a dry powder inhaler. A specific version of a dry powder aerosolization apparatus is described in U.S. Pat. Nos. 4,069,819 and 4,995,385, which are incorporated herein by reference in their entireties. Another useful device, which has a chamber that is sized and shaped to receive a capsule so that the capsule is orthogonal to the inhalation direction, is described in U.S. Pat. No. 3,991,761, which is incorporated herein by reference in its entirety. As also described in U.S. Pat. No. 3,991,761, a puncturing mechanism may puncture both ends of the capsule. In another version, a chamber can receive a capsule in a manner where air flows through the capsule as described for example in U.S. Pat. Nos. 4,338,931 and 5,619,985, which are incorporated herein by reference in their entireties. In another version, the aerosolization of the pharmaceutical composition can be accomplished by pressurized gas flowing through the inlets, as described for example in U.S. Pat. Nos. 5,458,135; 5,785,049; and 6,257,233, or propellant, as described in WO 00/72904 and U.S. Pat. No. 4,114,615, which are incorporated herein by reference. These types of dry powder inhalers are generally referred to as active dry powder inhalers.

Other dry powder inhalers can include those available from Boehringer Ingelheim (e.g., Respimat inhaler), Hovione (e.g., FlowCaps inhaler), Plastiape (e.g., Osmohaler inhaler), and MicroDose. The present invention may also utilize condensation aerosol devices, available from Alexza, Mountain View, Calif. Yet another useful inhaler is disclosed in WO 2008/051621, which is incorporated herein by reference in its entirety.

The pharmaceutical formulations disclosed herein can also be administered to the lungs of a patient via aerosolization, such as with a metered dose inhaler. The use of such formulations provides for superior dose reproducibility and improved lung deposition as disclosed in WO 99/16422, hereby incorporated in its entirety by reference. Metered dose inhalers (MDIs) known in the art can be employed for administration of the claimed pharmaceutical compositions. Breath-activated or breath-actuated MDIs and pressurized MDIs (pMDIs), as well as those comprising other types of improvements which have been, or will be, developed are also compatible with the formulations of the present disclosure and, as such, are contemplated as being within the scope thereof.

Along with DPIs, MDIs and nebulizers, it will be appreciated that the formulations of one or more embodiments of the present invention can be used in conjunction with liquid dose instillation or LDI techniques as disclosed in, for example, WO 99/16421, which is incorporated herein by reference in its entirety. Liquid dose instillation involves the direct administration of a formulation to the lung. With respect to LDI the formulations are preferably used in conjunction with partial liquid ventilation or total liquid ventilation. Moreover, one or more embodiments of the present invention may further comprise introducing a therapeutically beneficial amount of a physiologically acceptable gas (such as nitric oxide or oxygen) into the pharmaceutical microdispersion prior to, during or following administration.

The pharmaceutical composition of one or more embodiments of the present disclosure can have improved emitted dose efficiency. Accordingly, high doses of the pharmaceutical composition can be delivered using a variety of aerosolization devices and techniques.

The emitted dose (ED) of the particles of the present invention may be greater than about 30%, such as greater than about 40%, greater than about 50%, greater than about 60%, or greater than about 70%.

Intranasal Spray Administration

In some aspects, the present disclosure relates to intranasal spray administration of the pharmaceutical compositions for treatment of a subject suffering from a heart condition, e.g., cardiac arrhythmia, e.g., atrial arrhythmia. Nasal spray device can be used for the purpose of spraying the pharmaceutical formula in aerosol form into nasal cavity. For nasal administration, a useful device can be a small, hard bottle to which a metered dose sprayer is attached. In some cases, the metered dose is delivered by drawing the pharmaceutical solution described herein into a chamber of defined volume, which chamber has an aperture dimensioned to aerosolize and aerosol formulation by forming a spray when a liquid in the chamber is compressed. The chamber is compressed to administer the pharmaceutical agents, e.g., β1AR blocker, class I antiarrhythmic agent, or both. In some cases, the chamber is a piston arrangement. Such devices are commercially available. Alternatively, a plastic squeeze bottle with an aperture or opening dimensioned to aerosolize an aerosol formulation by forming a spray when squeezed. The opening can be found in the top of the bottle, and the top is generally tapered to partially fit in the nasal passages for efficient administration of the aerosol formulation. The nasal inhaler can provide a metered amount of the aerosol formulation, for administration of a measured dose of the drug.

In some cases, the Aptar/Pfeiffer Unitdose delivery device is used to deliver the disclosed compositions. Other devices that can be used according to the present disclosure include, but not limited to, those as described in Djupesland, Drug Deliv Transl Res. (2013) February; 3(1). In some cases, the nasal spray device delivers a volume of about 50 μL, about 60 μL, about 80 μL, about 100 μL, about 150 μL, about 200 μL, about 300 μL, about 400 μL, about 500 μL, about 600 μL, about 700 μL, about 800 μL per spray. In some cases, the nasal spray device is configured to deliver the pharmaceutical formula in more than one sprays, for instance, 2, 3, 4, 5, 6, 7, 8, 9, 10, or even more sprays. The direct product contact components of the container closure can comprise a container (glass vial), manufactured using FIOLAX glass by MGLAS or NUOVA OMPI, a plunger (Stopper).

The nasal spray device can be intended for use by both medical and non-medical personnel. The device can have one or more features selected from being single-use, needle-free, ready-to-use, disposable, and combinations thereof. The device may be configured to administer the disclosed compositions as a single spray per naris. The device can comprise one or more unit dose containers, each container delivering about one 100 μL spray. In other aspects, the devices may be modified to deliver amounts of between about 50 μL to about 800 μL spray, and can utilize solutions of varying concentration. Any nasal spray device known in the art can be used to deliver the nasal spray and compositions described herein. In one aspect, the nasal spray device is an Aptar/Pfeiffer Unitdose device. The nasal spray provided herein can comprise a preserved solution with pH and osmolality appropriate for nasal administration. Similarly, it can be prepared as a sterile solution without an antimicrobial preservative.

Ease of Use

Oral or nasal administration provided herein can be a procedure that is quick, easy, and commonly used by patients.

Dosing can be performed at home, in a hospital setting, or in both settings.

Oral or nasal administration of β1AR blocker, e.g., metoprolol or nebivolol, class I antiarrhythmic agent, or both can address the need to rapidly reduce the cardiostimulatory (e.g. fast AV nodal conduction) effects of sympathetic drive triggered by many causes such as anxiety associated with fast and irregular rhythm of AF, and consequently slow the ventricular rate.

Administration Regimen

Concomitant or Serial Administration with Antiarrhythmic Therapy

β1AR blocker provided herein can be concomitantly or sequentially be administered with an antiarrhythmic therapy, e.g., an antiarrhythmic agent, e.g., a class antiarrhythmic agent. The fast and selective blockade in the heart resulting from oral or nasal administration of β1AR blocker, e.g., metoprolol or nebivolol, prior to or concomitant with, the administration of an antiarrhythmic therapy would potentially eliminate adverse side effects (e.g., 1:1 AV nodal conduction), increase the probability of conversion of AF to NSR, and/or reduce the recurrence of AF by suppressing the consequences of high sympathetic tone, such as atrial ectopy. For example, the patient could self-administer an antiarrhythmic drug within a few minutes (e.g., 5-15 min) of self-administering a β1AR blocker like nebivolol or d-nebivolol.

In some cases, the administration of the β1AR blocker takes place up to up to about 90 minutes, about 75 minutes, about 60 minutes, about 45 minutes, about 30 minutes, about 20 minutes, about 15 minutes, about 10 minutes, or about 5 minutes earlier than the administration of the antiarrhythmic agent, e.g., class I antiarrhythmic agent. In some cases, the interval between administration of the two drugs can vary, e.g., depending on the pharmacological response to the administration of the β1AR blocker. For instance, the heart beating can be monitored by a device, e.g., electronic monitoring device, e.g., ECG, and the administration of the follow-on drug, e.g., the other antiarrhythmic agent, e.g., the class I antiarrhythmic agent, can be performed when, or only if, one or more parameters of the ECG recording meet a certain predetermined threshold. In some cases, a doctor's assessment of the pharmacological responses is required for determining the administration of the class I antiarrhythmic agent. In some cases, the interval between administration of the two drugs is fixed, such as, about 90 minutes, about 75 minutes, about 60 minutes, about 45 minutes, about 30 minutes, about 20 minutes, about 15 minutes, about 10 minutes, or about 5 minutes.

In other cases, the administration of the β1AR blocker takes place concurrently with the administration of the antiarrhythmic agent, e.g., class I antiarrhythmic agent. For instance, an aerosolization device that is configured to deliver two separate drug formulations at the same time can be used. In such a device, the two drug formulations, e.g., containing a β1AR blocker and a class I antiarrhythmic agent, respectively, can be received in two separate receptacles, and the device can form an aerosol containing both of the two formulations, which ensures the subject inhaling the two drugs at the same time. In other examples, one combination pharmaceutical composition is provided, containing both of the two drugs, e.g., β1AR blocker and class I antiarrhythmic agent. In such cases, the combination composition is administered to the subject via inhalation or intranasal spray administration, thereby achieving therapeutic effects of co-administration of the two active agents.

The methods provided herein can comprise administration of an antiarrhythmic agent, e.g., a class I antiarrhythmic agent, for induction of cardioversion. The methods provided herein can further comprise application of an electric current for induction of cardioversion. The cardioversion provided herein can comprise both pharmaceutic and electrical.

The pharmaceutical composition can be administered to the patient on an as-needed basis. For instance, the methods, kits, and compositions can find particular use in treating a subject experiencing a heart condition, e.g., cardiac arrhythmia, e.g., atrial arrhythmia. In some cases, a subject is administered with the therapy described herein when he/she is experiencing atrial arrhythmia. In some cases, the therapy, for instance, the combination inhalatory therapy with both β1AR blocker and class I antiarrhythmia is administered to a subject after the onset of an episode of cardiac arrhythmia. In other cases, the subject is treated between episodes of cardiac arrhythmias.

The dose of the drug, e.g., a β1AR blocker, a class I antiarrhythmia, or both, can be administered during a single inhalation or can be administered during several inhalations. The fluctuations of antiarrhythmic pharmaceutical agent concentration can be reduced by administering the pharmaceutical composition more often or can be increased by administering the pharmaceutical composition less often. Therefore, the pharmaceutical composition provided herein can be administered from about four times daily to about once a month, such as about once daily to about once every two weeks, about once every two days to about once a week, and about once per week.

In one version, the antiarrhythmic can be administered daily. In this case, the daily dosage of β1AR blocker or antiarrhythmic agent ranges from about 0.1 mg to about 600 mg, such as about 0.5 mg to about 500 mg, about 1 mg to about 400 mg, about 2 mg to about 300 mg, and about 3 mg to about 200 mg.

In some cases, the therapy provided herein is provided to a subject for more than once on an as-needed basis. For instance, the present invention may involve a follow-up inhalation if no cardioversion occurs after an initial inhalation. In some instances, if no cardioversion occurs within 30 minutes of the initial inhalation, the follow-up dosage is higher or the same as the initial dosage.

The dosing can be guided by how the patient feels. Also or alternatively, dosing can be guided by using a portable/mobile ECG device. For instance, the dosing may be guided by using a Holter monitor.

In another version, the pharmaceutical composition is administered prophylactically to a subject who is likely to develop an arrhythmia. For example, a patient who has a history of arrhythmias can be prophylactically treated with a pharmaceutical composition comprising antiarrhythmic pharmaceutical agent to reduce the likelihood of developing an arrhythmia.

The pharmaceutical composition can be administered to a patient in any regimen which is effective to prevent an arrhythmia. Illustrative prophylactic regimes include administering an antiarrhythmic pharmaceutical agent as described herein 1 to 21 times per week.

The amount of β1AR blocker, e.g., metoprolol or nebivolol, for the treatment of arrhythmia can be at least about 0.1 mg, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 250, 300, 350, 400, 450, or 500 mg. The amount of β1AR blocker, e.g., metoprolol or nebivolol, for the treatment of arrhythmia can range about 0.1-100 mg, such as about 0.1-100, 0.1-90, 0.1-80, 0.1-70, 0.1-50, 0.1-30, 0.1-10, 0.1-9, 0.1-8, 0.1-7, 0.1-6, 0.1-5, 0.1-4.5, 0.1-4, 0.1-3.5, 0.1-3, 0.1-2.5, 0.1-2, 0.1-1.5, 0.1-1.0, 0.1-0.5, 1-100, 1-90, 1-70, 1-50, 1-30, 1-10, 1-9, 1-8, 1-7, 1-6, 1-5, 1-4.5, 1-4, 1-3.5, 1-3, 1-2.5, 1-2, 1-1.5, 1.5-100, 1.5-90, 1.5-70, 1.5-50, 1.5-30, 1.5-10, 1.5-9, 1.5-8, 1.5-7, 1.5-6, 1.5-5, 1.5-4.5, 1.5-4, 1.5-3.5, 1.5-3, 1.5-2.5, 1.5-2, 2-100, 2-90, 2-70, 2-50, 2-30, 2-10, 2-9, 2-8, 2-7, 2-6, 2-5, 2-4.5, 2-4, 2-3.5, 2-3, 2-2.5, 2.5-100, 2.5-90, 2.5-70, 2.5-50, 2.5-30, 2.5-10, 2.5-9, 2.5-8, 2.5-7, 2.5-6, 2.5-5, 2.5-4.5, 2.5-4, 2.5-3.5, 2.5-3, 3-100, 3-90, 3-70, 3-50, 3-30, 3-10, 3-9, 3-8, 3-7, 3-6, 3-5, 3-4.5, 3-4, 3-3.5, 3.5-100, 3.5-90, 3.5-70, 3.5-50, 3.5-30, 3.5-10, 3.5-9, 3.5-8, 3.5-7, 3.5-6, 3.5-5, 3.5-4.5, 3.5-4, 5-100, 5-90, 5-70, 5-50, 5-30, 5-10, 10-100, 10-90, 10-70, 10-50, 10-30, 30-100, 30-90, 30-70, 30-50, 50-100, 50-90, 50-70, 70-100, 70-90, or 90-100 mg. For example, the amount of β1AR blocker, e.g., metoprolol or nebivolol, for the treatment of arrhythmia can range about from 1 to about 10 mg. In some cases, the β1AR blocker is used in the range of about 1 to about 4 mg.

The amount of antiarrhythmic agent, e.g., class I antiarrhythmic agent, for the treatment of arrhythmia can be at least about 0.1 mg, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 250, 300, 350, 400, 450, or 500 mg. The amount of antiarrhythmic agent, e.g., class I antiarrhythmic agent, for the treatment of arrhythmia can range about 0.01-500 mg, such as about 0.1-500, 0.1-450, 0.1-400, 0.1-350, 0.1-300, 0.1-250, 0.1-200, 0.1-150, 0.1-130, 0.1-110, 0.1-90, 0.1-70, 0.1-50, 0.1-30, 0.1-10, 0.1-5, 0.1-1.0, 0.1-0.5, 1-500, 1-450, 1-400, 1-350, 1-300, 1-250, 1-200, 1-150, 1-130, 1-110, 1-90, 1-70, 1-50, 1-30, 1-10, 1-5, 5-500, 5-450, 5-400, 5-350, 5-300, 5-250, 5-200, 5-150, 5-130, 5-110, 5-90, 5-70, 5-50, 5-30, 5-10, 10-500, 10-450, 10-400, 10-350, 10-300, 10-250, 10-200, 10-150, 10-130, 10-110, 10-90, 10-70, 10-50, 10-30, 30-500, 30-450, 30-400, 30-350, 30-300, 30-250, 30-200, 30-150, 30-130, 30-110, 30-90, 30-70, 30-50, 50-500, 50-450, 50-400, 50-350, 50-300, 50-250, 50-200, 50-150, 50-130, 50-110, 50-90, 50-70, 70-500, 70-450, 70-400, 70-350, 70-300, 70-250, 70-200, 70-150, 70-130, 70-110, 70-90, 90-500, 90-450, 90-400, 90-350, 90-300, 90-250, 90-200, 90-150, 90-130, 90-110, 110-500, 110-450, 110-400, 110-350, 110-300, 110-250, 110-200, 110-150, 110-130, 130-500, 130-450, 130-400, 130-350, 130-300, 130-250, 130-200, 130-150, 150-500, 150-450, 150-400, 150-350, 150-300, 150-250, 150-200, 200-500, 200-450, 200-400, 200-350, 200-300, 200-250, 250-500, 250-450, 250-400, 250-350, 250-300, 300-500, 300-450, 300-400, 300-350, 350-500, 350-450, 350-400, 400-500, 400-450, or 450-500 mg. For example, the amount of antiarrhythmic agent, e.g., class I antiarrhythmic agent, for the treatment of arrhythmia can range about from 10 to about 80 mg. In some cases, class I antiarrhythmic agent is used in the range of about 20 to about 60 mg.

Indications and Subjects

Examples of cardiac arrhythmias the methods, compositions, and kits provided herein can treat include, but are not limited to, tachycardia, supraventricular tachycardia (SVT), paroxysmal supraventricular tachycardia (PSVT), atrial fibrillation (AF), paroxysmal atrial fibrillation (PAF), persistent atrial fibrillation, permanent atrial fibrillation, atrial flutter, paroxysmal atrial flutter, and lone atrial fibrillation. In some cases, the methods, compositions, and kits provided herein find use in treating a subject suffering from atrial arrhythmia, e.g., atrial fibrillation.

Thus, the pharmaceutical compositions according to some examples of the present disclosure can be used to treat and/or provide prophylaxis for a broad range of patients. A suitable patient for, receiving treatment and/or prophylaxis as described herein is any mammalian patient in need thereof, preferably such mammal is a human. Examples of subjects include, but are not limited to, pediatric patients, adult patients, and geriatric patients. In some cases, the composition is intended only as a treatment for rapid resolution of symptoms and restoration of normal sinus rhythm, and is not taken as a preventative, e.g., when the patient is well, there is no need for drug—this can increase the benefit-risk ratio of the therapy and overall safety due to the sporadic or intermittent dosing, and the focus on reducing disabling symptoms and restoring sinus rhythm only when needed.

The dosage necessary and the frequency of dosing of the antiarrhythmic pharmaceutical agent depend on the composition and concentration of the antiarrhythmic pharmaceutical agent within the composition. In some cases, the dose is less than about 10%, 20%, 30%, 40%, 50%, 60%, 70%, 80%, 90%, or 95% of its normal intravenous dose. In some cases, the dose is about 5% to about 10%, is about 10% to about 20%, is about 20% to about 30%, is about 30% to about 40%, is about 50% to about 60%, is about 60% to about 70%, is about 70% to about 80%, is about 80% to about 90%, or is about 90% to about 95% of the intravenous dose.

The pharmaceutical compositions used for combination therapy provided herein can include a dose of a β1AR blocker and a dose of an antiarrhythmic agent, e.g., class I antiarrhythmic agent, that is less than 10%, 20%, 30%, 40%, 50%, 60%, 70%, 80%, 90%, or 95% of their respective normal dose when used alone without the other agent in a corresponding subject. in some cases, the pharmaceutical compositions used for combination therapy provided herein can include a dose of a β1AR blocker and a dose of an antiarrhythmic agent, e.g., class I antiarrhythmics, that is less than 10%, 20%, 30%, 40%, 50%, 60%, 70%, 80%, 90%, or 95% of their respective minimum therapeutically effective dose when used alone without the other agent in a corresponding subject.

Formulations and Kits

In one aspect, provided herein are pharmaceutical composition for treatment of a heart condition, e.g., cardiac arrhythmia, e.g., atrial arrhythmia.

The pharmaceutical composition can include a therapeutically effective amount of a β1AR blocker. The therapeutically effective amount of β1AR blocker can be effective for treatment of a heart condition, e.g., cardiac arrhythmia, e.g., atrial arrhythmia, when it is administered to a subject in need thereof via inhalation or intranasal spray administration. In some cases, the therapeutically effective amount of β1AR blocker is effective for treatment of atrial arrhythmia by inducing cardioversion and slowing AV node conduction when it is administered to a subject in need thereof via inhalation or intranasal spray administration.

In some cases, provided herein are pharmaceutical composition including a therapeutically effective amount of β1AR blocker and a therapeutically effective amount of an antiarrhythmic agent, e.g., class I antiarrhythmic agent. In some cases, the therapeutically effective amount of the β1AR blocker and the therapeutically effective amount of the class I antiarrhythmic agent are effective for treatment of atrial arrhythmia by inducing cardioversion and slowing AV node conduction when it is administered to a subject in need thereof via inhalation or intranasal spray administration.

The β1AR blocker can be in a liquid solution. In some cases, the concentration of a β1AR blocker in the pharmaceutical compositions or formulations provided herein is about 1 mg/mL to about 60 mg/mL, such as 1 mg/mL to 5 mg/mL, 1 mg/ml to 10 mg/mL, 1 mg/ml to 15 mg/mL, 1 mg/mL to 20 mg/mL, 1 mg/mL to 25 mg/mL, 1 mg/mL to 30 mg/mL, 1 mg/mL to 35 mg/mL, 1 mg/mL to 40 mg/mL, 1 mg/mL to 45 mg/mL, 1 mg/mL to 50 mg/mL, 1 mg/mL to 55 mg/mL, 5 mg/ml to 10 mg/mL, 5 mg/ml to 15 mg/mL, 5 mg/mL to 20 mg/mL, 5 mg/mL to 25 mg/mL, 5 mg/mL to 30 mg/mL, 5 mg/mL to 35 mg/mL, 5 mg/mL to 40 mg/mL, 5 mg/mL to 45 mg/mL, 5 mg/mL to 50 mg/mL, 5 mg/mL to 55 mg/mL, 5 mg/mL to 60 mg/mL; 10 mg/ml to 15 mg/mL, 10 mg/mL to 20 mg/mL, 10 mg/mL to 25 mg/mL, 10 mg/mL to 30 mg/mL, 10 mg/mL to 35 mg/mL, 10 mg/mL to 40 mg/mL, 10 mg/mL to 45 mg/mL, 10 mg/mL to 50 mg/mL, 10 mg/mL to 55 mg/mL, 10 mg/mL to 60 mg/mL, 15 mg/mL to 20 mg/mL, 15 mg/mL to 25 mg/mL, 15 mg/mL to 30 mg/mL, 15 mg/mL to 35 mg/mL, 15 mg/mL to 40 mg/mL, 15 mg/mL to 45 mg/mL, 15 mg/mL to 50 mg/mL, 15 mg/mL to 55 mg/mL, 15 mg/mL to 60 mg/mL, 20 mg/mL to 25 mg/mL, 20 mg/mL to 30 mg/mL, 20 mg/mL to 35 mg/mL, 20 mg/mL to 40 mg/mL, 20 mg/mL to 45 mg/mL, 20 mg/mL to 50 mg/mL, 20 mg/mL to 55 mg/mL, 20 mg/mL to 60 mg/mL, 25 mg/mL to 30 mg/mL, 25 mg/mL to 35 mg/mL, 25 mg/mL to 40 mg/mL, 25 mg/mL to 45 mg/mL, 25 mg/mL to 50 mg/mL, 25 mg/mL to 55 mg/mL, 25 mg/mL to 60 mg/mL, 30 mg/mL to 35 mg/mL, 30 mg/mL to 40 mg/mL, 30 mg/mL to 45 mg/mL, 30 mg/mL to 50 mg/mL, 30 mg/mL to 55 mg/mL, 30 mg/mL to 60 mg/mL, 35 mg/mL to 40 mg/mL, 35 mg/mL to 45 mg/mL, 35 mg/mL to 50 mg/mL, 35 mg/mL to 55 mg/mL, 35 mg/mL to 60 mg/mL, 40 mg/mL to 45 mg/mL, 40 mg/mL to 50 mg/mL, 40 mg/mL to 55 mg/mL, 40 mg/mL to 60 mg/mL, 45 mg/mL to 50 mg/mL, 45 mg/mL to 55 mg/mL, 45 mg/mL to 60 mg/mL, 50 mg/mL to 55 mg/mL, 50 mg/mL to 60 mg/mL, or 55 mg/mL to 60 mg/mL.

In some aspects, also provided herein are unit doses of pharmaceutical compositions described herein for treatment of heart condition, e.g., cardiac arrhythmia, e.g., atrial arrhythmia, via oral or nasal inhalation, or intranasal spray administration.

In one version, a unit dose of β1AR blocker includes at least about 0.1 mg, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 250, 300, 350, 400, 450, or 500 mg β1AR blocker, e.g., metoprolol, nebivolol, a pharmaceutically acceptable salt or solvate thereof. A unit dose of β1AR blocker can include the β1AR blocker, e.g., metoprolol, nebivolol, a pharmaceutically acceptable salt or solvate thereof in the range of about 0.1-100 mg, such as about 0.1-100, 0.1-90, 0.1-80, 0.1-70, 0.1-50, 0.1-30, 0.1-10, 0.1-9, 0.1-8, 0.1-7, 0.1-6, 0.1-5, 0.1-4.5, 0.1-4, 0.1-3.5, 0.1-3, 0.1-2.5, 0.1-2, 0.1-1.5, 0.1-1.0, 0.1-0.5, 1-100, 1-90, 1-70, 1-50, 1-30, 1-10, 1-9, 1-8, 1-7, 1-6, 1-5, 1-4.5, 1-4, 1-3.5, 1-3, 1-2.5, 1-2, 1-1.5, 1.5-100, 1.5-90, 1.5-70, 1.5-50, 1.5-30, 1.5-10, 1.5-9, 1.5-8, 1.5-7, 1.5-6, 1.5-5, 1.5-4.5, 1.5-4, 1.5-3.5, 1.5-3, 1.5-2.5, 1.5-2, 2-100, 2-90, 2-70, 2-50, 2-30, 2-10, 2-9, 2-8, 2-7, 2-6, 2-5, 2-4.5, 2-4, 2-3.5, 2-3, 2-2.5, 2.5-100, 2.5-90, 2.5-70, 2.5-50, 2.5-30, 2.5-10, 2.5-9, 2.5-8, 2.5-7, 2.5-6, 2.5-5, 2.5-4.5, 2.5-4, 2.5-3.5, 2.5-3, 3-100, 3-90, 3-70, 3-50, 3-30, 3-10, 3-9, 3-8, 3-7, 3-6, 3-5, 3-4.5, 3-4, 3-3.5, 3.5-100, 3.5-90, 3.5-70, 3.5-50, 3.5-30, 3.5-10, 3.5-9, 3.5-8, 3.5-7, 3.5-6, 3.5-5, 3.5-4.5, 3.5-4, 4-4.5, 4-5, 4-6, 4-8, 4-10, 5-100, 5-90, 5-70, 5-50, 5-30, 5-10, 10-100, 10-90, 10-70, 10-50, 10-30, 30-100, 30-90, 30-70, 30-50, 50-100, 50-90, 50-70, 70-100, 70-90, or 90-100 mg. For example, in a unit dose of β1AR blocker the amount of β1AR blocker, e.g., metoprolol, nebivolol or a pharmaceutically acceptable salt of solvate thereof, can range about from 1 to about 10 mg. In some cases, the amount of β1AR blocker, e.g., metoprolol, nebivolol or a pharmaceutically acceptable salt of solvate thereof, ranges about 1 to about 4 mg.

In one version, a unit dose as provided herein includes a dosage of a β1AR blocker and also includes at least about 0.1 mg, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 250, 300, 350, 400, 450, or 500 mg antiarrhythmic agent, e.g., class I antiarrhythmic agent. A unit dose of antiarrhythmic agent can include the antiarrhythmic agent, e.g., class I antiarrhythmic agent, in the range of about 0.01-500 mg, such as about 0.1-500, 0.1-450, 0.1-400, 0.1-350, 0.1-300, 0.1-250, 0.1-200, 0.1-150, 0.1-130, 0.1-110, 0.1-90, 0.1-70, 0.1-50, 0.1-30, 0.1-10, 0.1-5, 0.1-1.0, 0.1-0.5, 1-500, 1-450, 1-400, 1-350, 1-300, 1-250, 1-200, 1-150, 1-130, 1-110, 1-90, 1-70, 1-50, 1-30, 1-10, 1-5, 5-500, 5-450, 5-400, 5-350, 5-300, 5-250, 5-200, 5-150, 5-130, 5-110, 5-90, 5-70, 5-50, 5-30, 5-10, 10-500, 10-450, 10-400, 10-350, 10-300, 10-250, 10-200, 10-150, 10-130, 10-110, 10-90, 10-70, 10-50, 10-30, 30-500, 30-450, 30-400, 30-350, 30-300, 30-250, 30-200, 30-150, 30-130, 30-110, 30-90, 30-70, 30-50, 50-500, 50-450, 50-400, 50-350, 50-300, 50-250, 50-200, 50-150, 50-130, 50-110, 50-90, 50-70, 70-500, 70-450, 70-400, 70-350, 70-300, 70-250, 70-200, 70-150, 70-130, 70-110, 70-90, 90-500, 90-450, 90-400, 90-350, 90-300, 90-250, 90-200, 90-150, 90-130, 90-110, 110-500, 110-450, 110-400, 110-350, 110-300, 110-250, 110-200, 110-150, 110-130, 130-500, 130-450, 130-400, 130-350, 130-300, 130-250, 130-200, 130-150, 150-500, 150-450, 150-400, 150-350, 150-300, 150-250, 150-200, 200-500, 200-450, 200-400, 200-350, 200-300, 200-250, 250-500, 250-450, 250-400, 250-350, 250-300, 300-500, 300-450, 300-400, 300-350, 350-500, 350-450, 350-400, 400-500, 400-450, or 450-500 mg. For example, in a unit dose of an antiarrhythmic agent, the amount of antiarrhythmic agent, e.g., class I antiarrhythmic agent, can range about from 10 to about 80 mg. In some cases, class I antiarrhythmic agent is in the range of about 20 to about 60 mg.

In one aspect, provided herein are formulations for treatment of a heart condition, e.g., cardiac arrhythmia, e.g., atrial arrhythmia. The formulations can include the pharmaceutical compositions provided herein and a pharmaceutically acceptable carrier, excipient, diluent, or any other suitable component for the intended administration routes, such as oral or nasal inhalation, or intranasal spray administration. For example, the pharmaceutical composition can comprise neat particles of β1AR blocker and/or antiarrhythmic pharmaceutical agents (e.g., particles containing only the β1AR blocker and/or antiarrhythmic pharmaceutical agents), can comprise neat particles of β1AR blocker and/or antiarrhythmic pharmaceutical agents together with other particles, and/or can comprise particles comprising β1AR blocker and/or antiarrhythmic pharmaceutical agents and one or more active ingredients and/or one or more pharmaceutically acceptable excipients. Examples of pharmaceutically acceptable excipients include, but are not limited to, lipids, metal ions, surfactants, amino acids, carbohydrates, buffers, salts, polymers, and the like, and combinations thereof.

The therapeutically effective oral dose range of nebivolol can be 2.5 to 20 mg. Like many other β1AR blockers, oral administration of nebivolol can start with a low dose and titrate to a dose that is suitable for the individual patient.

In contrast, in the oral or nasal administration therapy, the dose can be a fixed small dose in range of 0.1 to 5.0 mg, as it is intended to be used acutely. The small dose can ensure that the β1 selectivity of nebivolol is preserved. In some instances, at much higher doses (greater than 10 mg) nebivolol can inhibit both β1- and β2-adrenergic receptors.

The therapy according to the present disclosure can markedly reduce the variability of absorption typically observed when delivered orally. Because of the fast absorption through the nasal mucosa or through the lungs the $T_{max}$ can be short, 0.5 to 5 minutes post inhalation.

The antiarrhythmic agent can be administered via any route, such as intravenous, intramuscular, transdermal, and oral delivery.

The pharmaceutical formulation according to one or more embodiments of the disclosure may comprise one or more β1AR blocker and/or antiarrhythmic pharmaceutical agents and, optionally, one or more other active ingredients and, optionally, one or more pharmaceutically acceptable excipients. For example, the pharmaceutical formulation may comprise particles of antiarrhythmic pharmaceutical agent with no other ingredients added (neat particles), may comprise neat particles of antiarrhythmic pharmaceutical agent together with other particles, and/or may comprise particles comprising antiarrhythmic pharmaceutical agent and one or more active ingredients and/or one or more pharmaceutically acceptable excipients.

In some instances, the β1AR blocker can be co-formulated with other antiarrhythmic agent as either solutions or suspensions for inhalation for treatment of cardiac arrhythmia. In some instances, the β1AR blocker and the other antiarrhythmic agent are formulated as individual formulations. In some instances, the formulations are co-packaged for sequential administration.

The β1AR blocker when administered concomitantly or sequentially via oral or nasal administration prior to or along with an antiarrhythmic therapy, e.g., administration of a Class 1c antiarrhythmic drug, can achieve one or more of the following results unmet by current commercially available products: rapid reduction in AV nodal transmission, reduction in ventricular rate, and suppression of atrial ectopy. The concomitant or sequential administration of β1AR blocker and other antiarrhythmic therapy according to the present disclosure can thereby prevent and/or ameliorate the potential life-threatening conditions (e.g., 1:1 AV conduction during atrial flutter). In some instances with the co-administration of class 1c agents, the delivery of β1AR blocker via oral or nasal administration can for instance, prevent or ameliorate 1:1 AV conduction during atrial flutter, a transient rhythm during conversion of AF to sinus rhythm that is typically associated with class 1c agents.

Because of the rapid reduction in AV nodal transmission, reduction in ventricular rate and suppression of atrial ectopy by the β1AR blocker, the ability of the class Ic antiarrhythmic drug to convert AF to normal sinus rhythm can increase with a reduced dose when compared to its use without the β1AR blocker.

In one aspect, also provided herein are kits for treatment of heart conditions via inhalation or intranasal administration. The kits can include one or more pharmaceutical agents, for instance, a β1AR blocker, an antiarrhythmic agent, or both, or some additional active agent(s) as described herein. In some cases, the kits include container for the pharmaceutical agents or compositions. In some cases, unit doses of the pharmaceutical agents as discussed above are provided in the kits. In some cases, the kits also include containers/receptacles for containing the pharmaceutical agents.

In some cases, the kits include separate containers/receptacles for containing the β1AR blocker and the class I antiarrhythmic agent, e.g., the two pharmaceutical agents can be administered separately or separate prior to administration step. In some cases, the kits include an aerosolization device for forming an aerosol of the pharmaceutical compositions. The aerosolization device can be any device as provided herein, and in some cases, used for inhalation of the pharmaceutical compositions. In some cases, the kits include nasal spray device as provided herein. In some cases, the pharmaceutical composition(s) is/are present in aerosol form in the kits. In some other cases, the kits include a single container for containing the β1AR blocker and the class I antiarrhythmic agent, e.g., the β1AR blocker and the class I antiarrhythmic agent are present in one single pharmaceutical composition, e.g., a single solution. The kits can further include instructions for methods of using the kit. The instructions can be presented in the form of a data sheet, a manual, in a piece of paper, printed on one or more containers or devices of the kit. Alternatively, the instructions can be provided in electronic form, for instance, available in a disc or online with a weblink available from the kit.

Examples of carbohydrates include, but are not limited to, monosaccharides, disaccharides, and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins, and maltodextrins. In some cases, carbohydrates such as cyclodextrins are used for stabilizing or increasing dissolution rate of the pharmaceutical agent in liquid solvent, e.g., water.

Non-limiting examples of lipids include phospholipids, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate.

In some cases, the phospholipid comprises a saturated phospholipid, such as one or more phosphatidylcholines. Exemplary acyl chain lengths are 16:0 and 18:0 (e.g., palmitoyl and stearoyl). The phospholipid content can be determined by the active agent activity, the mode of delivery, and other factors.

Phospholipids from both natural and synthetic sources can be used in varying amounts. When phospholipids are present, the amount is typically sufficient to coat the active agent(s) with at least a single molecular layer of phospholipid. In general, the phospholipid content ranges from about 5 wt % to about 99.9 wt %, such as about 20 wt % to about 80 wt %.

Generally, compatible phospholipids can comprise those that have a gel to liquid crystal phase transition greater than about 40° C., such as greater than about 60° C., or greater than about 80° C. The incorporated phospholipids can be relatively long chain (e.g., $C_{16}$-$C_{22}$) saturated lipids. Exemplary phospholipids useful in the present invention include, but are not limited to, phosphoglycerides such as dipalmitoylphosphatidylcholine, distearoylphosphatidylcholine, diarachidoylphosphatidylcholine, dibehenoylphosphatidylcholine, diphosphatidyl glycerols, short-chain phosphatidylcholines, hydrogenated phosphatidylcholine, E-100-3 (available from Lipoid KG, Ludwigshafen, Germany), long-chain saturated phosphatidylethanolamines, long-chain saturated phosphatidylserines, long-chain saturated phosphatidylglycerols, long-chain saturated phosphatidylinositols, phosphatidic acid, phosphatidylinositol, and sphingomyelin.

Examples of metal ions include, but are not limited to, divalent cations, including calcium, magnesium, zinc, iron, and the like. For instance, when phospholipids are used, the pharmaceutical composition can also comprise a polyvalent cation, as disclosed in WO 01/85136 and WO 01/85137, which are incorporated herein by reference in their entireties. The polyvalent cation can be present in an amount effective to increase the melting temperature ($T_m$) of the phospholipid such that the pharmaceutical composition exhibits a $T_m$ which is greater than its storage temperature ($T_m$) by at least about 20° C., such as at least about 40° C. The molar ratio of polyvalent cation to phospholipid can be at least about 0.05:1, such as about 0.05:1 to about 2.0:1 or about 0.25:1 to about 1.0:1. An example of the molar ratio of polyvalent cation:phospholipid is about 0.50:1. When the polyvalent cation is calcium, it can be in the form of calcium chloride. Although metal ion, such as calcium, is often included with phospholipid, none is required.

As noted above, the pharmaceutical composition can include one or more surfactants. For instance, one or more surfactants can be in the liquid phase with one or more being associated with solid particles or particles of the composition. By "associated with" it is meant that the pharmaceutical compositions can incorporate, adsorb, absorb, be coated with, or be formed by the surfactant. Surfactants include, but are not limited to, fluorinated and nonfluorinated compounds, such as saturated and unsaturated lipids, nonionic detergents, nonionic block copolymers, ionic surfactants, and combinations thereof. It should be emphasized that, in addition to the aforementioned surfactants, suitable fluorinated surfactants are compatible with the teachings herein and can be used to provide the desired preparations.

Examples of nonionic detergents include, but are not limited to, sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.), which is incorporated herein by reference in its entirety.

Examples of block copolymers include, but are not limited to, diblock and triblock copolymers of polyoxyethylene and polyoxypropylene, including poloxamer 188 (Pluronic™ F-68), poloxamer 407 (Pluronic™ F-127), and poloxamer 338.

Examples of ionic surfactants include, but are not limited to, sodium sulfosuccinate, and fatty acid soaps.

Examples of amino acids include, but are not limited to hydrophobic amino acids. Use of amino acids as pharmaceutically acceptable excipients is known in the art as disclosed in WO 95/31479, WO 96/32096, and WO 96/32149, which are incorporated herein by reference in their entireties.

Examples of buffers include, but are not limited to, tris or citrate.

Examples of acids include, but are not limited to, carboxylic acids.

Examples of salts include, but are not limited to, sodium chloride, salts of carboxylic acids, (e.g., sodium citrate, sodium ascorbate, magnesium gluconate, sodium gluconate, tromethamine hydrochloride, etc.), ammonium carbonate, ammonium acetate, ammonium chloride, and the like.

Examples of organic solids include, but are not limited to, camphor, and the like.

The pharmaceutical composition of one or more embodiments of the present invention can also include a biocompatible, such as biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery efficiency of the composition and/or the stability of the dispersions can be tailored to optimize the effectiveness of the antiarrhythmic pharmaceutical agent(s).

For solutions, the compositions can include one or more osmolality adjuster, such as sodium chloride. For instance, sodium chloride can be added to solutions to adjust the osmolality of the solution. In one or more embodiments, an aqueous composition consists essentially of the antiarrhythmic pharmaceutical agent, the osmolality adjuster, and water.

Solutions can also comprise a buffer or a pH adjusting agent, typically a salt prepared from an organic acid or base. Representative buffers comprise organic acid salts of citric acid, lactic acid, ascorbic acid, gluconic acid, carbonic acid, tartaric acid, succinic acid, acetic acid, or phthalic acid, Tris, tromethamine hydrochloride, or phosphate buffers. Thus, the buffers include citrates, phosphates, phthalates, and lactates.

Besides the above mentioned pharmaceutically acceptable excipients, it can be desirable to add other pharmaceutically acceptable excipients to the pharmaceutical composition to improve particle rigidity, production yield, emitted dose and deposition, shelf-life, and patient acceptance. Such optional pharmaceutically acceptable excipients include, but are not limited to: coloring agents, taste masking agents, buffers, hygroscopic agents, antioxidants, and chemical stabilizers. Further, various pharmaceutically acceptable excipients can be used to provide structure and form to the particle compositions (e.g., latex particles). In this regard, it will be appreciated that the rigidifying components can be removed using a post-production technique such as selective solvent extraction.

The pharmaceutical compositions of one or more embodiments of the present invention can lack taste. In this regard, although taste masking agents are optionally included within the composition, the compositions often do not include a taste masking agent and lack taste even without a taste masking agent.

The pharmaceutical compositions can also include mixtures of pharmaceutically acceptable excipients. For instance, mixtures of carbohydrates and amino acids are within the scope of the present invention.

The compositions of one or more embodiments of the present invention can take various forms, such as solutions, dry powders, reconstituted powders, suspensions, or dispersions comprising a non-aqueous phase, such as propellants (e.g., chlorofluorocarbon, hydrofluoroalkane).

The solutions of the present invention are typically clear. In this regard, many of the antiarrhythmic pharmaceutical agents of the present invention are water soluble.

In some embodiments, the isotonicity of the solution ranges from isotonic to physiologic isotonicity. Physiologic isotonicity is the isotonicity of physiological fluids.

The compositions can have a pH ranging from 3.5 to 8.0, such as from 4.0 to 7.5, or 4.5 to 7.0, or 5.0 to 6.5.

For dry powders, the moisture content can be less than about 15 wt %, such as less than about 10 wt %, less than about 5 wt %, less than about 2 wt %, less than about 1 wt %, or less than about 0.5 wt %. Such powders are described in WO 95/24183, WO 96/32149, WO 99/16419, WO 99/16420, and WO 99/16422, which are incorporated herein by reference in their entireties.

In one version, the pharmaceutical composition comprises antiarrhythmic pharmaceutical agent incorporated into a phospholipid matrix. The pharmaceutical composition can comprise phospholipid matrices that incorporate the active agent and that are in the form of particles that are hollow and/or porous microstructures, as described in the aforementioned WO 99/16419, WO 99/16420, WO 99/16422, WO 01/85136, and WO 01/85137, which are incorporated herein by reference in their entireties. The hollow and/or porous microstructures are useful in delivering the antiarrhythmic pharmaceutical agent to the lungs because the density, size, and aerodynamic qualities of the hollow and/or porous microstructures facilitate transport into the deep lungs during a user's inhalation. In addition, the phospholipid-based hollow and/or porous microstructures reduce the attraction forces between particles, making the pharmaceutical composition easier to deagglomerate during aerosolization and improving the flow properties of the pharmaceutical composition making it easier to process.

In one version, the pharmaceutical composition is composed of hollow and/or porous microstructures having a bulk density less than about 1.0 $g/cm^3$, less than about 0.5 $g/cm^3$, less than about 0.3 $g/cm^3$, less than about 0.2 $g/cm^3$, or less than about 0.1 $g/cm^3$. By providing low bulk density particles or particles, the minimum powder mass that can be filled into a unit dose container is reduced, which eliminates the need for carrier particles. That is, the relatively low density of the powders of one or more embodiments of the present invention provides for the reproducible administration of relatively low dose pharmaceutical compounds. Moreover, the elimination of carrier particles will potentially reduce throat deposition and any "gag" effect or coughing, since large carrier particles, e.g., lactose particles, will impact the throat and upper airways due to their size.

In some aspects, the present invention involves high rugosity particles. For instance, the particles can have a rugosity of greater than 2, such as greater than 3, or greater than 4, and the rugosity can range from 2 to 15, such as 3 to 10.

In one version, the pharmaceutical composition is in dry powder form and is contained within a unit dose receptacle which can be inserted into or near the aerosolization apparatus to aerosolize the unit dose of the pharmaceutical composition. This version is useful in that the dry powder form can be stably stored in its unit dose receptacle for a long period of time. In some examples, pharmaceutical compositions of one or more embodiments of the present invention can be stable for at least 2 years. In some versions, no refrigeration is required to obtain stability. In other versions, reduced temperatures, e.g., at 2-8° C., can be used to prolong stable storage. In many versions, the storage stability allows aerosolization with an external power source.

It will be appreciated that the pharmaceutical compositions disclosed herein can comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, some embodiments comprise approximately spherical shapes. However, collapsed, deformed or fractured particles are also compatible.

In one version, the antiarrhythmic pharmaceutical agent is incorporated in a matrix that forms a discrete particle, and the pharmaceutical composition comprises a plurality of the discrete particles. The discrete particles can be sized so that they are effectively administered and/or so that they are available where needed. For example, for an aerosolizable pharmaceutical composition, the particles are of a size that allows the particles to be aerosolized and delivered to a user's respiratory tract during the user's inhalation.

The matrix material can comprise a hydrophobic or a partially hydrophobic material. For example, the matrix material can comprise a lipid, such as a phospholipid, and/or a hydrophobic amino acid, such as leucine or tri-leucine. Examples of phospholipid matrices are described in WO 99/16419, WO 99/16420, WO 99/16422, WO 01/85136, and WO 01/85137 and in U.S. Pat. Nos. 5,874,064; 5,855,913; 5,985,309; 6,503,480; and 7,473,433, and in U.S. Published App. No. 20040156792, all of which are incorporated herein by reference in their entireties. Examples of hydrophobic amino acid matrices are described in U.S. Pat. Nos. 6,372,258; 6,358,530; and 7,473,433, which are incorporated herein by reference in their entireties.

When phospholipids are utilized as the matrix material, the pharmaceutical composition can also comprise a polyvalent cation, as disclosed in WO 01/85136 and WO 01/85137, which are incorporated herein by reference in their entireties.

According to another embodiment, release kinetics of the composition containing antiarrhythmic pharmaceutical agent(s) is controlled. According to one or more embodiments, the compositions of the present invention provide immediate release of the antiarrhythmic pharmaceutical agent(s). Alternatively, the compositions of other embodiments of the present invention can be provided as non-homogeneous mixtures of active agent incorporated into a matrix material and unincorporated active agent in order to provide desirable release rates of antiarrhythmic pharmaceutical agent According to this embodiment, antiarrhythmic pharmaceutical agents formulated using the emulsion-based manufacturing process of one or more embodiments of the present invention have utility in immediate release applications when administered to the respiratory tract. Rapid release is facilitated by: (a) the high specific surface area of the low density porous powders; (b) the small size of the drug crystals that are incorporated therein, and; (c) the low surface energy of the particles.

Alternatively, it can be desirable to engineer the particle matrix so that extended release of the active agent(s) is effected. This can be particularly desirable when the active agent(s) is rapidly cleared from the lungs or when sustained release is desired. For example, the nature of the phase behavior of phospholipid molecules is influenced by the nature of their chemical structure and/or preparation methods in spray-drying feedstock and drying conditions and other composition components utilized. In the case of spray-drying of active agent(s) solubilized within a small unilamellar vesicle (SUV) or multilamellar vesicle (MLV), the active agent(s) are encapsulated within multiple bilayers and are released over an extended time.

In contrast, spray-drying of a feedstock comprised of emulsion droplets and dispersed or dissolved active agent(s) in accordance with the teachings herein leads to a phospholipid matrix with less long-range order, thereby facilitating rapid release. While not being bound to any particular theory, it is believed that this is due in part to the fact that the active agent(s) are never formally encapsulated in the phospholipid, and the fact that the phospholipid is initially present on the surface of the emulsion droplets as a monolayer (not a bilayer as in the case of liposomes). The spray-dried particles prepared by the emulsion-based manufacturing process of one or more embodiments of the present invention often have a high degree of disorder. Also, the spray-dried particles typically have low surface energies, where values as low as 20 mN/m have been observed for spray-dried DSPC particles (determined by inverse gas chromatography). Small angle X-ray scattering (SAXS) studies conducted with spray-dried phospholipid particles have also shown a high degree of disorder for the lipid, with scattering peaks smeared out, and length scales extending in some instances only beyond a few nearest neighbors.

It should be noted that a matrix having a high gel to liquid crystal phase transition temperature is not sufficient in itself to achieve sustained release of the active agent(s). Having sufficient order for the bilayer structures is also important for achieving sustained release. To facilitate rapid release, an emulsion-system of high porosity (high surface area), and minimal interaction between the drug substance and phospholipid can be used. The pharmaceutical composition formation process can also include the additions of other composition components (e.g., small polymers such as Pluronic F-68; carbohydrates, salts, hydrotropes) to break the bilayer structure are also contemplated.

To achieve a sustained release, incorporation of the phospholipid in bilayer form can be used, especially if the active agent is encapsulated therein. In this case increasing the $T_m$ of the phospholipid can provide benefit via incorporation of divalent counterions or cholesterol. As well, increasing the interaction between the phospholipid and drug substance via the formation of ion-pairs (negatively charged active+steaylamine, positively charged active+phosphatidylglycerol) would tend to decrease the dissolution rate. If the active is amphiphilic, surfactant/surfactant interactions can also slow active dissolution.

The addition of divalent counterions (e.g., calcium or magnesium ions) to long-chain saturated phosphatidylcholines results in an interaction between the negatively charged phosphate portion of the zwitterionic headgroup and the positively charged metal ion. This results in a displacement of water of hydration and a condensation of the packing of the phospholipid lipid headgroup and acyl chains. Further, this results in an increase in the Tm of the phospholipid. The decrease in headgroup hydration can have profound effects on the spreading properties of spray-dried phospholipid particles on contact with water. A fully hydrated phosphatidylcholine molecule will diffuse very slowly to a dispersed crystal via molecular diffusion through the water phase. The process is exceedingly slow because the solubility of the phospholipid in water is very low (about $10^{-10}$ mol/L for DPPC). Prior art attempts to overcome this phenomenon include homogenizing the crystals in the presence of the phospholipid. In this case, the high degree of shear and radius of curvature of the homogenized crystals facilitates coating of the phospholipid on the crystals. In contrast, "dry" phospholipid powders according to one or more embodiments of this invention can spread rapidly when contacted with an aqueous phase, thereby coating dispersed crystals without the need to apply high energies.

For example, upon reconstitution, the surface tension of spray-dried DSPC/Ca mixtures at the air/water interface decreases to equilibrium values (about 20 mN/m) as fast as a measurement can be taken. In contrast, liposomes of DSPC decrease the surface tension (about 50 mN/m) very little over a period of hours, and it is likely that this reduction is due to the presence of hydrolysis degradation products such as free fatty acids in the phospholipid. Single-tailed fatty acids can diffuse much more rapidly to the air/water interface than can the hydrophobic parent compound. Hence, the addition of calcium ions to phosphatidylcholines can facilitate the rapid encapsulation of crystalline drugs more rapidly and with lower applied energy.

In another version, the pharmaceutical composition comprises low density particles achieved by co-spray-drying nanocrystals with a perfluorocarbon-in-water emulsion. The nanocrystals can be formed by precipitation and can, e.g., range in size from about 45 μm to about 80 μm. Examples of perfluorocarbons include, but are not limited to, perfluorohexane, perfluorooctyl bromide, perfluorooctyl ethane, perfluorodecalin, perfluorobutyl ethane.

In accordance with the teachings herein the particles can be provided in a "dry" state. That is, in one or more embodiments, the particles will possess a moisture content that allows the powder to remain chemically and physically stable during storage at ambient or reduced temperature and remain dispersible. In this regard, there is little or no change in primary particle size, content, purity, and aerodynamic particle size distribution.

As such, the moisture content of the particles is typically less than about 10 wt %, such as less than about 6 wt %, less than about 3 wt %, or less than about 1 wt %. The moisture content is, at least in part, dictated by the composition and is controlled by the process conditions employed, e.g., inlet temperature, feed concentration, pump rate, and blowing agent type, concentration and post drying. Reduction in bound water leads to significant improvements in the dispersibility and flowability of phospholipid based powders, leading to the potential for highly efficient delivery of powdered lung surfactants or particle composition comprising active agent dispersed in the phospholipid. The improved dispersibility allows simple passive DPI devices to be used to effectively deliver these powders.

Yet another version of the pharmaceutical composition includes particle compositions that can comprise, or can be partially or completely coated with, charged species that prolong residence time at the point of contact or enhance penetration through mucosae. For example, anionic charges are known to favor mucoadhesion while cationic charges can be used to associate the formed particle with negatively charged bioactive agents such as genetic material. The charges can be imparted through the association or incorporation of polyanionic or polycationic materials such as polyacrylic acids, polylysine, polylactic acid, and chitosan.

In some versions, the pharmaceutical composition comprises particles having a mass median diameter less than about 20 μm, such as less than about 10 μm, less than about 7 μm, or less than about 5 μm. The particles can have a mass median aerodynamic diameter ranging from about 1 μm to about 6 μm, such as about 1.5 μm to about 5 μm, or about 2 μm to about 4 μm. If the particles are too large, a larger percentage of the particles can not reach the lungs. If the particles are too small, a larger percentage of the particles can be exhaled.

Unit doses of the pharmaceutical compositions can be placed in a container. Examples of containers include, but are not limited to, syringes, capsules, blow fill seal, blisters, vials, ampoules, or container closure systems made of metal, polymer (e.g., plastic, elastomer), glass, or the like. For instance, the vial can be a colorless Type I borosilicate glass ISO 6R 10 mL vial with a chlorobutyl rubber siliconized stopper, and rip-off type aluminum cap with colored plastic cover.

The container can be inserted into an aerosolization device. The container can be of a suitable shape, size, and material to contain the pharmaceutical composition and to provide the pharmaceutical composition in a usable condition. For example, the capsule or blister can comprise a wall which comprises a material that does not adversely react with the pharmaceutical composition. In addition, the wall can comprise a material that allows the capsule to be opened to allow the pharmaceutical composition to be aerosolized. In one version, the wall comprises one or more of gelatin, hydroxypropyl methylcellulose (HPMC), polyethyleneglycol-compounded HPMC, hydroxyproplycellulose, agar, aluminum foil, or the like. In one version, the capsule can comprise telescopically adjoining sections, as described for example in U.S. Pat. No. 4,247,066 which is incorporated herein by reference in its entirety. The size of the capsule can be selected to adequately contain the dose of the pharmaceutical composition. The sizes generally range from size 5 to size 000 with the outer diameters ranging from about 4.91 mm to 9.97 mm, the heights ranging from about 11.10 mm to about 26.14 mm, and the volumes ranging from about 0.13 mL to about 1.37 mL, respectively. Suitable capsules are available commercially from, for example, Shionogi Qualicaps Co. in Nara, Japan and Capsugel in Greenwood, S.C. After filling, a top portion can be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

For solutions, the amount of the composition in the unit dose typically ranges from about 0.5 ml to about 15 ml, such as about 2 ml to about 15 ml, from about 3 ml to about 10 ml, about 4 ml to about 8 ml, or about 5 ml to about 6 ml.

The compositions of the present invention can be made by any of the various methods and techniques known and available to those skilled in the art.

For instance, a solution of antiarrhythmic pharmaceutical agent can be made using the following procedure. Typically, manufacturing equipment is sterilized before use. A portion of the final volume, e.g., 70%, of solvent, e.g., water for injection, can be added into a suitable container. Antiarrhythmic pharmaceutical agent can then be added. The antiarrhythmic pharmaceutical agent can be mixed until dissolved. Additional solvent can be added to make up the final batch volume. The batch can be filtered, e.g., through a 0.2 μm filter into a sterilized receiving vessel. Filling components can be sterilized before use in filling the batch into vials, e.g., 10 ml vials.

As an example, the above-noted sterilizing can include the following. A 5 liter type 1 glass bottle and lid can be placed in an autoclave bag and sterilized at elevated temperature, e.g., 121° C. for 15 minutes, using an autoclave. Similarly, vials can be placed into suitable racks, inserted into an autoclave bag, and sterilized at elevated temperature, e.g., 121° C. for 15 minutes, using an autoclave. Also similarly, stoppers can be placed in an autoclave bag and sterilized at elevated temperature, e.g., 121° C. for 15 minutes, using an autoclave. Before sterilization, sterilizing filters can be attached to tubing, e.g., a 2 mm length of 7 mm×13 mm silicone tubing. A filling line can be prepared by placed in an autoclave bag and sterilized at elevated temperature, e.g., 121° C. for 15 minutes, using an autoclave.

The above-noted filtration can involve filtration into a laminar flow work area. The receiving bottle and filters can be set up in the laminar flow work area.

The above-noted filling can also be conducted under laminar flow protection. The filling line can be unwrapped and placed into the receiving bottle. The sterilized vials and stoppers can be unwrapped under laminar flow protection. Each vial can be filled, e.g., to a target fill of 5 g, and stoppered. A flip off collar can be applied to each vial. The sealed vials can be inspected for vial leakage, correct overseals, and cracks.

For dry powders, the composition may be formed by spray drying, lyophilization, milling (e.g., wet milling, dry milling), and the like.

As an example, an antiarrhythmic can be prepared by lyophilizing the antiarrhythmic to form a powder for storage. The powder is then reconstituted prior to use. This technique can be used when the antiarrhythmic is unstable in solution.

In some cases, the lyophilized powder can be reconstituted in a suitable solvent such that the antiarrhythmic pharmaceutical agent is present at a concentration from about 1 mg/mL to about 60 mg/mL, such as 1 mg/mL to 5 mg/mL, 1 mg/ml to 10 mg/mL, 1 mg/ml to 15 mg/mL, 1 mg/mL to 20 mg/mL, 1 mg/mL to 25 mg/mL, 1 mg/mL to 30 mg/mL, 1 mg/mL to 35 mg/mL, 1 mg/mL to 40 mg/mL, 1 mg/mL to 45 mg/mL, 1 mg/mL to 50 mg/mL, 1 mg/mL to 55 mg/mL, 5 mg/ml to 10 mg/mL, 5 mg/ml to 15 mg/mL, 5 mg/mL to 20 mg/mL, 5 mg/mL to 25 mg/mL, 5 mg/mL to 30 mg/mL, 5 mg/mL to 35 mg/mL, 5 mg/mL to 40 mg/mL, 5 mg/mL to 45 mg/mL, 5 mg/mL to 50 mg/mL, 5 mg/mL to 55 mg/mL, 5 mg/mL to 60 mg/mL; 10 mg/ml to 15 mg/mL, 10 mg/mL to 20 mg/mL, 10 mg/mL to 25 mg/mL, 10 mg/mL to 30 mg/mL, 10 mg/mL to 35 mg/mL, 10 mg/mL to 40 mg/mL, 10 mg/mL to 45 mg/mL, 10 mg/mL to 50 mg/mL, 10 mg/mL to 55 mg/mL, 10 mg/mL to 60 mg/mL, 15 mg/mL to 20 mg/mL, 15 mg/mL to 25 mg/mL, 15 mg/mL to 30 mg/mL, 15 mg/mL to 35 mg/mL, 15 mg/mL to 40 mg/mL, 15 mg/mL to 45 mg/mL, 15 mg/mL to 50 mg/mL, 15 mg/mL to 55 mg/mL, 15 mg/mL to 60 mg/mL, 20 mg/mL to 25 mg/mL, 20 mg/mL to 30 mg/mL, 20 mg/mL to 35 mg/mL, 20 mg/mL to 40 mg/mL, 20 mg/mL to 45 mg/mL, 20 mg/mL to 50 mg/mL, 20 mg/mL to 55 mg/mL, 20 mg/mL to 60 mg/mL, 25 mg/mL to 30 mg/mL, 25 mg/mL to 35 mg/mL, 25 mg/mL to 40 mg/mL, 25 mg/mL to 45 mg/mL, 25 mg/mL to 50 mg/mL, 25 mg/mL to 55 mg/mL, 25 mg/mL to 60 mg/mL, 30 mg/mL to 35 mg/mL, 30 mg/mL to 40 mg/mL, 30 mg/mL to 45 mg/mL, 30 mg/mL to 50 mg/mL, 30 mg/mL to 55 mg/mL, 30 mg/mL to 60 mg/mL, 35 mg/mL to 40 mg/mL, 35 mg/mL to 45 mg/mL, 35 mg/mL to 50 mg/mL, 35 mg/mL to 55 mg/mL, 35 mg/mL to 60 mg/mL, 40 mg/mL to 45 mg/mL, 40 mg/mL to 50 mg/mL, 40 mg/mL to 55 mg/mL, 40 mg/mL to 60 mg/mL, 45 mg/mL to 50 mg/mL, 45 mg/mL to 55 mg/mL, 45 mg/mL to 60 mg/mL, 50 mg/mL to 55 mg/mL, 50 mg/mL to 60 mg/mL, or 55 mg/mL to 60 mg/mL. In yet other embodiments, after reconstitution of a lyophilized powder the antiarrhythmic pharmaceutical agent is present at about 30 mg/mL, 31 mg/mL, 32 mg/mL, 33 mg/mL, 34 mg/mL, 35 mg/mL, 36 mg/mL, 37 mg/ml, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, or 55 mg/mL.

The solvent for the solution to be lyophilized can comprise water. The solution can be excipient-free. For instance, the solution can be cryoprotectant-free.

In one or more embodiments, a suitable amount (e.g., 120 g per liter of final solution) of drug substance can be dissolved, e.g., in about the 75% of the theoretical total amount of water for injection under nitrogen bubbling. The dissolution time can be recorded and appearance can be evaluated.

Then, the dilution to the final volume with WFI can be carried out. Final volume can be checked. Density, pH, endotoxin, bioburden, and content by UV can be measured both before and after sterile filtration. The water content of the lyophilized powder is typically less than about 7 wt %, such as less than about 5 wt %, less than about 4 wt %, less than about 3 wt %, less than about 2 wt %, or less than about 1 wt %.

The powder is capable of being reconstituted with water at 25° C. and 1.0 atmosphere and with manual agitation, in less than about 60 seconds, such as less than about 30 seconds, less than about 15 seconds, or less than about 10 seconds. The powder typically has a large specific surface area that facilitates reconstitution. The specific surface area typically ranges from about 5 m$^2$/g to about 20 m$^2$/g, such as about 8 m$^2$/g to 15 m$^2$/g, or about 10 m$^2$/g to 12 m$^2$/g. Upon reconstitution with water, the antiarrhythmic pharmaceutical agent solution typically has a pH that ranges from about 2.5 to about 7, such as about 3 to about 6.

In spray drying, the preparation to be spray dried or feedstock can be any solution, coarse suspension, slurry, colloidal dispersion, or paste that may be atomized using the selected spray drying apparatus. In the case of insoluble agents, the feedstock may comprise a suspension as described above. Alternatively, a dilute solution and/or one or more solvents may be utilized in the feedstock. In one or more embodiments, the feed stock will comprise a colloidal system such as an emulsion, reverse emulsion microemulsion, multiple emulsion, particle dispersion, or slurry.

Pharmaceutical compositions useful in one or more embodiments of the present invention may alternatively be formed by lyophilization. Lyophilization is a freeze-drying process in which water is sublimed from the composition after it is frozen. The lyophilization process is often used because biologics and pharmaceuticals that are relatively unstable in an aqueous solution may be dried without exposure to elevated temperatures, and then stored in a dry state where there are fewer stability problems. With respect to one or more embodiments of the instant invention, such techniques are particularly compatible with the incorporation of peptides, proteins, genetic material and other natural and synthetic macromolecules in pharmaceutical compositions without compromising physiological activity. Lyophilized cake containing a fine foam-like structure can be micronized using techniques known in the art to provide particles of the desired size.

The pharmaceutical composition according to one or more embodiments of the invention may, if desired, contain a combination of antiarrhythmic pharmaceutical agent and one or more additional active agents. Examples of additional active agents include, but are not limited to, agents that may be delivered through the lungs.

Additional active agents may comprise, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The additional active agent, when administered by inhalation, may act locally or systemically.

The additional active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of additional active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., monoacylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFFR) gene, deoxyribonuclease (DNase), bactericidal/permeability increasing protein (BPI), anti-CMV antibody, 13-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Additional active agents for use in the invention can further include nucleic acids, as bare nucleic acid molecules, vectors, associated viral particles, plasmid DNA or RNA or other nucleic acid constructions of a type suitable for transfection or transformation of cells, e.g., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

When a combination of active agents is used, the agents may be provided in combination in a single species of pharmaceutical composition or individually in separate species of pharmaceutical compositions.

The amount of antiarrhythmic pharmaceutical agent in the pharmaceutical composition may vary. The amount of antiarrhythmic pharmaceutical agent(s) is typically at least about 5 wt %, such as at least about 10 wt %, at least about 20 wt %, at least about 30 wt %, at least about 40 wt %, at least about 50 wt %, at least about 60 wt %, at least about 70 wt %, or at least about 80 wt %, of the total amount of the pharmaceutical composition. The amount of antiarrhythmic pharmaceutical agent(s) generally varies between about 0.1 wt % to 100 wt %, such as about 5 wt % to about 95 wt %, about 10 wt % to about 90 wt %, about 30 wt % to about 80 wt %, about 40 wt % to about 70 wt %, or about 50 wt % to about 60 wt %.

EXEMPLARY EMBODIMENTS

[1] A method of treating a subject suffering from atrial arrhythmia, comprising: administering to said subject via inhalation or intranasal spray administration a therapeutically effective amount of a β1-selective adrenergic receptor blocker, thereby inducing cardioversion of said atrial arrhythmia in said subject and slowing atrioventricular (AV) node conduction during said cardioversion.

[2] A method of treating a subject suffering from atrial arrhythmia, comprising: administering to said subject via inhalation or intranasal spray administration a therapeutically effective amount of aβ1-selective adrenergic receptor blocker and a therapeutically effective amount of class I antiarrhythmic agent.

[3] The method of paragraph [2], wherein said administering induces cardioversion of said atrial arrhythmia in said subject.

[4] The method of paragraph [3], wherein said administering slows atrioventricular (AV) node conduction during said cardioversion.

[5] The method of any one of paragraphs [1] to [4], wherein a concentration of said β1-selective adrenergic receptor blocker in the coronary arterial circulation of the heart is between about 0.001 mg/L and about 0.1 mg/L at 2.5 minutes after said administering.

[6] The method of any one of paragraphs [1] to [4], wherein a concentration of said β1-selective adrenergic receptor blocker in the coronary arterial circulation of the heart is between about 0.01 mg/L and about 0.1 mg/L at 2.5 minutes after said administering.

[7] The method of any one of paragraphs [1] to [6], wherein a concentration of said β1-selective adrenergic receptor blocker in the coronary arterial circulation of the heart peaks at between about 0.001 mg/L and about 0.1 mg/L.

[8] The method of any one of paragraphs [1] to [6], wherein a concentration of said β1-selective adrenergic receptor blocker in the coronary arterial circulation of the heart peaks at between about 0.01 mg/L and about 0.1 mg/L.

[9] The method of any one of paragraphs [1] to [8], wherein said cardioversion restores sinus rhythm in said subject to normal within 30 min after said administering.

[10] The method of any one of paragraphs [1] to [8], wherein said cardioversion restores sinus rhythm in said subject to normal within 30 min after said administering.

[11] The method of any one of paragraphs [1] to [10], wherein said administering prolongs PR interval in said subject during said cardioversion as measured by electrocardiograph.

[12] The method of paragraph [11], wherein said PR interval in said subject is prolonged for at least about 2%, 3%, 4%, 5%, 6%, 8%, or 10%.

[13] The method of paragraph [11], wherein said PR interval in said subject is prolonged for at least about 5%.

[14] The method of paragraph [11], wherein said PR interval in said subject is prolonged for at least about 10%.

[15] The method of any one of paragraphs [1] to [14], wherein said administering reduces average ventricular rate in said subject during said cardioversion by at least about 10%.

[16] The method of paragraph [15], wherein said average ventricular rate during said cardioversion is reduced by at least about 15%.

[17] The method of paragraph [15], wherein said average ventricular rate during said cardioversion is reduced by at least about 20%.

[18] The method of paragraph [15], wherein said average ventricular rate during said cardioversion is reduced to about 110 beats per min (bpm).

[19] The method of paragraph [15], wherein said average ventricular rate during said cardioversion is reduced to at most about 110 beats per min (bpm).

[20] The method of paragraph [15], wherein said average ventricular rate during said cardioversion is reduced to at most about 80 bpm.

[21] The method of any one of paragraphs [1] to [20], wherein a change in ventricular contractility in said subject induced by said cardioversion is not substantially affected by said administering.

[22] The method of any one of paragraphs [1] to [21], wherein a mean arterial pressure of said subject is not substantially reduced by said administering.

[23] The method of any one of paragraphs [2] to [22], wherein said administering both of said therapeutically effective amount of said β1-selective adrenergic receptor blocker and said therapeutically effective amount of said class I antiarrhythmic agent induces cardioversion of said atrial arrhythmia in said subject faster than administering said therapeutically effective amount of said β1-selective adrenergic receptor blocker without a class I antiarrhythmic agent or said therapeutically effective amount of said class I antiarrhythmic agent in said subject without a β1-selective adrenergic receptor blocker.

[24] The method of any one of paragraphs [2] to [23], wherein said administering both of said therapeutically effective amount of said β1-selective adrenergic receptor blocker and said therapeutically effective amount of said class I antiarrhythmic agent induces a greater reduction in average ventricular rate during said cardioversion in said subject than administering said therapeutically effective amount of said β1-selective adrenergic receptor blocker without a class I antiarrhythmic agent or said therapeutically effective amount of said class I antiarrhythmic agent in said subject without a β1-selective adrenergic receptor blocker.

[25] The method of any one of paragraphs [1], or [5] to [24], wherein said administering comprises aerosolization of said therapeutically effective amount of said β1-selective adrenergic receptor blocker.

[26] The method of any one of paragraphs [2] to [24], wherein said administering comprises aerosolization of said therapeutically effective amount of said β1-selective adrenergic receptor blocker and said therapeutically effective amount of said class I antiarrhythmic agent.

[27] The method of paragraph [25] or [26], wherein said aerosolization comprises nebulization.

[28] The method of paragraph [27], wherein said aerosolization is performed by a jet nebulizer.

[29] The method of any one of paragraphs [25] to [28], wherein said aerosolization occurs at room temperature.

[30] The method of any one of paragraphs [25] to [29], wherein said aerosolization forms aerosols having particles having a mass median diameter of less than 10 nm.

[31] The method of any one of paragraphs [1] to [30], comprising administering about 1 mg to about 60 mg, about 1 mg to about 50 mg, about 1 mg to about 40 mg, about 1 mg to about 30 mg, about 1 mg to about 20 mg, about 1 mg to about 15 mg, 2 mg to about 15 mg, about 2 mg to about 10 mg, about 2 mg to about 7.5 mg, about 2 mg to about 5 mg, or about 2 mg to about 4 mg of said β1-selective adrenergic receptor blocker.

[32] The method of any one of paragraphs [1] to [30], comprising administering about 1 mg to about 10 mg of said β1-selective adrenergic receptor blocker.

[33] The method of any one of paragraphs [1] to [30], comprising administering about 1 mg to about 4 mg of said β1-selective adrenergic receptor blocker.

[34] The method of any one of paragraphs [1] to [33], wherein said β1-selective adrenergic receptor blocker is administered at a concentration of about 1 mg/mL to about 60 mg/mL, about 1 mg/mL to about 50 mg/mL, about 1 mg/mL to about 40 mg/mL, about 1 mg/mL to about 30 mg/mL, about 1 mg/mL to about 20 mg/mL, about 1 mg/mL to about 15 mg/mL, about 1 mg/mL to about 10 mg/mL, about 1 mg/mL to about 8 mg/mL, about 1 mg/mL to about 6 mg/mL, about 2 mg/mL to about 60 mg/mL, about 2 mg/mL to about 50 mg/mL, about 3 mg/mL to about 40 mg/mL, about 4 mg/mL to about 30 mg/mL, or about 5 mg/mL to about 20 mg/mL.

[35] The method of any one of paragraphs [1] to [33], wherein said β1-selective adrenergic receptor blocker is administered at a concentration of about 2 mg/mL to about 30 mg/mL.

[36] The method of any one of paragraphs [1] to [30], wherein said β1-selective adrenergic receptor blocker comprises metoprolol or a pharmaceutically acceptable salt or solvate thereof.

[37] The method of paragraph [36], wherein said β1-selective adrenergic receptor blocker comprises metoprolol tartrate.

[38] The method of paragraph [36] or [37], comprising administering about 1 mg to about 60 mg, about 1 mg to about 50 mg, about 1 mg to about 40 mg, about 1 mg to about 30 mg, about 1 mg to about 20 mg, about 1 mg to about 15 mg, 2 mg to about 15 mg, about 2 mg to about 10 mg, about 2 mg to about 7.5 mg, about 2 mg to about 5 mg, or about 2 mg to about 4 mg metoprolol or a pharmaceutically acceptable salt or solvate thereof.

[39] The method of paragraph [36] or [37], comprising administering about 1 mg to about 4 mg metoprolol or a pharmaceutically acceptable salt or solvate thereof.
[40] The method of paragraph [36] or [37], comprising administering at most about 2 mg metoprolol or a pharmaceutically acceptable salt or solvate thereof.
[41] The method of any one of paragraphs [36] to [40], wherein said metoprolol or a pharmaceutically acceptable salt or solvate thereof is administered at a concentration of about 1 mg/mL to about 60 mg/mL, about 1 mg/mL to about 50 mg/mL, about 1 mg/mL to about 40 mg/mL, about 1 mg/mL to about 30 mg/mL, about 1 mg/mL to about 20 mg/mL, about 1 mg/mL to about 15 mg/mL, about 1 mg/mL to about 10 mg/mL, about 1 mg/mL to about 8 mg/mL, about 1 mg/mL to about 6 mg/mL, about 2 mg/mL to about 60 mg/mL, about 2 mg/mL to about 50 mg/mL, about 3 mg/mL to about 40 mg/mL, about 4 mg/mL to about 30 mg/mL, or about 5 mg/mL to about 20 mg/mL.
[42] The method of any one of paragraphs [36] to [39], wherein said metoprolol or a pharmaceutically acceptable salt or solvate thereof is administered at a concentration of about 2 mg/mL to about 30 mg/mL.
[43] The method of any one of paragraphs [1] to [29], wherein said β1-selective adrenergic receptor blocker comprises nebivolol or a pharmaceutically acceptable salt or solvate thereof.
[44] The method of paragraph [43], comprising administering about 1 mg to about 30 mg, about 2 mg to about 30 mg, about 2 mg to about 20 mg, about 2 mg to about 15 mg, about 2 mg to about 10 mg, about 3 mg to about 30 mg, about 3 mg to about 20 mg, about 3 mg to about 15 mg, about 3 mg to about 10 mg, about 4 mg to about 10 mg, or about 4 mg to about 8 mg nebivolol or a pharmaceutically acceptable salt or solvate thereof.
[45] The method of paragraph [43], comprising administering about 1 mg to about 20 mg nebivolol or a pharmaceutically acceptable salt or solvate thereof.
[46] The method of paragraph [43], comprising administering at most about 2.5 mg nebivolol or a pharmaceutically acceptable salt or solvate thereof.
[47] The method of any one of paragraphs [43] to [46], wherein said nebivolol or a pharmaceutically acceptable salt or solvate thereof is administered at a concentration of about 2 mg/mL to about 30 mg/mL.
[48] The method of any one of paragraphs [43] to [47], wherein said nebivolol is a racemic mixture.
[49] The method of any one of paragraphs [43] to [47], wherein said nebivolol comprises at least about 70%, 75%, 80%, 85%, 90%, 95%, 98%, or 99% D-nebivolol.
[50] The method of any one of paragraphs [43] to [47], wherein said nebivolol comprises about 100% D-nebivolol.
[51] The method of any one of paragraphs [2] to [50], wherein said β1-selective adrenergic receptor blocker is administered prior to said class I antiarrhythmic agent.
[52] The method of paragraph [51], wherein said β1-selective adrenergic receptor blocker is administered up to about 90 minutes, about 75 minutes, about 60 minutes, about 45 minutes, about 30 minutes, about 20 minutes, about 15 minutes, about 10 minutes, or about 5 minutes earlier than said therapeutically effective amount of said class I antiarrhythmic agent.
[53] The method of paragraph [51], wherein said β1-selective adrenergic receptor blocker is administered up to about 30 minutes earlier than said therapeutically effective amount of said class I antiarrhythmic agent.
[54] The method of any one of paragraphs [23] to [50], wherein said β1-selective adrenergic receptor blocker is administered concurrently with said class I antiarrhythmic agent.
[55] The method of paragraph [54], wherein said β1-selective adrenergic receptor blocker is administered in a same liquid solution with said class I antiarrhythmic agent.
[56] The method of any one of paragraphs [23] to [55], wherein said class I antiarrhythmic agent comprises flecainide or a pharmaceutically acceptable salt or solvate thereof.
[57] The method of paragraph [56], comprising administering 20 mg to about 250 mg, about 20 mg to about 100 mg, about 20 mg to about 80 mg, about 20 mg to about 60 mg, about 30 mg to about 100 mg, or about 30 mg to about 50 mg flecainide or a pharmaceutically acceptable salt or solvate thereof.
[58] The method of paragraph [56], comprising administering about 20 mg to about 90 mg flecainide or a pharmaceutically acceptable salt or solvate thereof.
[59] The method of any one of paragraphs [56] to [58], wherein said flecainide or a pharmaceutically acceptable salt or solvate thereof is administered at a concentration of about 10 to about 90 mg/mL, about 10 to about 80 mg/mL, about 10 to about 70 mg/mL, about 20 to about 90 mg/mL, about 20 to about 80 mg/mL, about 20 to about 70 mg/mL, about 20 to about 60 mg/mL, or about 30 to about 50 mg/mL.
[60] The method of any one of paragraphs [56] to [58], wherein said flecainide or a pharmaceutically acceptable salt or solvate thereof is administered at a concentration of about 20 to about 60 mg/mL.
[61] The method of any one of paragraphs [56] to [60], wherein said class I antiarrhythmic agent comprises flecainide acetate.
[62] The method of any one of paragraphs [23] to [54], wherein said class I antiarrhythmic agent is selected from the group consisting of: class Ia, class Ib, and class Ic antiarrhythmic agent.
[63] The method of any one of paragraphs [23] to [54], wherein said class I antiarrhythmic agent is selected from the group consisting of: quinidine, procainamide, disopyramide, lidocaine, tocainide, phenytoin, moricizine, mexiletine, flecainide, propafenone, and moricizine.
[64] The method of any one of paragraphs [1] to [63], wherein said atrial arrhythmia comprises tachycardia.
[65] The method of paragraph [64], wherein said tachycardia is selected from the group consisting of: supraventricular tachycardia, paroxysmal supraventricular tachycardia, persistent atrial fibrillation, paroxysmal atrial fibrillation, acute episodes in persistent and permanent atrial fibrillation, atrial flutter, paroxysmal atrial flutter, and lone atrial fibrillation.
[66] The method of any one of paragraphs [1] to [65], wherein said atrial arrhythmia comprises atrial fibrillation.
[67] The method of any one of paragraphs [1] to [66], wherein said administering comprises 1 to 6 inhalations.
[68] The method of any one of paragraphs [1] to [67], wherein said subject is a human subject.
[69] The method of any one of paragraphs [1] to [68], wherein said method prevents atrial flutter from occurring concurrently with 1:1 AV node conduction ratio during said cardioversion.
[70] A kit comprising:
a first unit dose comprising a β1-selective adrenergic receptor blocker; and
a second unit dose comprising a class I antiarrhythmic agent.
[71] The kit of paragraph [70], wherein said first unit dose and said second unit dose are effective for treatment of atrial arrhythmia in a subject in need thereof when both are administered to said subject via inhalation or intranasal spray administration by inducing cardioversion of said atrial arrhythmia in said subject, and slowing atrioventricular (AV) node conduction during said cardioversion.

[72] The kit of paragraph [70] or [71], comprising:
a first container containing said first unit dose comprising said β1-selective adrenergic receptor blocker, and
a second container containing said second unit dose comprising said class I antiarrhythmic agent.

[73] The kit of any one of paragraphs [70] to [72], further comprising an aerosolization device.

[74] The kit of paragraph [73], wherein said aerosolization device is configured to deliver said β1-selective adrenergic receptor blocker and said class I antiarrhythmic agent concurrently via said aerosolization device.

[75] The kit of any one of paragraphs [70] to [74], wherein said first unit dose comprises about 1 mg to about 60 mg, about 1 mg to about 50 mg, about 1 mg to about 40 mg, about 1 mg to about 30 mg, about 1 mg to about 20 mg, about 1 mg to about 15 mg, 2 mg to about 15 mg, about 2 mg to about 10 mg, about 2 mg to about 7.5 mg, about 2 mg to about 5 mg, or about 2 mg to about 4 mg of said β1-selective adrenergic receptor blocker.

[76] The kit of any one of paragraphs [70] to [75], wherein said unit dose comprises about 1 mg to about 250 mg class I antiarrhythmic agent.

[77] The kit of any one of paragraphs [70] to [76], comprising about 1 mg to about 60 mg of said β1-selective adrenergic receptor blocker.

[78] The kit of any one of paragraphs [70] to [76], comprising about 1 mg to about 10 mg of said β1-selective adrenergic receptor blocker.

[79] The kit of any one of paragraphs [70] to [76], comprising about 1 mg to about 4 mg of said β1-selective adrenergic receptor blocker.

[80] The kit of any one of paragraphs [70] to [79], wherein said β1-selective adrenergic receptor blocker is in a liquid solution at a concentration of about 1 mg/mL to about 60 mg/mL, about 1 mg/mL to about 50 mg/mL, about 1 mg/mL to about 40 mg/mL, about 1 mg/mL to about 30 mg/mL, about 1 mg/mL to about 20 mg/mL, about 1 mg/mL to about 10 mg/mL, about 1 mg/mL to about 15 mg/mL, about 1 mg/mL to about 8 mg/mL, about 1 mg/mL to about 6 mg/mL, about 2 mg/mL to about 60 mg/mL, about 2 mg/mL to about 50 mg/mL, about 3 mg/mL to about 40 mg/mL, about 4 mg/mL to about 30 mg/mL, or about 5 mg/mL to about 20 mg/mL.

[81] The kit of any one of paragraphs [70] to [79], wherein said β1-selective adrenergic receptor blocker is in a liquid solution at a concentration of about 2 mg/mL to about 30 mg/mL.

[82] The kit of any one of paragraphs [70] to [76], wherein said β1-selective adrenergic receptor blocker comprises metoprolol or a pharmaceutically acceptable salt or solvate thereof.

[83] The kit of paragraph [82], wherein said β1-selective adrenergic receptor blocker comprises metoprolol tartrate.

[84] The kit of paragraph [82] or [83], comprising about 1 mg to about 60 mg, about 1 mg to about 50 mg, about 1 mg to about 40 mg, about 1 mg to about 30 mg, about 1 mg to about 20 mg, about 1 mg to about 15 mg, 2 mg to about 15 mg, about 2 mg to about 10 mg, about 2 mg to about 7.5 mg, about 2 mg to about 5 mg, or about 2 mg to about 4 mg metoprolol or a pharmaceutically acceptable salt or solvate thereof.

[85] The kit of paragraph [82] or [83], comprising about 1 mg to about 4 mg metoprolol or a pharmaceutically acceptable salt or solvate thereof.

[86] The kit of paragraph [82] or [83], comprising at most about 2 mg metoprolol or a pharmaceutically acceptable salt or solvate thereof.

[87] The kit of any one of paragraphs [82] to [86], wherein said metoprolol or a pharmaceutically acceptable salt or solvate thereof is in a liquid solution at a concentration of about 1 mg/mL to about 60 mg/mL, about 1 mg/mL to about 50 mg/mL, about 1 mg/mL to about 40 mg/mL, about 1 mg/mL to about 30 mg/mL, about 1 mg/mL to about 20 mg/mL, about 1 mg/mL to about 15 mg/mL, about 1 mg/mL to about 10 mg/mL, about 1 mg/mL to about 8 mg/mL, about 1 mg/mL to about 6 mg/mL, about 2 mg/mL to about 60 mg/mL, about 2 mg/mL to about 50 mg/mL, about 3 mg/mL to about 40 mg/mL, about 4 mg/mL to about 30 mg/mL, or about 5 mg/mL to about 20 mg/mL.

[88] The kit of any one of paragraphs [82] to [86], wherein said metoprolol or a pharmaceutically acceptable salt or solvate thereof is in a liquid solution at a concentration of about 2 mg/mL to about 30 mg/mL.

[89] The kit of any one of paragraphs [70] to [75], wherein said β1-selective adrenergic receptor blocker comprises nebivolol or a pharmaceutically acceptable salt or solvate thereof.

[90] The kit of paragraph [89], comprising about 1 mg to about 30 mg, about 2 mg to about 30 mg, about 2 mg to about 20 mg, about 2 mg to about 15 mg, about 2 mg to about 10 mg, about 3 mg to about 30 mg, about 3 mg to about 20 mg, about 3 mg to about 15 mg, about 3 mg to about 10 mg, about 4 mg to about 10 mg, or about 4 mg to about 8 mg nebivolol or a pharmaceutically acceptable salt or solvate thereof.

[91] The kit of paragraph [89], comprising about 1 mg to about 10 mg nebivolol or a pharmaceutically acceptable salt or solvate thereof.

[92] The kit of paragraph [89], comprising at most about 2.5 mg nebivolol or a pharmaceutically acceptable salt or solvate thereof.

[93] The kit of any one of paragraphs [89] to [92], wherein said nebivolol or a pharmaceutically acceptable salt or solvate thereof is in a liquid solution at a concentration of about 2 mg/mL to about 30 mg/mL.

[94] The kit of any one of paragraphs [89] to [93], wherein said nebivolol is a racemic mixture.

[95] The kit of any one of paragraphs [89] to [93], wherein said nebivolol comprises at least about 70%, 75%, 80%, 85%, 90%, 95%, 98%, or 99% D-nebivolol.

[96] The kit of any one of paragraphs [89] to [93], wherein said nebivolol comprises about 100% D-nebivolol.

[97] The kit of any one of paragraphs [70] to [96], wherein said class I antiarrhythmic agent comprises flecainide or a pharmaceutically acceptable salt or solvate thereof.

[98] The kit of any one of paragraphs [70] to [97], comprising about 10 mg to about 250 mg, about 20 mg to about 100 mg, about 20 mg to about 80 mg, about 20 mg to about 60 mg, about 30 mg to about 100 mg, or about 30 mg to about 50 mg flecainide or a pharmaceutically acceptable salt or solvate thereof.

[99] The kit of any one of paragraphs [70] to [97], comprising about 20 mg to about 90 mg flecainide or a pharmaceutically acceptable salt or solvate thereof.

[100] The kit of any one of paragraphs [70] to [99], wherein said flecainide or a pharmaceutically acceptable salt or solvate thereof has a concentration of about 10 to about 90 mg/mL, about 10 to about 80 mg/mL, about 10 to about 70 mg/mL, about 20 to about 90 mg/mL, about 20 to about 80 mg/mL, about 20 to about 70 mg/mL, about 20 to about 60 mg/mL, or about 30 to about 50 mg/mL.

[101] The kit of any one of paragraphs [70] to [100], wherein said flecainide or a pharmaceutically acceptable salt or solvate thereof has a concentration of about 20 to about 60 mg/mL.

[102] The kit of any one of paragraphs [70] to [101], wherein said class I antiarrhythmic agent comprises flecainide acetate.

[103] The kit of any one of paragraphs [70] to [96], wherein said class I antiarrhythmic agent is selected from the group consisting of: class Ia, class Ib, and class Ic antiarrhythmic agent.

[104] The kit of any one of paragraphs [70] to [96], wherein said class I antiarrhythmic agent is selected from the group consisting of: quinidine, procainamide, disopyramide, lidocaine, tocainide, phenytoin, moricizine, mexiletine, flecainide, propafenone, and moricizine.

[105] The kit of any one of paragraphs [70] to [104], wherein said first and second unit doses further comprise a pharmaceutically acceptable excipient or carrier.

[106] The kit of any one of paragraphs [70] to [105], wherein said first and second unit doses further comprise a pH buffer.

[107] The kit of paragraph [106], wherein said pH buffer is selected from the group consisting of: acetate, tris, citrate, phosphate, phthalate, and lactate.

[108] The kit of any one of paragraphs [73] to [107], wherein said aerosolization device is selected from the group consisting of: a nebulizer, a metered dose inhaler, a liquid dose instillation device, and a dry powder inhaler.

[109] The kit of any one of paragraphs [73] to [104], wherein said aerosolization device is a jet nebulizer.

[110] The kit of any one of paragraphs [73] to [109], wherein said aerosolization device is configured for aerosolization at room temperature.

[111] The kit of any one of paragraphs [73] to [110], wherein said aerosolization device is configured to form an aerosol having particles having a mass median diameter of less than 10 μm.

[112] The kit of any one of paragraphs [71] to [111], wherein said cardioversion restores sinus rhythm in said subject to normal within 10 min after said administering.

[113] The kit of any one of paragraphs [71] to [112], wherein said β1-selective adrenergic receptor blocker reaches about 0.001 mg/L and about 0.1 mg/L at 2.5 minutes in the coronary arterial circulation of the heart of said subject after being administered via inhalation or intranasal spray administration.

[114] The kit of any one of paragraphs [71] to [113], wherein said β1-selective adrenergic receptor blocker has a peak concentration of about 0.001 mg/L and about 0.1 mg/L in the coronary arterial circulation of the heart of said subject after being administered via inhalation or intranasal spray administration.

[115] The kit of any one of paragraphs [70] to [114], wherein said first unit dose and said second unit dose are effective for prolonging PR interval in said subject during said cardioversion as measured by electrocardiograph.

[116] The kit of paragraph [115], wherein said PR interval in said subject is prolonged for at least about 2%, 3%, 4%, 5%, 6%, 8%, or 10%.

[117] The kit of paragraph [115], wherein said PR interval in said subject is prolonged for at least about 5%.

[118] The kit of paragraph [115], wherein said PR interval in said subject is prolonged for at least about 10%.

[119] The kit of any one of paragraphs [70] to [118], wherein said first unit dose and said second unit dose are effective for reducing average ventricular rate in said subject during said cardioversion by at least about 10%.

[120] The kit of paragraph [119], wherein said average ventricular rate during said cardioversion is reduced by at least about 15%.

[121] The kit of paragraph [119], wherein said average ventricular rate during said cardioversion is reduced by at least about 20%.

[122] The kit of paragraph [119], wherein said average ventricular rate during said cardioversion is reduced to about 110 beats per min (bpm).

[123] The kit of paragraph [119], wherein said average ventricular rate during said cardioversion is reduced to at most about 110 beats per min (bpm).

[124] The kit of paragraph [119], wherein said average ventricular rate during said cardioversion is reduced to at most about 80 bpm.

[125] The kit of any one of paragraphs [71] to [124], wherein said atrial arrhythmia comprises tachycardia.

[126] The kit of paragraph [125], wherein said tachycardia is selected from the group consisting of: supraventricular tachycardia, paroxysmal supraventricular tachycardia, persistent atrial fibrillation, paroxysmal atrial fibrillation, acute episodes in persistent and permanent atrial fibrillation, atrial flutter, paroxysmal atrial flutter, and lone atrial fibrillation.

[127] The kit of any one of paragraphs [71] to [124], wherein said atrial arrhythmia comprises atrial fibrillation.

[128] A liquid pharmaceutical composition comprising a β1-selective adrenergic receptor blocker and a class I antiarrhythmic agent.

[129] The composition of paragraph [128], wherein said composition is effective for treatment of atrial arrhythmia in a subject in need thereof when administered to said subject via inhalation or intranasal spray administration by inducing cardioversion of said atrial arrhythmia in said subject, and slowing atrioventricular (AV) node conduction during said cardioversion.

[130] The composition of paragraph [128] or [129], wherein said composition is an aerosol.

[131] The composition of paragraph [130], wherein said aerosol comprises liquid droplets having a mass median aerodynamic diameter of less than 10 nm.

[132] The composition of paragraph [130] or [131], wherein said aerosol is not a condensation aerosol.

[133] The composition of any one of paragraphs [128] to [132], comprising about 1 mg to about 60 mg, about 1 mg to about 50 mg, about 1 mg to about 40 mg, about 1 mg to about 30 mg, about 1 mg to about 20 mg, about 1 mg to about 15 mg, 2 mg to about 15 mg, about 2 mg to about 10 mg, about 2 mg to about 7.5 mg, about 2 mg to about 5 mg, or about 2 mg to about 4 mg of said β1-selective adrenergic receptor blocker.

[134] The composition of any one of paragraphs [128] to [132], comprising about 1 mg to about 10 mg of said β1-selective adrenergic receptor blocker.

[135] The composition of any one of paragraphs [128] to [132], comprising about 1 mg to about 4 mg of said β1-selective adrenergic receptor blocker.

[136] The composition of any one of paragraphs [128] to [135], wherein said β1-selective adrenergic receptor blocker has a concentration of about 1 mg/mL to about 60 mg/mL, about 1 mg/mL to about 50 mg/mL, about 1 mg/mL to about 40 mg/mL, about 1 mg/mL to about 30 mg/mL, about 1 mg/mL to about 20 mg/mL, about 1 mg/mL to about 15 mg/mL, about 1 mg/mL to about 10 mg/mL, about 1 mg/mL to about 8 mg/mL, about 1 mg/mL to about 6 mg/mL, about 2 mg/mL to about 60 mg/mL, about 2 mg/mL to about 50 mg/mL, about 3 mg/mL to about 40 mg/mL, about 4 mg/mL to about 30 mg/mL, or about 5 mg/mL to about 20 mg/mL.

[137] The composition of any one of paragraphs [128] to [135], wherein said β1-selective adrenergic receptor blocker has a concentration of about 2 mg/mL to about 30 mg/mL.

[138] The composition of any one of paragraphs [128] to [132], wherein said β1-selective adrenergic receptor blocker comprises metoprolol or a pharmaceutically acceptable salt or solvate thereof.

[139] The composition of paragraph [138], wherein said β1-selective adrenergic receptor blocker comprises metoprolol tartrate.

[140] The composition of paragraph [138] or [139], comprising about 1 mg to about 60 mg, about 1 mg to about 50 mg, about 1 mg to about 40 mg, about 1 mg to about 30 mg, about 1 mg to about 20 mg, about 1 mg to about 15 mg, 2 mg to about 15 mg, about 2 mg to about 10 mg, about 2 mg to about 7.5 mg, about 2 mg to about 5 mg, or about 2 mg to about 4 mg metoprolol or a pharmaceutically acceptable salt or solvate thereof.

[141] The composition of paragraph [138] or [139], comprising about 1 mg to about 4 mg metoprolol or a pharmaceutically acceptable salt or solvate thereof.

[142] The composition of paragraph [138] or [139], comprising at most about 2 mg metoprolol or a pharmaceutically acceptable salt or solvate thereof.

[143] The composition of any one of paragraphs [138] to [142], wherein said metoprolol or a pharmaceutically acceptable salt or solvate thereof has a concentration of about 1 mg/mL to about 60 mg/mL, about 1 mg/mL to about 50 mg/mL, about 1 mg/mL to about 40 mg/mL, about 1 mg/mL to about 30 mg/mL, about 1 mg/mL to about 20 mg/mL, about 1 mg/mL to about 15 mg/mL, about 1 mg/mL to about 10 mg/mL, about 1 mg/mL to about 8 mg/mL, about 1 mg/mL to about 6 mg/mL, about 2 mg/mL to about 60 mg/mL, about 2 mg/mL to about 50 mg/mL, about 3 mg/mL to about 40 mg/mL, about 4 mg/mL to about 30 mg/mL, or about 5 mg/mL to about 20 mg/mL.

[144] The composition of any one of paragraphs [138] to [142], wherein said metoprolol or a pharmaceutically acceptable salt or solvate thereof has at a concentration of about 2 mg/mL to about 30 mg/mL.

[145] The composition of paragraph [128] or [129], wherein said β1-selective adrenergic receptor blocker comprises nebivolol or a pharmaceutically acceptable salt or solvate thereof.

[146] The composition of paragraph [145], comprising about 1 mg to about 30 mg, about 2 mg to about 30 mg, about 2 mg to about 20 mg, about 2 mg to about 15 mg, about 2 mg to about 10 mg, about 3 mg to about 30 mg, about 3 mg to about 20 mg, about 3 mg to about 15 mg, about 3 mg to about 10 mg, about 4 mg to about 10 mg, or about 4 mg to about 8 mg nebivolol or a pharmaceutically acceptable salt or solvate thereof.

[147] The composition of paragraph [145], comprising about 1 mg to about 10 mg nebivolol or a pharmaceutically acceptable salt or solvate thereof.

[148] The composition of paragraph [145], comprising at most about 2.5 mg nebivolol or a pharmaceutically acceptable salt or solvate thereof.

[149] The composition of any one of paragraphs [145] to [148], wherein said nebivolol or a pharmaceutically acceptable salt or solvate thereof has a concentration of about 2 mg/mL to about 30 mg/mL.

[150] The composition of any one of paragraphs [145] to [149], wherein said nebivolol is a racemic mixture.

[151] The composition of any one of paragraphs [145] to [149], wherein said nebivolol comprises at least about 70%, 75%, 80%, 85%, 90%, 95%, 98%, or 99% D-nebivolol.

[152] The composition of any one of paragraphs [145] to [149], wherein said nebivolol comprises about 100% D-nebivolol.

[153] The composition of any one of paragraphs [128] to [152], wherein said class I antiarrhythmic agent comprises flecainide or a pharmaceutically acceptable salt or solvate thereof.

[154] The composition of any one of paragraphs [128] to [153], comprising about 20 mg to about 250 mg, about 20 mg to about 100 mg, about 20 mg to about 80 mg, about 20 mg to about 60 mg, about 30 mg to about 100 mg, or about 30 mg to about 50 mg flecainide or a pharmaceutically acceptable salt or solvate thereof.

[155] The composition of any one of paragraphs [128] to [153], comprising about 20 mg to about 90 mg flecainide or a pharmaceutically acceptable salt or solvate thereof.

[156] The composition of any one of paragraphs [128] to [155], wherein said flecainide or a pharmaceutically acceptable salt or solvate thereof has a concentration of about 10 to about 90 mg/mL, about 10 to about 80 mg/mL, about 10 to about 70 mg/mL, about 20 to about 90 mg/mL, about 20 to about 80 mg/mL, about 20 to about 70 mg/mL, about 20 to about 60 mg/mL, or about 30 to about 50 mg/mL.

[157] The composition of any one of paragraphs [128] to [156], wherein said flecainide or a pharmaceutically acceptable salt or solvate thereof has a concentration of about 20 to about 60 mg/mL.

[158] The composition of any one of paragraphs [128] to [157], wherein said class I antiarrhythmic agent comprises flecainide acetate.

[159] The composition of any one of paragraphs [128] to [152], wherein said class I antiarrhythmic agent is selected from the group consisting of: class Ia, class Ib, and class Ic antiarrhythmic agent.

[160] The composition of any one of paragraphs [128] to [152], wherein said class I antiarrhythmic agent is selected from the group consisting of: quinidine, procainamide, disopyramide, lidocaine, tocainide, phenytoin, moricizine, mexiletine, flecainide, propafenone, and moricizine.

[161] The composition of any one of paragraphs [128] to [160], further comprising a pharmaceutically acceptable excipient or carrier.

[162] The composition of any one of paragraphs [128] to [161], further comprising a pH buffer.

[163] The composition of paragraph [162], wherein said pH buffer is selected from the group consisting of: acetate, tris, citrate, phosphate, phthalate, and lactate.

[164] The composition of any one of paragraphs [129] to [163], wherein said cardioversion restores sinus rhythm in said subject to normal within 10 min after said administering.

[165] The composition of any one of paragraphs [129] to [164], wherein said β1-selective adrenergic receptor blocker reaches about 0.001 mg/L and about 0.1 mg/L at 2.5 minutes in the coronary arterial circulation of the heart of said subject after being administered via inhalation or intranasal spray administration.

[166] The composition of any one of paragraphs [129] to [164], wherein said β1-selective adrenergic receptor blocker reaches about 0.01 mg/L and about 0.1 mg/L at 2.5 minutes in the coronary arterial circulation of the heart is between after being administered via inhalation or intranasal spray administration.

[167] The composition of any one of paragraphs [129] to [166], wherein said β1-selective adrenergic receptor blocker has a peak concentration of about 0.001 mg/L and about 0.1 mg/L in the coronary arterial circulation of the heart of said subject after being administered via inhalation or intranasal spray administration.

[168] The composition of any one of paragraphs [129] to [166], wherein said β1-selective adrenergic receptor blocker has a peak concentration of about 0.01 mg/L and about 0.1 mg/L in the coronary arterial circulation of the heart of said subject after being administered via inhalation or intranasal spray administration.

[169] The composition of any one of paragraphs [129] to [168], wherein said composition is effective for prolonging PR interval in said subject during said cardioversion as measured by electrocardiograph.

[170] The composition of paragraph [169], wherein said PR interval in said subject is prolonged for at least about 2%, 3%, 4%, 5%, 6%, 8%, or 10%.

[171] The composition of paragraph [170], wherein said PR interval in said subject is prolonged for at least about 5%.

[172] The composition of paragraph [170], wherein said PR interval in said subject is prolonged for at least about 10%.

[173] The composition of any one of paragraphs [129] to [172], wherein said composition is effective for reducing average ventricular rate in said subject during said cardioversion by at least about 10%.

[174] The composition of paragraph [173], wherein said average ventricular rate during said cardioversion is reduced by at least about 15% or 20%.

[175] The composition of paragraph [173] or [174], wherein said average ventricular rate during said cardioversion is reduced to about 110 beats per min (bpm).

[176] The composition of paragraph [173] or [174], wherein said average ventricular rate during said cardioversion is reduced to at most about 110 beats per min (bpm).

[177] The composition of paragraph [173] or [174], wherein said average ventricular rate during said cardioversion is reduced to at most about 80 bpm.

[178] The composition of any one of paragraphs [129] to [177], wherein said atrial arrhythmia comprises tachycardia.

[179] The composition of paragraph [178], wherein said tachycardia is selected from the group consisting of: supraventricular tachycardia, paroxysmal supraventricular tachycardia, persistent atrial fibrillation, paroxysmal atrial fibrillation, acute episodes in persistent and permanent atrial fibrillation, atrial flutter, paroxysmal atrial flutter, and lone atrial fibrillation.

[180] The composition of any one of paragraphs [129] to [179], wherein said atrial arrhythmia comprises atrial fibrillation.

[181] A method of treating or preventing a heart condition, comprising:
administering, by oral or nasal administration, an effective amount of a selective β-1 adrenergic receptor (β1AR) blocker to a subject in need thereof, such that the selective β1AR first enters the heart through a pulmonary vein to the left atrium.

[182] The method of paragraph [181], wherein the oral or nasal administration comprises oral inhalation, nasal inhalation, or intranasal spray administration.

[183] The method of paragraph [181] or [182], wherein the heart condition comprises tachycardia, atrial ectopy, or both.

[184] The method of any one of paragraphs [181]-[183], wherein the tachycardia comprises sinus tachycardia, atrial fibrillation, atrial flutter, AV nodal reentrant tachycardia, accessory pathway mediated tachycardia, atrial tachycardia, multifocal atrial tachycardia, junctional tachycardia, ventricular tachycardia, supraventricular tachycardia, or any combination thereof.

[185] The method of any one of paragraphs [181]-[184], wherein the heart condition arises during cardioversion of atrial fibrillation.

[186] The method of any one of paragraphs [181]-[185], wherein the selective β1AR blocker comprises atenolol, acebutolol, bisoprolol, betaxolol, celiprolol, esmolol, metoprolol, nebivolol, or any combination thereof.

[187] The method of any one of paragraphs [181]-[186], wherein the selective β1AR blocker comprises nebivolol.

[188] The method of paragraph [187], wherein more than 50%, 60%, 70%, 80%, 90%, 95%, 96%, 97%, 97.5%, 98%, 98.5%, 99%, 99.5%, 99.6%, 99.7%, 99.8%, or 99.9% of the nebivolol is d-nebivolol.

[189] The method of paragraph [187], wherein the nebivolol is d-nebivolol.

[190] The method of any one of paragraphs [181]-[189], wherein the effective amount of the β1AR is in a range of from 1 μg to 10 μg, from 1 μg to 100 μg, from 1 μg to 1 mg, from 1 μg to 10 mg, from 1 μg to 50 mg, from 10 μg to 100 μg, from 10 μg to 1 mg, from 10 μg to 10 mg, from 10 μg to 50 mg, from 100 μg to 1 mg, from 100 μg to 10 mg, or from 100 μg to 50 mg.

[191] The method of any one of paragraphs [181]-[190], further comprising: inducing cardioversion in the subject.

[192] The method of paragraph [191], wherein the administering the selective β1AR blocker prevents or suppresses tachycardia, atrial ectopy, or both.

[193] The method of paragraph [191] or [192], wherein the administering takes place prior to the induction of the cardioversion.

[194] The method of paragraph [191] or [192], wherein the administering takes place from 1 to 30, from 5 to 30, from 1 to 15, from 5 to 15, from 1 to 10, or from 5 to 10 minutes prior to the induction of the cardioversion.

[195] The method of paragraph [191] or [192], wherein the administering and the inducing take place concomitantly.

[196] The method of any one of paragraphs [191]-[195], wherein the induction of the cardioversion comprises applying an electric current to the subject.

[197] The method of any one of paragraphs [191]-[196], wherein the induction of the cardioversion comprises administering an effective amount of an antiarrhythmic agent to the patient.

[198] The method of paragraph [197], wherein the antiarrhythmic agent comprises a Class Ic antiarrhythmic agent.

[199] The method of paragraph [197], wherein the antiarrhythmic agent comprises flecainide.

[200] The method of any one of paragraphs [197]-[199], wherein the administering the antiarrhythmic agent comprises administering the antiarrhythmic agent via intravenous, intracardiac, intramuscular, transdermal, oral, nasal, or intranasal spray delivery.

[201] The method of any one of paragraphs [197]-[200], wherein the administering the antiarrhythmic agent comprises delivering the antiarrhythmic agent via intravenous (IV) or intracardiac infusion.

[202] The method of any one of paragraphs [197]-[201], wherein the administering the antiarrhythmic agent comprises delivering a Class Ia, Ib, Ic, II, III, IV, or V antiarrhythmic agent, or any combination thereof.

[203] The method of any one of paragraphs [197]-[202], wherein the administering the antiarrhythmic agent comprises delivering vernakalant, flecainide, ibutilide or defetilide.

[204] The method of any one of paragraphs [197]-[203], wherein the effective amount of the antiarrhythmic agent is in a range of 1-50, 5-50, 10-50, or 5-25 mg.

[205] A pharmaceutical formulation comprising β1AR blocker formulated for oral or nasal administration, wherein via oral or nasal administration, the β1AR blocker first enters the heart through a pulmonary vein to the left atrium.

[206] The pharmaceutical formulation of paragraph [205], wherein the β1AR blocker comprises nebivolol.

[207] The pharmaceutical formulation of paragraph [206], wherein at least 50%, 60%, 70%, 80%, 90%, 95%, 96%, 97%, 97.5%, 98%, 98.5%, 99%, 99.5%, 99.6%, 99.7%, 99.8%, or 99.9% of the nebivolol is d-nebivolol.

[208] The pharmaceutical formulation of paragraph [206], wherein the nebivolol is d-nebivolol.

[209] The pharmaceutical formulation of any one of paragraphs [205]-[208], further comprising an antiarrhythmic agent formulated for oral inhalation, nasal inhalation, or intranasal spray administration.

[210] The pharmaceutical formulation of paragraph [209], wherein the antiarrhythmic agent comprises class Ic antiarrhythmic agent.

[211] The pharmaceutical formulation of paragraph [209] or [210], wherein the antiarrhythmic agent comprises flecainide.

[212] A kit, comprising: the pharmaceutical formulation of any one of paragraphs [205]-[211], and instructions of use.

[213] A kit, comprising: the pharmaceutical formulation of any one of paragraphs [205]-[208], a second pharmaceutical formulation comprising an antiarrhythmic agent, and instructions of use.

[214] The kit of paragraph [213], wherein the second pharmaceutical formulation comprises vernakalant, flecainide, ibutilide, or defetilide, that is formulated for IV delivery, oral pill or tablet, oral inhalation, nasal inhalation, or intranasal spray administration.

[215] The kit of any one of paragraph [212]-[214], further comprising an inhaler for administration of the pharmaceutical formulation.

[216] A method, comprising:
inducing cardioversion of atrial fibrillation in a patient in need thereof; and
administering, by oral or nasal administration, an effective amount of a selective β1AR blocker to the patient, such that the selective β1AR first enters the heart through the pulmonary vein to the left atrium, thereby preventing or suppressing tachycardia, atrial ectopy, or both, associated with the cardioversion.

EXAMPLE

The following examples are offered by way of illustration, not by way of limitation.

Example 1: Nebivolol and Flecainide

When nebivolol and flecainide are used either sequentially or concomitantly via oral inhalation, nasal inhalation, or intranasal spray administration in the management of acute AF, the mechanism of action of both the β1AR blocker and the Na+ channel blocker is synergistic in the sense that the β1AR blocker due to its cardioselectivity 'prepares' the heart, that is, suppresses the arrhythmogenic atrial foci driven by sympathetic activity resulting in greater efficacy and slowing AV nodal conduction resulting in slower ventricular rate and safer cardioversion. The suppression of arrhythmogenic atrial foci and slowing of AV nodal conduction should render cardioversion of AF by flecainide more efficacious and safer.

The inhaled dose of Nebivolol will be used in a range of 0.1 to 2.0 mg and the estimated heart dose of flecainide will be in the range of 5-75 mg.

Because of the fast absorption through the mucosa or the lungs, the $T_{max}$ for both drugs can be short. $T_{max}$ can be 0.5 to 5 minutes post inhalation if administered concomitantly, and 0.5 to 5 minutes individually if administered sequentially with a gap of 5-15 minutes between the two drugs.

The drugs can be co-formulated as either solutions or suspensions for oral inhalation, nasal inhalation, or intranasal spray administration or as individual formulations for the same purpose, which can be co-packaged for sequential administration.

Example 2: Formulation of Nebivolol for Nasal Inhalation, Intranasal Spray Administration, or Oral Inhalation The formulation of nebivolol for nasal inhalation, intranasal spray administration, or oral inhalation can be hampered by its low water solubility. Nebivolol hydrochloride is soluble in methanol, dimethylsulfoxide, and N,N-dimethylformamide, sparingly soluble in ethanol, propylene glycol, and polyethylene glycol, and very slightly soluble in hexane, dichloromethane, and methylbenzene.

The formulation of nebivolol for inhalation can be achieved in at least one or more of the following different ways:

use of suspension metered dose inhalers (MDIs): the suspension micronized nebivolol in 134- or 228-HFA would enable the delivery of nebivolol for inhalation in the 0.1 to 0.5 mg range per actuation of the MDI. Technologies such as lipid-based porous particles can be used to create stable compositions with drug crystals in HFA propellants;

formulation of nebivolol as a dry powder suitable for oral inhalation, nasal inhalation, or intranasal administration: this type of formulations would enable the delivery of this drug using commercially available Dry Powder Inhalers (DPI's), or Dry Powder Nebulizers (DPN's) which can be used for oral inhalation, nasal inhalation or intranasal administration. Inhalation use dry powders can be created by micronization and spray drying, among other techniques. Excipients such as amino acids, sugars and lipids can be used to optimize the dispersibility of these powders, making them suitable for inhalation; and formulation of nebivolol as a microemulsion, using oils, surfactants and co-surfactants: this type of formulations would enhance the solubility of nebivolol in water, enabling its delivery using commercially available jet or vibrating mesh nebulizer technologies, which can be used for oral inhalation, nasal inhalation or intranasal administration. Examples of oils that can be used include soya bean oil, castor oil, olive oil, labra 11 1944 and oleic acid. Surfactants and co-surfactants include Tween 20 and 80, Cremophor RH 40, PEG, Kolliphor and Labrasol Example 3: Slowing AV Nodal Transmission by Nebivolol and/or its D-Enantiomer in Presence of Epinephrine (EPI)

In a pig or dog model of AF, EPI is first intravenously injected to mimic high sympathetic tone, and to increase AV nodal transmission, thereby increasing ventricular rate. Once ventricular rate is increased, administer nebivolol or its d-enantiomer, at 2 to 3 doses, via intratracheal instillation to slow ventricular rate. ECG is recorded to monitor the heart rate change in response to the treatment.

Example 4: Suppression of EPI-Induced Atrial Premature Beats by Nebivolol and/or its D-Enantiomer In a pig model of AF induced by intrapericardial acetylcholine followed by IV EPI, induction of AF is preceded by atrial premature beats (APB). The objective will be to demonstrate that nebivolol or its d-enantiomer, given via intratracheal instillation, by suppressing the APBs caused by EPI prevents and/or reduces the probability of induction of AF.

Example 5. Electropharmacological Effects of Intratracheal (IT) Administration of Beta Blocker Metoprolol in Pig Models with Induced Atrial Fibrillation In this example, effects of pulmonary delivery of beta blocker metoprolol were tested in pig models of induced atrial fibrillation. It was hypothesized that when delivered via the pulmonary route by intratracheal instillation as a first pass bolus, metoprolol could reach an abrupt, transient rise in its plasma concentration, and could result in AF termination by suppression of atrial arrhythmogenic foci and reentrant circuits. It was hypothesized that metoprolol could reduce ventricular rate during AF. Furthermore, it was hypothesized that the negative inotropic and hemodynamic effects of beta-blockade would be mitigated using the rapid intratracheal route, at least partially, due to reduced exposure time of the ventricular myocardium to the negative inotropic actions of metoprolol.

Experimental Preparation

Experiments described herein (e.g., Examples 5-7) complied with the National Institutes of Health Guide for the Care and Use of Laboratory Animals as well as the Declaration of Helsinki. The protocol was approved by the institutional animal use committee of Beth Israel Deaconess Medical Center (Boston Mass.). The investigations were conducted in male Yorkshire pigs weighing 46±1.8 kg. The animals were preanesthetized with telazol (4.7 mg/kg, intramuscular) and subsequently were further anesthetized using alpha-chloralose (80-mg/kg IV bolus followed by 24-mg/kg/h continuous IV infusion). The pigs were intubated and ventilated at a constant rate of 12 breaths/min and tidal volume of 400 ml per stroke.

The catheters were positioned under fluoroscopic control. Electrograms were recorded from a decapolar electrode catheter positioned in the LV. Mean arterial pressure (MAP) was continuously recorded from a femoral arterial sheath. LV blood pressure was continuously monitored from a pigtail catheter. A catheter was introduced into the pericardial space via the right atrial appendage for delivery of intrapericardial acetylcholine. Atrial pacing at 160 beats/min was accomplished by delivering electrical stimuli to the right atrial catheter electrodes. Electrograms were monitored using a Prucka CardioLab workstation (GE Medical Systems, Milwaukee Wis.) from atrial and ventricular sites. For intratracheal instillation of metoprolol solution or sterile water, a 5 Fr angiography catheter was introduced into the trachea via the endotracheal tube, extending ~1 cm past the tube, and its tip was positioned under fluoroscopy at the tracheal carina level.

Reagents and Chemical Analysis

Metoprolol solutions of 0.2 mg/kg for intratracheal instillation were prepared by dilution of stock solution of 15.3 mg/ml in saline, originally obtained from metoprolol in powder form by dilution in dimethyl sulfoxide (DMSO). Plasma samples were analyzed using a high-performance liquid chromatography tandem mass spectrometric assay at Climax Laboratories, Inc. (San Jose Calif.).

Study Protocols

AF was induced with 1 mL of a 102.5 mM solution of acetylcholine bolus delivered through the pericardial catheter, followed by saline flush (2 mL). Burst pacing at a cycle length of 178 ms was performed at 1 minute after intrapericardial administration of ACh. After AF initiation, lavage was carried out with 20 ml of saline.

For the intratracheal instillation of metoprolol (2 ml of 0.2 mg/kg concentration followed by 3 ml of air in a 5 ml syringe), the agent was administered in a single "push" via the modified angiography catheter positioned in the endotracheal tube at the beginning of the inspiration phase after two minutes of consolidated atrial fibrillation. Sterile water (2 ml) was used as a placebo for intratracheal instillation in the baseline AF. A washout period of 30 to 60 min was allowed between inductions of each occurrence of AF.

AF duration was compared starting at 2 min after AF was induced, when the IT instillation was administered. The average ventricular rate for each AF was obtained by the mean of six measurements of ventricular rate performed each 30 seconds between the IT delivery (sterile water or metoprolol instillation) and the AF conversion to sinus rhythm. Contractility (LV dP/dt) and MAP were recorded during atrial pacing at 160 beats/min before AF was induced and after it was terminated.

Plasma Samples

Blood samples were drawn from a 7 Fr sheath placed in the jugular vein and transferred into sodium heparin tubes at 0, 2, 5, 10, 15, and 30 min after the start of intratracheal metoprolol instillation. All the samples were centrifuged and frozen at −80° C.

Statistical Analysis

Statistical analyses were performed using the SAS system (version 9.4) to apply ANOVA with post-hoc Dunnett's test for each time point. Data are reported as means±SEM. Statistical significance was assumed at p<0.05.

Results

Atrial Fibrillation Duration

Figure 2:
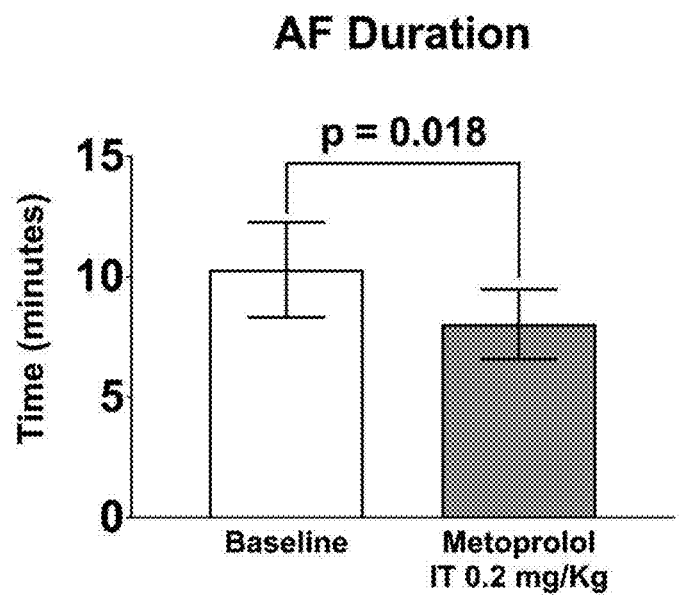
FIG. 2 is a graph summarizing the reduction of AF duration induced by intratracheal administration of metoprolol.

Intratracheal metoprolol resulted in a significant 20.4±4.9% shortening of the AF duration in comparison to the placebo baseline AF with the sterile water intratracheal delivery (from 10.3±2.0 to 8.0±1.5 min, p=0.018). An illustrative example of acceleration of conversion of AF is illustrated in FIG. 1. Note the direct transition to normal sinus rhythm. In none of the animals did atrial flutter occur. The summary data on AF duration are presented in FIG. 2.

Effects on PR Interval, AF Dominant Frequency and Ventricular Rate During AF

Figure 3:
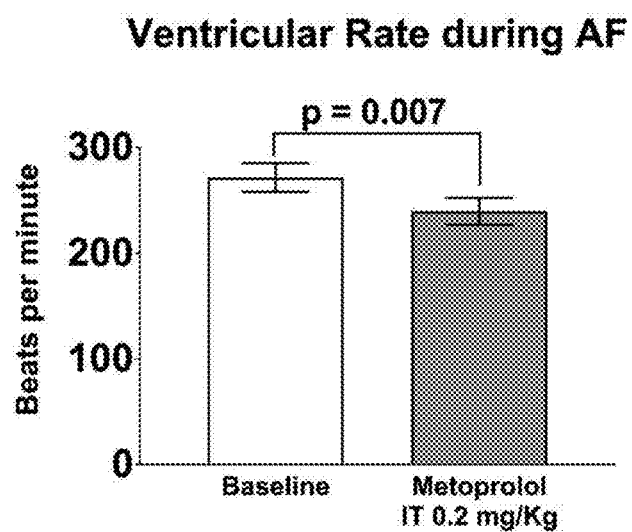
FIG. 3 is a graph summarizing the reduction of ventricular rate during AF induced by intratracheal administration of metoprolol.

Metoprolol delivery of 0.2 mg/kg bolus resulted in a trend towards an increase in PR interval by 4% when compared with the time of AF conversion (from 174±11.2 to 182±11.4 msec, p=0.07). AF dominant frequency was significantly reduced by 31% comparing metoprolol with baseline AF, from 8.7±0.94 to 6±1.1 Hz (p=0.04). Intratracheal instillation of metoprolol significantly reduced ventricular rate during AF by 32 beats/min or 12±2.6% (from 272±13.7 to 240±12.6 beats/min, p=0.007) when compared to baseline AF with the sterile water intratracheal delivery (FIG. 3).

Figure 4:
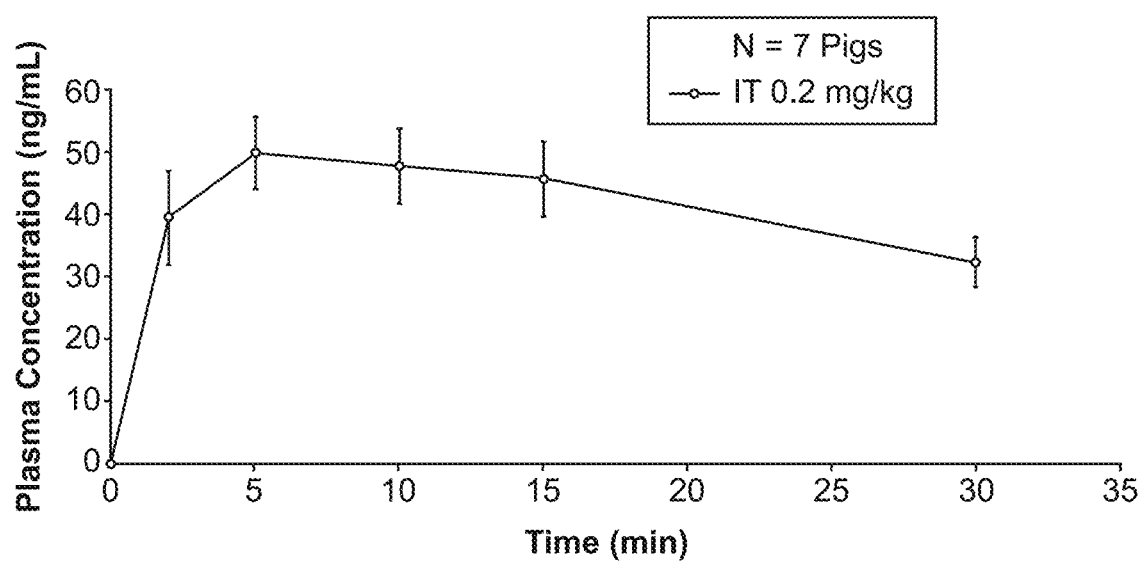
FIG. 4 is a graph summarizing plasma concentration of metoprolol after the intratracheal administration.

Time Course of Plasma Levels Following Intratracheal Administration of Metoprolol The pattern of increase in plasma levels of metoprolol following intratracheal instillation of metoprolol exhibited a classical pharmacokinetic response with relatively abrupt peak occurring within 2 to 4 min followed by a slower decay due to systemic distribution of the drug (FIG. 4).

Effects on Left Ventricular Contractility and Mean Arterial Pressure

Figure 5:
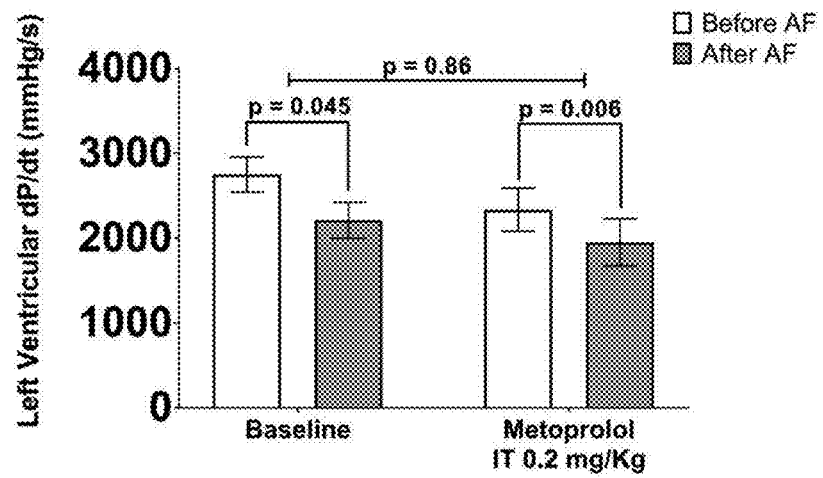
FIG. 5 is a graph summarizing the changes in contractility before and after AF in animals receiving intratracheal administration of placebo or metoprolol.

The AF baseline significantly decreased contractility (LV dP/dt) by 18.9±6.2% (from 2749±206.8 to 2211±210.3, p=0.045) after the conversion. Similarly, the IT instillation of metoprolol caused a 17.5±4.0% reduction (from 2337±252.7 to 1951±277.9, p=0.006). There were no significant difference between the reductions in contractility (p=0.85) (FIG. 5).

Figure 6:
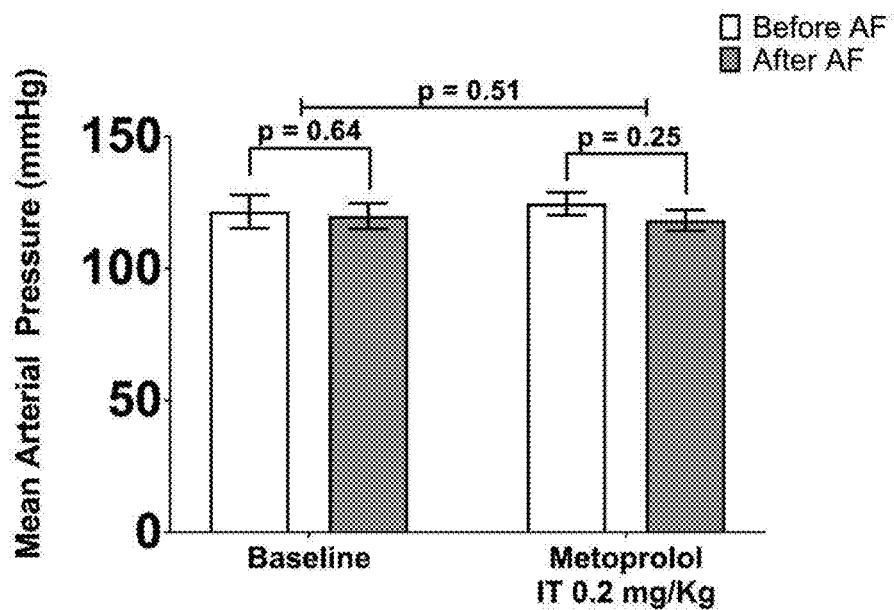
FIG. 6 is a graph summarizing the changes in mean arterial pressure (MAP) before and after AF in animals receiving intratracheal administration of placebo or metoprolol.

There were no significant changes in the MAP for the AF with sterile water delivery (from 122±6.3 to 120±4.8, p=0.64) or with metoprolol instillation (from 125±4.3 to 118±4.0, p=0.26). The decrease in MAP was not significant different between the groups (p=0.51) (FIG. 6). All measurements were made during 160 beats/min pacing.

This example demonstrates that the pulmonary delivery of metoprolol effectively terminates AF and reduces ventricular rate during the arrhythmia.

Example 6. Electropharmacological Effects of IT Administration of Beta Blocker, Nebivolol or Nebivolol, Alone or in Combination with Class Ic Antiarrhythmic Agent Flecainide in Pig Models with Induced Atrial Fibrillation In this example, the electropharmacologic effects of IT delivery of nebivolol or metoprolol, alone or in combination with flecainide, on atrial and ventricular electrical properties with respect to their effectiveness in converting atrial fibrillation to sinus rhythm, as well as their adverse effects on left ventricular contractility and atrial blood pressure.

Experimental Preparation

The investigations were conducted in male Yorkshire pigs. The animals were preanesthetized with telazol (4.7 mg/kg, intramuscular) and subsequently were further anesthetized using alpha-chloralose (80-mg/kg IV bolus followed by 24-mg/kg/h continuous IV infusion). The pigs were intubated and ventilated at a constant rate of 12 breaths/min and tidal volume of 400 ml per stroke.

The catheters were positioned under fluoroscopic control. Electrograms were recorded from a decapolar electrode catheter positioned in the LV. Mean arterial pressure (MAP) was continuously recorded from a femoral arterial sheath. LV blood pressure was continuously monitored from a pigtail catheter. A catheter was introduced into the pericardial space via the right atrial appendage for delivery of intrapericardial acetylcholine. Atrial pacing at 160 beats/min was accomplished by delivering electrical stimuli to the right atrial catheter electrodes. Electrograms were monitored using a Prucka CardioLab workstation (GE Medical Systems, Milwaukee Wis.) from atrial and ventricular sites. For intratracheal instillation of metoprolol solution or sterile water, a 5 Fr angiography catheter was introduced into the trachea via the endotracheal tube, extending ~1 cm past the tube, and its tip was positioned under fluoroscopy at the tracheal carina level.

Reagents

Metoprolol obtained in powder form was used to prepare a stock solution of 15.3 mg/ml by dissolving the drug in 100% dimethyl sulfoxide (DMSO). A volume was withdrawn from the stock solution to achieve a 2 mg/kg IT dose and was supplemented with sterile water to attain a 2 ml total volume for bolus injection.

For Nebivolol (racemic mixtures of d- and l-nebivolol), a stock solution of 25 mg/ml was prepared by dissolving the drug in 100% DMSO. The dose was 0.3 mg/kg for intratracheal instillation. The corresponding volume was withdrawn from the stock solution based on body weight of the pig, and the allocated volume was completed with sterile water to attain 2 ml total volume. The administration was made with a 5 cc syringe with 2 ml of 0.3 mg/kg nebivolol solution and 3 ml of air.

Study Protocols

AF was induced with 1 mL of a 102.5 mM solution of acetylcholine bolus delivered through the pericardial catheter, followed by saline flush (2 mL). Burst pacing at a cycle length of 178 ms was performed at 1 minute after intrapericardial administration of ACh. After AF initiation, lavage was carried out with 20 mL of saline.

For the intratracheal instillation of metoprolol (0.2 mg/kg or 0.4 mg/kg), nebivolol (0.3 mg/kg), flecainide (0.75 mg/kg), or cocktail of metoprolol and flecainide (0.2 mg/kg and 0.75 mg/kg, respectively), the drug agent was administered in 2 mL total volume in a single "push" of 2-3 seconds, followed by 3 ml of air in a 5 ml syringe, via the modified angiography catheter positioned in the endotracheal tube at the beginning of the inspiration phase after two minutes of consolidated atrial fibrillation. Sterile water (2 ml) was used as a placebo for intratracheal instillation in the baseline AF. A washout period of 30 to 60 min was allowed between inductions of each occurrence of AF.

AF duration was compared starting at 2 min after AF was induced, when the IT instillation was administered. The average ventricular rate for each AF was obtained by the mean of six measurements of ventricular rate performed each 30 seconds between the IT delivery (sterile water or metoprolol instillation) and the AF conversion to sinus rhythm.

For the study of nebivolol, in 2 of the 4 animals that were tested, at 60 min following nebivolol administration, flecainide was administered to test the effect of combined use of nebivolol and flecainide. For the study of metoprolol, given that metoprolol can have a short half-life in vivo, the effect of combined use of metoprolol and flecainide was tested by giving a second IT dose of metoprolol-flecainide cocktail 60 min following the first IT dose of metoprolol in the animals.

Results

Atrial Fibrillation Duration

Figure 7:
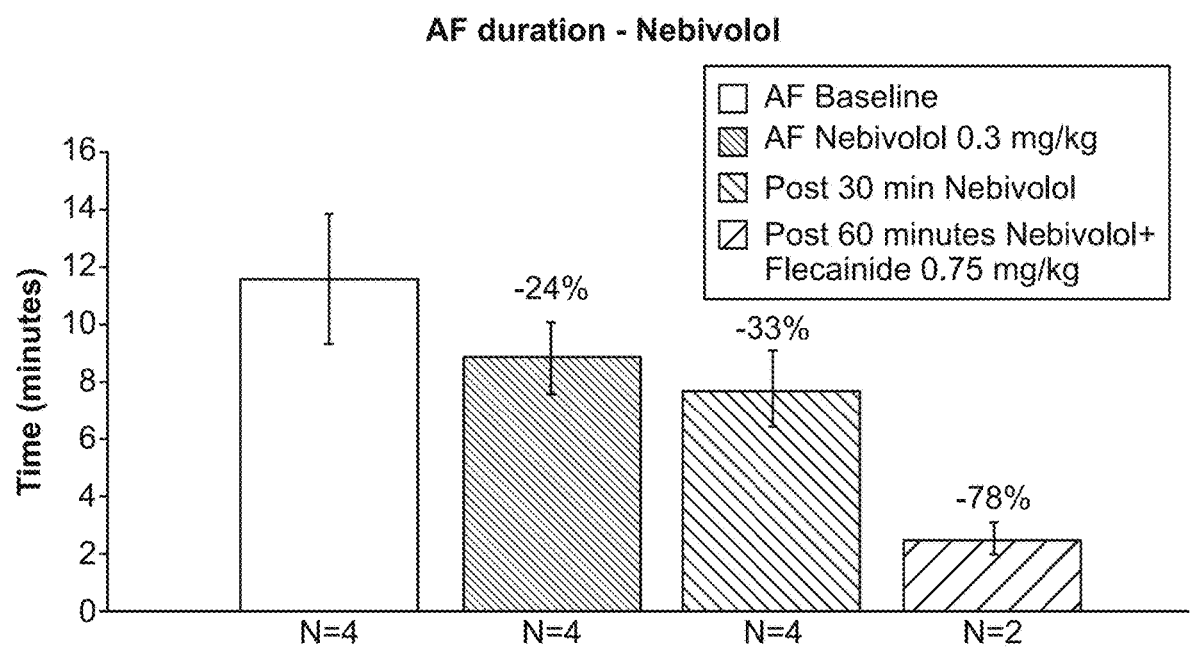
FIG. 7 is a graph summarizing the effects on the AF duration of intratracheal administration of 0.3 mg/kg nebivolol, alone or in combination with 0.75 mg/kg flecainide.

As shown in FIG. 7, intratracheal nebivolol (0.3 mg/kg) resulted in about 24% shortening of the AF duration in comparison to the placebo baseline AF when administered right before the AF induction. The duration of AF that was induced 30 min after the IT administration of nebivolol was shortened by about 33%. In some of the animals, 0.75 mg/kg of flecainide was administered intratracheally 60 min after the IT administration of nebivolol. The addition of flecainide further reduced the AF duration, about 78% as compared to the placebo baseline AF.

Figure 9:
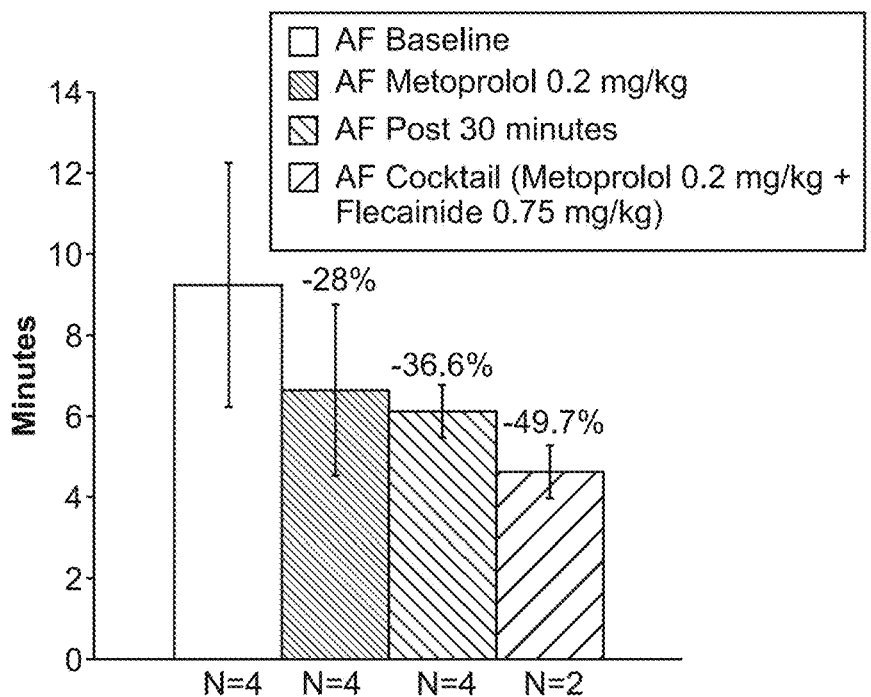
FIG. 9 is a graph summarizing the effects on the AF duration of intratracheal administration of 0.2 mg/kg metoprolol, alone or in a cocktail with 0.75 mg/kg flecainide.

Similar to the effect of nebivolol, IT administration of metoprolol also reduced AF duration. As shown in FIG. 9, the duration of the AF induced right after IT delivery of 0.2 mg/kg metoprolol alone was shortened by about 28% as compared to the placebo baseline AF. The duration of the AF induced 30 min after IT delivery of metoprolol was shortened by about 36%. 60 min after the first IT delivery of metoprolol, a cocktail of 0.2 mg/kg metoprolol and 0.75 mg/kg flecainide reduced the AF duration by about 50%.

Effects on Ventricular Rate During AF

Figure 8:
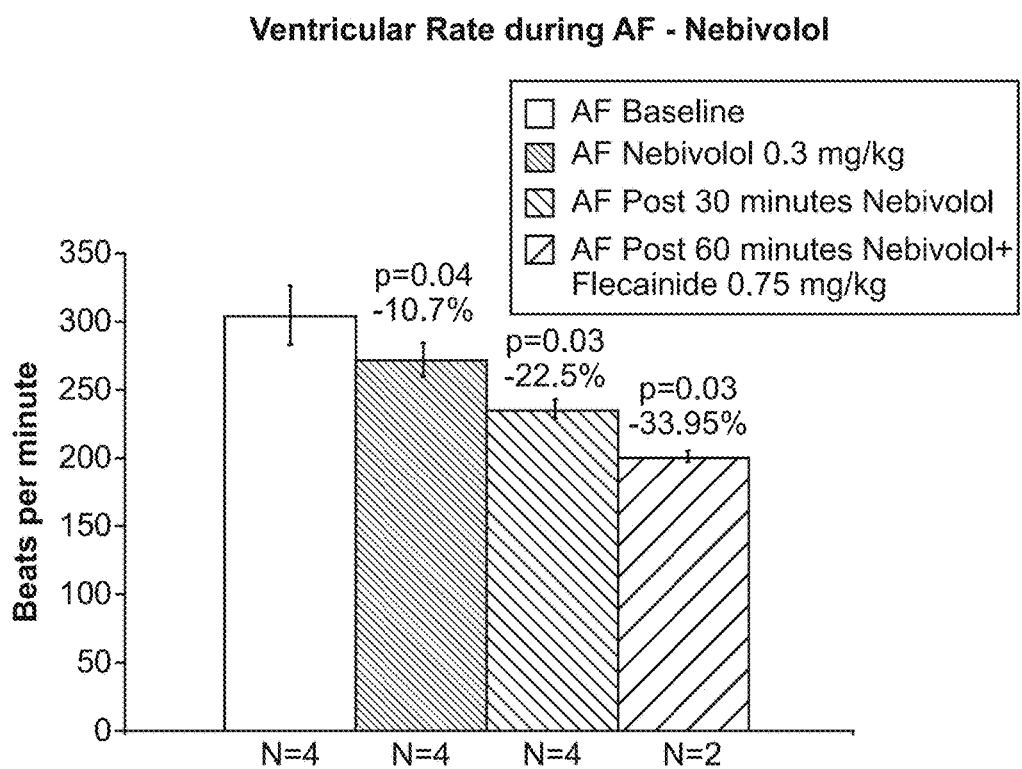
FIG. 8 is a graph summarizing the effects on the ventricular rate during AF of intratracheal administration of 0.3 mg/kg nebivolol, alone or in combination with 0.75 mg/kg flecainide.
Figure 10:
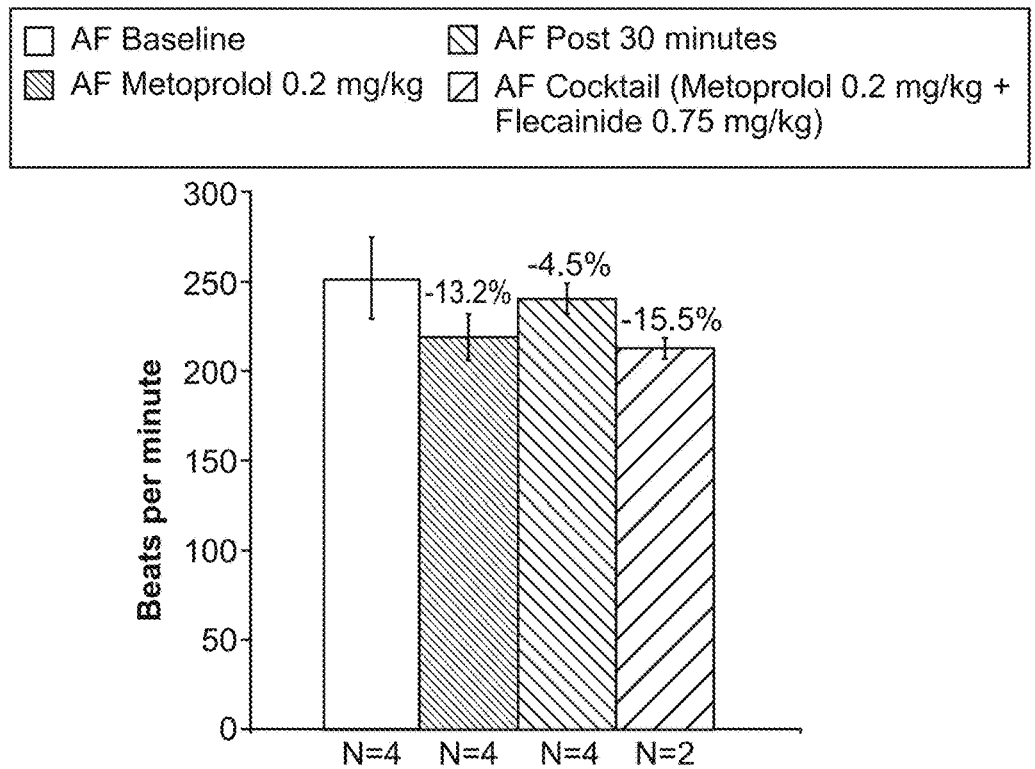
FIG. 10 is a graph summarizing the effects on the ventricular rate during AF of intratracheal administration of 0.2 mg/kg metoprolol, alone or in a cocktail with 0.75 mg/kg flecainide.

It was also observed that IT administration of nebivolol or metoprolol slowed ventricular rate during AF. As shown in FIG. 8, there was about 10% reduction in ventricular rate when AF was induced right after the nebivolol administration, about 22% reduction when AF was induced 30 min later, and about 34% reduction when IT flecainide was administered 60 min later and AF induced afterward. As shown in FIG. 10, IT metoprolol reduced ventricular rate by about 13% during AF induced right after the metoprolol administration as compared to baseline AF. Possibly due to the short half-life of metoprolol in vivo, the reduction of ventricular rate during AF 30 min after the metoprolol was moderate. 60 min later, when the cocktail of metoprolol land flecainide was delivered, the ventricular rate was reduced by 15.5%.

Example 7. Effects of IT Co-Delivery of Metoprolol and Flecainide

In this example, the electropharmacologic effects of IT co-delivery of metoprolol and flecainide were examined as compared to delivery of metoprolol alone.

Experimental animal models of AF (male Yorkshire pigs), and study reagents (metoprolol and flecainide) were prepared according to similar procedures described in Examples 5 and 6. In this example, the animals received IT administration of either metoprolol alone (0.2 mg/kg or 0.4 mg/kg), a cocktail of metoprolol and flecainide (0.2 mg/kg and 0.75 mg/kg, respectively, or 0.4 mg/kg and 0.75 mg/kg, respectively), or flecainide alone (0.75 mg/kg).

Figure 11:
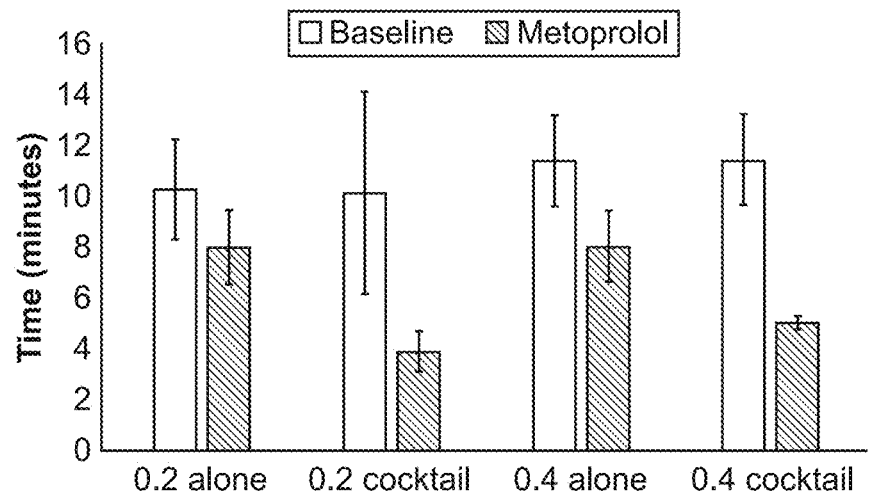
FIGS. 11 and 12 are graphs summarizing the effects on the AF duration of intratracheal administration of 0.2 mg/kg or 0.4 mg/kg metoprolol, alone or in a cocktail with 0.75 mg/kg flecainide.
Figure 12:
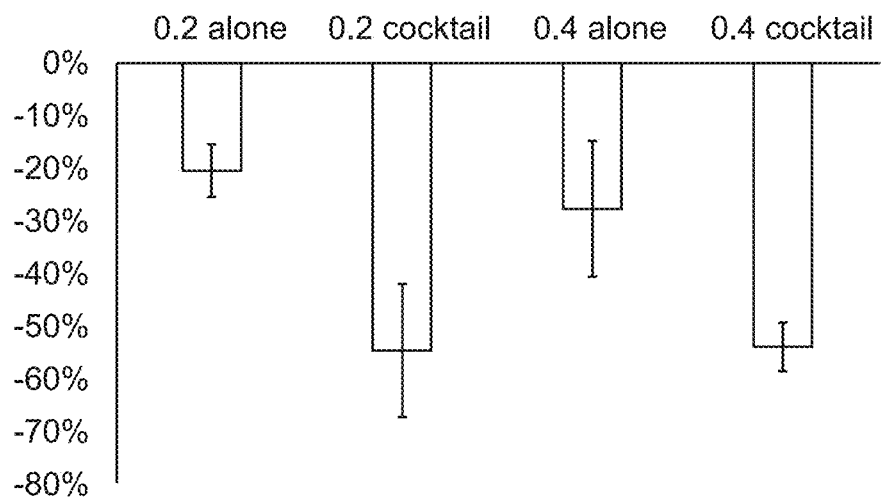
Figure 13:
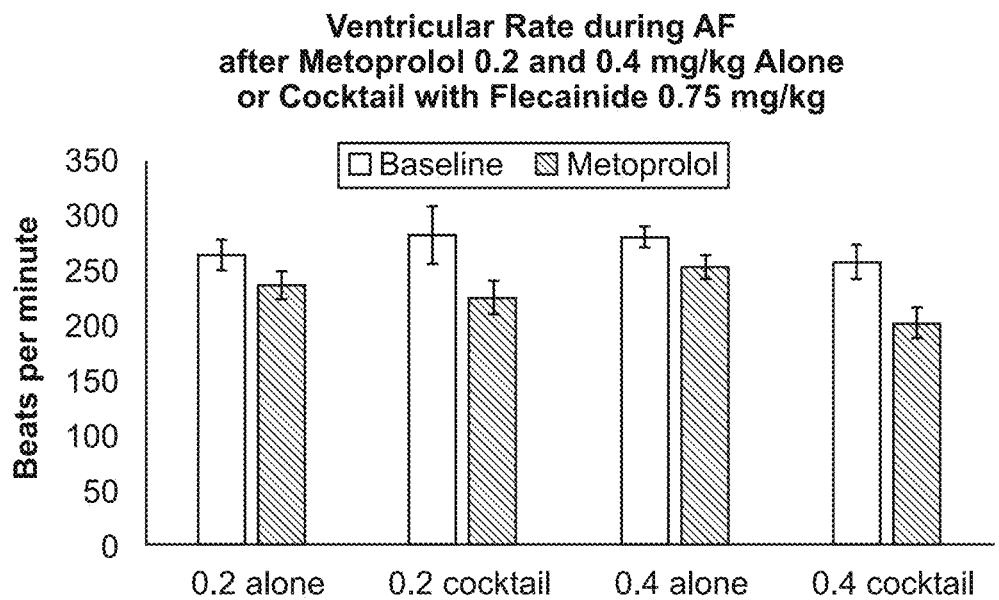
FIGS. 13 and 14 are graphs summarizing the effects on the ventricular rate during AF of intratracheal administration of 0.2 mg/kg or 0.4 mg/kg metoprolol, alone or in a cocktail with 0.75 mg/kg flecainide.
Figure 14:
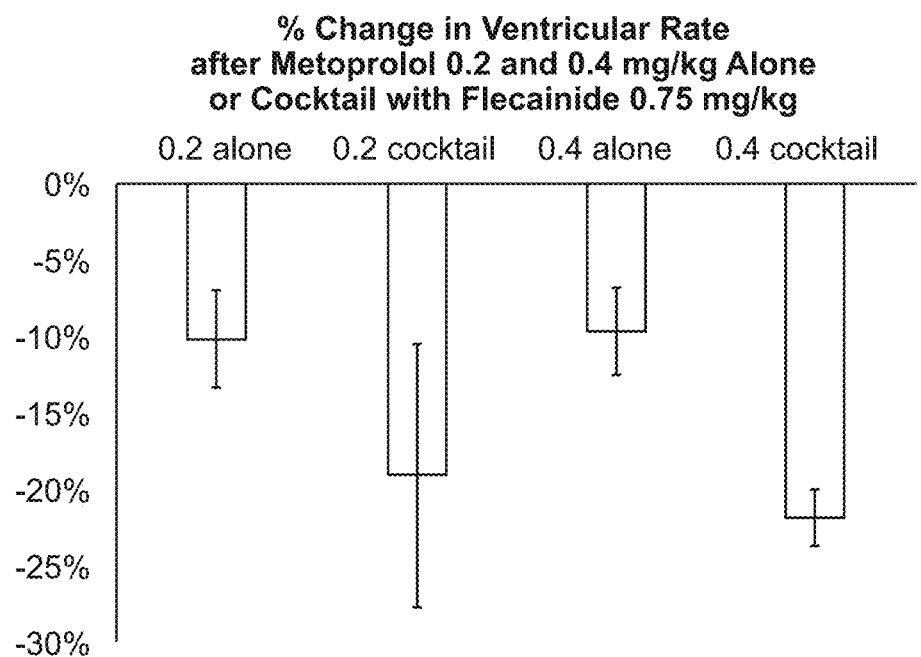

As shown in FIGS. 11 and 12, IT delivery of metoprolol alone or the cocktails all resulted in AF cardioversion, reducing the AF duration. More specifically, 0.2 mg/kg metoprolol alone resulted in about 20% reduction in the AF duration, and 0.4 mg/kg metoprolol alone about 27% reduction, while cocktails with 0.2 mg/kg or 0.4 mg/kg metoprolol both resulted in more than 50% reduction. Similar effects were observed with respect to the ventricular rate during the AF conversion. Metoprolol alone (both 0.2 mg/kg or 0.4 mg/kg dosages) led to about 10% reduction in the average ventricular rate during the AF conversion, while the cocktails led to further reduction (close to 20% for cocktail with 0.2 mg/kg metoprolol and about 22% for cocktail with 0.4 mg/kg metoprolol, FIGS. 13 and 14).

Figure 15:
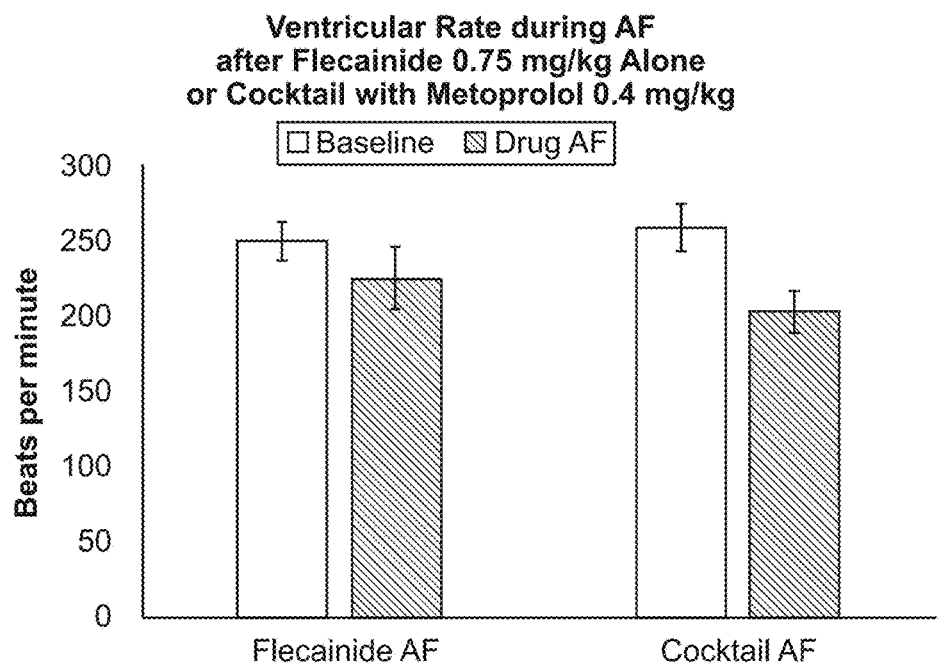
FIGS. 15 and 16 are graphs summarizing the effects on the ventricular rate during AF of intratracheal administration of 0.75 mg/kg flecainide, alone or in a cocktail with 0.4 mg/kg metoprolol.
Figure 16:
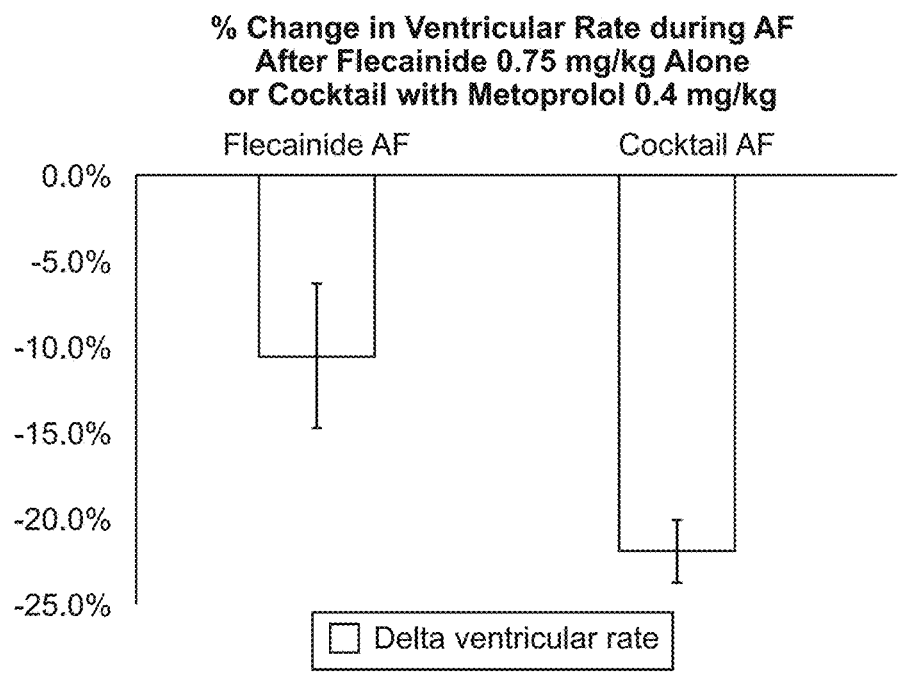

Comparisons were also made between IT administration of 0.75 mg/kg flecainide alone and the cocktail with 0.75 mg/kg flecainide and 0.4 mg/kg metoprolol. As shown in FIGS. 15 and 16, flecainide alone induced about 10% reduction in the average ventricular rate during AF, while the cocktail about 22% reduction.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein may be employed in practicing the present disclosure. It is intended that the following claims define the scope of the disclosure and that methods and structures within the scope of these claims and their equivalents be covered thereby.

What is claimed is:

1. A method of treating a subject suffering from atrial arrhythmia, comprising administering to said subject via inhalation:
   (i) a therapeutically effective amount of a β1-selective adrenergic receptor blocker; and
   (ii) a therapeutically effective amount of a class I antiarrhythmic agent,
      wherein said therapeutically effective amount of said β1-selective adrenergic receptor blocker and said therapeutically effective amount of said class I antiarrhythmic agent, when both are administered via inhalation to an experimental subject suffering from said atrial arrhythmia in a clinical study, induce a faster cardioversion of said atrial arrhythmia in said experimental subject as compared to:
         (a) administering said therapeutically effective amount of said β1-selective adrenergic receptor blocker via inhalation to a control subject suffering from said atrial arrhythmia in said clinical study without a class I antiarrhythmic agent; or
         (b) administering said therapeutically effective amount of said class I antiarrhythmic agent via inhalation to a control subject suffering from said atrial arrhythmia in said clinical study without a β1-selective adrenergic receptor blocker; and
      wherein said inhalation administration of both said therapeutically effective amount of said β1-selective adrenergic receptor blocker and said therapeutically effective amount of said class I antiarrhythmic agent slows atrioventricular node conduction during said cardioversion.

2. The method of claim 1, wherein said administering of both said therapeutically effective amount of said β1-selective adrenergic receptor blocker and said therapeutically effective amount of said class I antiarrhythmic agent prolongs PR interval in said experimental subject during said cardioversion as measured by electrocardiograph.

3. The method of claim 2, wherein said PR interval in said experimental subject is prolonged by at least 5%.

4. The method of claim 1, wherein said administering of both said therapeutically effective amount of said β1-selective adrenergic receptor blocker and said therapeutically effective amount of said class I antiarrhythmic agent reduces average ventricular rate in said experimental subject during said cardioversion by at least 10%.

5. The method of claim 1, comprising administering about 1 mg to about 4 mg of said β1-selective adrenergic receptor blocker.

6. The method of claim 1, wherein said β1-selective adrenergic receptor blocker is administered at a concentration of about 2 mg/mL to about 30 mg/mL.

7. The method of claim 1, wherein said β1-selective adrenergic receptor blocker comprises metoprolol or a pharmaceutically acceptable salt or solvate thereof.

8. The method of claim 7, comprising administering about 1 mg to about 4 mg metoprolol or a pharmaceutically acceptable salt or solvate thereof at a concentration of about 2 mg/mL to about 30 mg/mL.

9. The method of claim 1, wherein said β1-selective adrenergic receptor blocker comprises nebivolol or a pharmaceutically acceptable salt or solvate thereof.

10. The method of claim 1, wherein said β1-selective adrenergic receptor blocker is administered up to about 90 minutes earlier than said therapeutically effective amount of said class I antiarrhythmic agent.

11. The method of claim 1, wherein said β1-selective adrenergic receptor blocker is administered concurrently with said class I antiarrhythmic agent.

12. The method of claim 1, comprising administering about 1 mg to about 4 mg metoprolol or a pharmaceutically acceptable salt or solvate thereof at a concentration of about 2 mg/mL to about 30 mg/mL up to 90 minutes prior to administering about 20 mg to about 150 mg flecainide or a pharmaceutically acceptable salt or solvate thereof via aerosolization.

13. The method of claim 1, comprising administering concurrently via aerosolization about 1 mg to about 4 mg metoprolol or a pharmaceutically acceptable salt or solvate thereof at a concentration of about 2 mg/mL to about 30 mg/mL and about 20 mg to about 150 mg flecainide or a pharmaceutically acceptable salt or solvate thereof.

14. The method of claim 1, wherein said atrial arrhythmia comprises atrial fibrillation.

15. A method of treating a patient suffering from atrial arrhythmia, comprising administering to said patient via inhalation:

(i) a therapeutically effective amount of a β1-selective adrenergic receptor blocker; and (ii) a therapeutically effective amount of a class I antiarrhythmic agent, wherein said therapeutically effective amount of said β1-selective adrenergic receptor blocker and said therapeutically effective amount of said class I antiarrhythmic agent, when both are administered via inhalation to an experimental subject suffering from said atrial arrhythmia in a clinical study, induce cardioversion in said experimental subject and induce a greater reduction in average ventricular rate during said cardioversion in said experimental subject as compared to:

(a) administering said therapeutically effective amount of said β1-selective adrenergic receptor blocker via inhalation to a control subject suffering from said atrial arrhythmia in said clinical study without a class I antiarrhythmic agent; or (b) administering said therapeutically effective amount of said class I antiarrhythmic agent via inhalation to a control subject suffering from said atrial arrhythmia in said clinical study without a β1-selective adrenergic receptor blocker; and wherein said inhalation administration of both said therapeutically effective amount of said β1-selective adrenergic receptor blocker and said therapeutically effective amount of said class I antiarrhythmic agent slows atrioventricular node conduction during said cardioversion.

16. The method of claim 15, wherein said administering of both said therapeutically effective amount of said β1-selective adrenergic receptor blocker and said therapeutically effective amount of said class I antiarrhythmic agent prolongs PR interval in said experimental subject during said cardioversion as measured by electrocardiograph.

17. The method of claim 16, wherein said PR interval in said experimental subject is prolonged by at least 5%.

18. The method of claim 15, wherein said administering of both said therapeutically effective amount of said β1-selective adrenergic receptor blocker and said therapeutically effective amount of said class I antiarrhythmic agent reduces average ventricular rate in said experimental subject during said cardioversion by at least 10%.

19. The method of claim 15, comprising administering about 1 mg to about 4 mg of said β1-selective adrenergic receptor blocker.

20. The method of claim 15, wherein said β1-selective adrenergic receptor blocker is administered at a concentration of about 2 mg/mL to about 30 mg/mL.

21. The method of claim 15, wherein said β1-selective adrenergic receptor blocker comprises metoprolol or a pharmaceutically acceptable salt or solvate thereof.

22. The method of claim 21, comprising administering about 1 mg to about 4 mg metoprolol or a pharmaceutically acceptable salt or solvate thereof at a concentration of about 2 mg/mL to about 30 mg/mL.

23. The method of claim 15, wherein said β1-selective adrenergic receptor blocker comprises nebivolol or a pharmaceutically acceptable salt or solvate thereof.

24. The method of claim 15, wherein said β1-selective adrenergic receptor blocker is administered up to about 90 minutes earlier than said dosage therapeutically effective amount of said class I antiarrhythmic agent.

25. The method of claim 15, wherein said β1-selective adrenergic receptor blocker is administered concurrently with said class I antiarrhythmic agent.

26. The method of claim 15, comprising administering about 1 mg to about 4 mg metoprolol or a pharmaceutically acceptable salt or solvate thereof at a concentration of about 2 mg/mL to about 30 mg/mL up to 90 minutes prior to administering about 20 mg to about 150 mg flecainide or a pharmaceutically acceptable salt or solvate thereof via aerosolization.

27. The method of claim 15, comprising administering concurrently via aerosolization about 1 mg to about 4 mg metoprolol or a pharmaceutically acceptable salt or solvate thereof at a concentration of about 2 mg/mL to about 30 mg/mL and about 20 mg to about 150 mg flecainide or a pharmaceutically acceptable salt or solvate thereof.

28. The method of claim 15, wherein said atrial arrhythmia comprises atrial fibrillation.

29. The method of claim 1, wherein said slowing of said atrioventricular node conduction is evidenced by electrocardiograph.

30. The method of claim 15, wherein said slowing of said atrioventricular node conduction is evidenced by electrocardiograph.

* * * * *